US008889632B2

(12) United States Patent
Bernal et al.

(10) Patent No.: US 8,889,632 B2
(45) Date of Patent: Nov. 18, 2014

(54) STABILIZED P53 PEPTIDES AND USES THEREOF

(75) Inventors: Federico Bernal, Brookline, MA (US); Loren D. Walensky, Chestnut Hill, MA (US); Gregory L. Verdine, Newton, MA (US); Stanley J. Korsmeyer, Weston, MA (US); Susan Korsmeyer, legal representative, Weston, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 1402 days.

(21) Appl. No.: 12/525,123

(22) PCT Filed: Jan. 31, 2008

(86) PCT No.: PCT/US2008/052580
§ 371 (c)(1),
(2), (4) Date: Mar. 18, 2010

(87) PCT Pub. No.: WO2008/095063
PCT Pub. Date: Aug. 7, 2008

(65) Prior Publication Data
US 2010/0168388 A1 Jul. 1, 2010

Related U.S. Application Data

(60) Provisional application No. 60/887,526, filed on Jan. 31, 2007.

(51) Int. Cl.
*A61K 38/10* (2006.01)
*A61K 38/12* (2006.01)
*A61K 38/16* (2006.01)
*C07K 7/08* (2006.01)
*C07K 7/50* (2006.01)
*C07K 1/113* (2006.01)
*C07K 14/47* (2006.01)

(52) U.S. Cl.
CPC ............. *C07K 14/4746* (2013.01); *C07K 1/113* (2013.01)
USPC ........ 514/21.4; 514/21.2; 514/21.1; 530/326; 530/324; 530/317

(58) Field of Classification Search
None
See application file for complete search history.

(56) References Cited

U.S. PATENT DOCUMENTS

| | | | |
|---|---|---|---|
| 4,270,537 A | 6/1981 | Romaine | |
| 4,596,556 A | 6/1986 | Morrow et al. | |
| 4,730,006 A | 3/1988 | Bohme et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,310,910 A * | 5/1994 | Drtina et al. .................... | 546/49 |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,364,851 A | 11/1994 | Joran | |
| 5,383,851 A | 1/1995 | McKinnon et al. | |
| 5,417,662 A | 5/1995 | Hjertman et al. | |
| 5,446,128 A | 8/1995 | Kahn | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,622,852 A | 4/1997 | Korsmeyer | |
| 5,649,912 A | 7/1997 | Peterson | |
| 5,663,316 A | 9/1997 | Xudong | |
| 5,672,584 A | 9/1997 | Borchardt et al. | |
| 5,702,908 A | 12/1997 | Picksley et al. | |
| 5,704,911 A | 1/1998 | Parsons | |
| 5,708,136 A | 1/1998 | Burrell et al. | |
| 5,750,767 A | 5/1998 | Carpino et al. | |
| 5,756,669 A | 5/1998 | Bischoff et al. | |
| 5,770,377 A | 6/1998 | Picksley et al. | |
| 5,811,515 A | 9/1998 | Grubbs et al. | |
| 5,824,483 A | 10/1998 | Houston, Jr. et al. | |
| 5,834,209 A | 11/1998 | Korsmeyer | |

(Continued)

FOREIGN PATENT DOCUMENTS

CZ 9700369 A3 9/1998
EP 0528312 A2 2/1993

(Continued)

OTHER PUBLICATIONS

Lu, Journal of Combinatorial Chemistry (2006), 8(3), 315-325.*
STN search notes for Lu reference, 4 pages, 2006.*
Baek, et al. Structure of the stapled p53 peptide bound to Mdm2. J Am Chem Soc. Jan. 11, 2012;134(1):103-6. doi: 10.1021/ja2090367. Epub Dec. 14, 2011.
Bernal, et al. A stapled p53 helix overcomes HDMX-mediated suppression of p53 Cancer Cell. Nov. 16, 2010;18(5):411-22. doi: 10.1016/j.ccr.2010.10.024.
Bottger, et al. Molecular characterization of the hdm2-p53 interaction. J Mol Biol. Jun. 27, 1997;269(5):744-56.
Hu, et al. Efficient p53 activation and apoptosis by simultaneous disruption of binding to MDM2 and MDMX. Cancer Res. Sep. 15, 2007;67(18):8810-7.

(Continued)

*Primary Examiner* — Satyanarayana R Gudibande
(74) *Attorney, Agent, or Firm* — Wilson Sonsini Goodrich & Rosati, P.C.

(57) ABSTRACT

Cross-linked peptides related to human p53 and bind to HMD2 or a family member of HDM2 useful for promoting apoptosis, e.g., in the treatment of and identifying therapeutic agents that binding to HMD2 or a family member of HDM2.

25 Claims, 23 Drawing Sheets

(56) References Cited

U.S. PATENT DOCUMENTS

| | | | |
|---|---|---|---|
| 5,856,445 A | 1/1999 | Korsmeyer |
| 5,874,529 A | 2/1999 | Gilon et al. |
| 5,893,397 A | 4/1999 | Peterson et al. |
| 5,922,863 A | 7/1999 | Grubbs et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,030,997 A | 2/2000 | Eilat et al. |
| 6,043,339 A | 3/2000 | Lin et al. |
| 6,046,289 A | 4/2000 | Komazawa et al. |
| 6,051,554 A | 4/2000 | Hornik et al. |
| 6,153,391 A | 11/2000 | Picksley et al. |
| 6,169,073 B1 | 1/2001 | Halazonetis et al. |
| 6,184,344 B1 | 2/2001 | Kent et al. |
| 6,245,886 B1 | 6/2001 | Halazonetis et al. |
| 6,271,198 B1 | 8/2001 | Braisted et al. |
| 6,326,354 B1 | 12/2001 | Gross et al. |
| 6,420,118 B1 | 7/2002 | Halazonetis et al. |
| 6,420,136 B1 | 7/2002 | Riabowol et al. |
| 6,495,674 B1 | 12/2002 | Lemke et al. |
| 6,569,993 B1 | 5/2003 | Sledeski et al. |
| 6,610,657 B1 | 8/2003 | Goueli |
| 6,613,874 B1 | 9/2003 | Mazur et al. |
| 6,703,382 B2 | 3/2004 | Wang et al. |
| 6,713,280 B1 | 3/2004 | Huang et al. |
| 6,784,157 B2 | 8/2004 | Halazonetis et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,183,059 B2 | 2/2007 | Verdine et al. |
| 7,189,801 B2 | 3/2007 | Halazonetis et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,666,983 B2 | 2/2010 | Halazonetis et al. |
| 7,705,118 B2 | 4/2010 | Arora et al. |
| 7,723,469 B2 | 5/2010 | Walensky et al. |
| 7,737,174 B2 | 6/2010 | Wang et al. |
| 7,745,573 B2 | 6/2010 | Robinson et al. |
| 7,759,383 B2 | 7/2010 | Wang et al. |
| 7,786,072 B2 | 8/2010 | Verdine et al. |
| 7,884,107 B2 | 2/2011 | Ma et al. |
| 7,893,278 B2 | 2/2011 | Haley et al. |
| 7,927,813 B2 | 4/2011 | Geneste et al. |
| 7,932,397 B2 | 4/2011 | Hock et al. |
| 7,960,506 B2 | 6/2011 | Nash et al. |
| 7,964,724 B2 | 6/2011 | Fotouhi et al. |
| 7,981,999 B2 | 7/2011 | Nash |
| 8,017,607 B2 | 9/2011 | Bartkovitz et al. |
| 8,058,269 B2 | 11/2011 | Chen et al. |
| 8,071,541 B2 | 12/2011 | Arora et al. |
| 8,076,482 B2 | 12/2011 | Chen et al. |
| 8,088,815 B2 | 1/2012 | Bartkovitz et al. |
| 8,088,931 B2 | 1/2012 | Wang et al. |
| 8,124,726 B2 | 2/2012 | Robinson et al. |
| 8,198,405 B2 * | 6/2012 | Walensky et al. ............. 530/324 |
| 8,217,051 B2 | 7/2012 | Zhang et al. |
| 8,324,428 B2 | 12/2012 | Verdine et al. |
| 8,343,760 B2 | 1/2013 | Lu et al. |
| 8,399,405 B2 | 3/2013 | Nash et al. |
| 2002/0098580 A1 | 7/2002 | Nandabalan et al. |
| 2002/0132977 A1 | 9/2002 | Yuan et al. |
| 2003/0027766 A1 | 2/2003 | Ioannides et al. |
| 2003/0060432 A1 | 3/2003 | Tocque et al. |
| 2003/0144331 A1 | 7/2003 | Gudkov et al. |
| 2003/0176318 A1 | 9/2003 | Gudkov et al. |
| 2004/0023887 A1 | 2/2004 | Pillutla et al. |
| 2004/0038901 A1 | 2/2004 | Basler et al. |
| 2004/0067503 A1 | 4/2004 | Tan et al. |
| 2004/0115135 A1 | 6/2004 | Quay |
| 2004/0146971 A1 | 7/2004 | Lane et al. |
| 2004/0170653 A1 | 9/2004 | Stanislawski et al. |
| 2004/0170971 A1 | 9/2004 | Kinzler et al. |
| 2004/0171809 A1 | 9/2004 | Korsmeyer et al. |
| 2004/0228866 A1 | 11/2004 | Lu |
| 2004/0235746 A1 | 11/2004 | Hawiger et al. |
| 2004/0248198 A1 | 12/2004 | Kriwacki et al. |
| 2004/0265931 A1 | 12/2004 | Gu et al. |
| 2005/0013820 A1 | 1/2005 | Holoshitz et al. |
| 2005/0037383 A1 | 2/2005 | Taremi et al. |
| 2005/0089511 A1 | 4/2005 | Roth et al. |
| 2005/0137137 A1 | 6/2005 | Lane et al. |
| 2005/0176075 A1 | 8/2005 | Jones et al. |
| 2005/0222224 A1 | 10/2005 | Gudkov et al. |
| 2005/0227932 A1 | 10/2005 | Lu et al. |
| 2005/0250680 A1 | 11/2005 | Walensky et al. |
| 2005/0277764 A1 | 12/2005 | Boyd et al. |
| 2006/0008848 A1 | 1/2006 | Verdine et al. |
| 2006/0014675 A1 | 1/2006 | Arora et al. |
| 2006/0100143 A1 | 5/2006 | Lu et al. |
| 2006/0149039 A1 | 7/2006 | Hunter et al. |
| 2006/0189511 A1 | 8/2006 | Koblish et al. |
| 2006/0233779 A1 | 10/2006 | Ben-Avraham et al. |
| 2007/0006332 A1 | 1/2007 | O'Neil |
| 2007/0032417 A1 | 2/2007 | Baell |
| 2007/0129324 A1 | 6/2007 | Boyd et al. |
| 2007/0274915 A1 | 11/2007 | Rao et al. |
| 2008/0081038 A1 | 4/2008 | Cho et al. |
| 2008/0085279 A1 | 4/2008 | Boyd et al. |
| 2008/0132485 A1 | 6/2008 | Wang et al. |
| 2008/0161426 A1 | 7/2008 | Gudkov et al. |
| 2008/0242598 A1 | 10/2008 | Fairlie et al. |
| 2008/0262200 A1 | 10/2008 | Nash |
| 2008/0305490 A1 | 12/2008 | Burrell et al. |
| 2008/0311608 A1 | 12/2008 | Tocque et al. |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0311174 A1 | 12/2009 | Allen |
| 2009/0326192 A1 | 12/2009 | Nash et al. |
| 2010/0010065 A1 | 1/2010 | Smith |
| 2010/0081611 A1 | 4/2010 | Bradner et al. |
| 2010/0093057 A1 | 4/2010 | Beattie et al. |
| 2010/0093086 A1 | 4/2010 | Lin et al. |
| 2010/0184628 A1 | 7/2010 | Nash |
| 2010/0184645 A1 | 7/2010 | Verdine et al. |
| 2010/0210515 A1 | 8/2010 | Nash et al. |
| 2010/0216688 A1 | 8/2010 | Nash et al. |
| 2010/0234563 A1 | 9/2010 | Arora et al. |
| 2010/0286362 A1 | 11/2010 | Boyd et al. |
| 2010/0298201 A1 | 11/2010 | Nash et al. |
| 2011/0021529 A1 | 1/2011 | Lain et al. |
| 2011/0028753 A1 | 2/2011 | Verdine et al. |
| 2011/0065915 A1 | 3/2011 | Malcolmson et al. |
| 2011/0144303 A1 | 6/2011 | Nash et al. |
| 2011/0144306 A1 | 6/2011 | Verdine et al. |
| 2011/0183917 A1 | 7/2011 | Lu et al. |
| 2011/0218155 A1 | 9/2011 | Walensky et al. |
| 2011/0245477 A1 | 10/2011 | Hoveyda et al. |
| 2011/0251252 A1 | 10/2011 | Wang et al. |
| 2011/0313167 A1 | 12/2011 | Doemling |
| 2012/0156197 A1 | 6/2012 | Errico et al. |
| 2012/0238507 A1 | 9/2012 | Fairlie et al. |
| 2012/0264738 A1 | 10/2012 | Sugimoto et al. |
| 2012/0270800 A1 | 10/2012 | Verdine et al. |
| 2012/0283269 A1 | 11/2012 | Blagosklonny et al. |
| 2012/0328692 A1 | 12/2012 | Lu et al. |
| 2013/0023646 A1 | 1/2013 | Nash et al. |
| 2013/0211046 A1 | 8/2013 | Verdine et al. |
| 2013/0330421 A1 | 12/2013 | Marine |
| 2014/0005118 A1 | 1/2014 | Verdine et al. |
| 2014/0011979 A1 | 1/2014 | Verdine et al. |
| 2014/0018302 A1 | 1/2014 | Walensky et al. |
| 2014/0135473 A1 | 5/2014 | Nash |

FOREIGN PATENT DOCUMENTS

| | | |
|---|---|---|
| EP | 0552417 A1 | 7/1993 |
| EP | 0643726 B1 | 8/1999 |

(56) References Cited

FOREIGN PATENT DOCUMENTS

| | | |
|---|---|---|
| EP | 0977580 B1 | 4/2003 |
| EP | 1321474 A1 | 6/2003 |
| EP | 1609802 A1 | 12/2005 |
| EP | 1243923 B1 | 3/2006 |
| EP | 1180016 B1 | 9/2006 |
| EP | 0958305 B1 | 6/2008 |
| EP | 2377849 A2 | 10/2011 |
| JP | 2002-524391 | 8/2002 |
| JP | 2010/120881 A | 6/2010 |
| WO | WO 92/06998 A1 | 4/1992 |
| WO | WO 93/07170 A1 | 4/1993 |
| WO | WO 94/22910 A1 | 10/1994 |
| WO | WO 95/22546 A1 | 8/1995 |
| WO | WO 96/34878 A1 | 11/1996 |
| WO | WO 97/13537 A1 | 4/1997 |
| WO | WO 97/14794 A1 | 4/1997 |
| WO | WO 97/37705 A1 | 10/1997 |
| WO | WO 98/17625 A1 | 4/1998 |
| WO | WO 99/34850 A1 | 7/1999 |
| WO | WO 99/63929 A2 | 12/1999 |
| WO | WO 00/06187 A2 | 2/2000 |
| WO | WO 00/06187 A3 | 5/2000 |
| WO | WO 02/064790 A2 | 8/2002 |
| WO | WO 02/070547 A1 | 9/2002 |
| WO | WO 02/064790 A3 | 5/2003 |
| WO | WO 03/054000 A1 | 7/2003 |
| WO | WO 03/102538 A2 | 12/2003 |
| WO | WO 03/106491 A2 | 12/2003 |
| WO | WO 2004/041275 A1 | 5/2004 |
| WO | WO 2004/058804 A1 | 7/2004 |
| WO | WO 03/106491 A3 | 12/2004 |
| WO | WO 2005/040202 A2 | 5/2005 |
| WO | WO-2005/044839 * | 5/2005 |
| WO | WO2005/044839 | 5/2005 |
| WO | WO 2005/040202 A3 | 6/2005 |
| WO | WO 2005/074521 A2 | 8/2005 |
| WO | WO 2005/085457 A2 | 9/2005 |
| WO | WO 2005/090388 A1 | 9/2005 |
| WO | WO 2005/118620 A2 | 12/2005 |
| WO | WO 2005/118634 A2 | 12/2005 |
| WO | WO 2005/118634 A3 | 5/2006 |
| WO | WO 2005/118620 A3 | 6/2006 |
| WO | WO 2006/103666 A2 | 10/2006 |
| WO | WO 2006/103666 A3 | 3/2007 |
| WO | WO 2007/141533 A2 | 12/2007 |
| WO | WO 2008/014216 A1 | 1/2008 |
| WO | WO 2008/045238 A2 | 4/2008 |
| WO | WO 2008/061192 A2 | 5/2008 |
| WO | WO 2007/141533 A3 | 7/2008 |
| WO | WO 2008/061192 A3 | 7/2008 |
| WO | WO 2008/092281 A1 | 8/2008 |
| WO | WO 2008/095063 A1 | 8/2008 |
| WO | WO 2008/104000 A2 | 8/2008 |
| WO | WO 2008/106507 A2 | 9/2008 |
| WO | WO 2008/121767 A2 | 10/2008 |
| WO | WO 2008/121767 A3 | 1/2009 |
| WO | WO 2009/137532 A1 | 11/2009 |
| WO | WO 2010/011313 A2 | 1/2010 |
| WO | WO 2010/013011 A1 | 2/2010 |
| WO | WO 2010/058819 A1 | 5/2010 |
| WO | WO 2010/083501 A2 | 7/2010 |
| WO | WO 2010/100351 A1 | 9/2010 |
| WO | WO 2010/107485 A1 | 9/2010 |
| WO | WO 2010/011313 A3 | 12/2010 |
| WO | WO 2011/005219 A1 | 1/2011 |
| WO | WO 2011/008260 A2 | 1/2011 |
| WO | WO 2011/008260 A3 | 3/2011 |
| WO | WO 2011/023677 A1 | 3/2011 |
| WO | WO 2011/060049 A2 | 5/2011 |
| WO | WO 2011/061139 A1 | 5/2011 |
| WO | WO 2011/076786 A1 | 6/2011 |
| WO | WO 2011/090297 A2 | 7/2011 |
| WO | WO 2011/101297 A1 | 8/2011 |
| WO | WO 2011/106650 A2 | 9/2011 |
| WO | WO 2011/161699 A2 | 12/2011 |
| WO | WO 2012/016186 A1 | 2/2012 |
| WO | WO 2012/021876 A2 | 2/2012 |
| WO | WO 2012/033525 A2 | 3/2012 |
| WO | WO 2012/034954 A1 | 3/2012 |
| WO | WO 2012/038307 A1 | 3/2012 |
| WO | WO 2012/040459 A2 | 3/2012 |
| WO | WO 2012/045018 A1 | 4/2012 |
| WO | WO 2012/047587 A2 | 4/2012 |
| WO | WO 2012/051405 A1 | 4/2012 |
| WO | WO 2012/059696 A1 | 5/2012 |
| WO | WO 2012/065022 A2 | 5/2012 |
| WO | WO 2012/065181 A2 | 5/2012 |
| WO | WO 2012/066095 A1 | 5/2012 |
| WO | WO 2012/040459 A3 | 6/2012 |
| WO | WO 2012/076513 A1 | 6/2012 |
| WO | WO 2012/080389 A1 | 6/2012 |
| WO | WO 2012/083078 A2 | 6/2012 |
| WO | WO 2012/083181 A1 | 6/2012 |
| WO | WO 2012/121057 A1 | 9/2012 |
| WO | WO 2012/149563 A1 | 11/2012 |
| WO | WO 2012/174423 A1 | 12/2012 |
| WO | WO 2012/175962 A1 | 12/2012 |
| WO | WO 2013/033645 A1 | 3/2013 |
| WO | WO 2013/036208 A1 | 3/2013 |
| WO | WO 2013/049250 A1 | 4/2013 |

OTHER PUBLICATIONS

Li, et al. Systematic mutational analysis of peptide inhibition of the p53-MDM2/MDMX interactions. J Mol Biol. Apr. 30, 2010;398(2):200-13. doi: 10.1016/j.jmb.2010.03.005. Epub Mar. 10, 2010.

Pazgier, et al. Structural basis for high-affinity peptide inhibition of p53 interactions with MDM2 and MDMX. Proc Natl Acad Sci U S A. Mar. 24, 2009;106(12):4665-70. doi: 10.1073/pnas.0900947106. Epub Mar. 2, 2009.

Phan, et al. Structure-based design of high affinity peptides inhibiting the interaction of p53 with MDM2 and MDMX. J Biol Chem. Jan. 15, 2010;285(3):2174-83. doi: 10.1074/jbc.M109.073056. Epub Nov. 12, 2009.

U.S. Appl. No. 13/494,846, filed Jun. 12, 2012, Nash et al.
U.S. Appl. No. 13/767,852, filed Feb. 14, 2013, Guerlavais et al.
U.S. Appl. No. 13/767,857, filed Feb. 14, 2013, Guerlavais et al.
U.S. Appl. No. 13/816,880, filed Feb. 13, 2013, Guerlavais et al.

Andrews et al. Fomiing Stable Helical Peptide Using Natural and Artificial Amino Acids. Tetrahedron. 1999;55:11711-11743.

Annis, et al. A general technique to rank protein-ligand binding affinities and determine allosteric versus direct binding site competition in compound mixtures. J Am Chem Soc. Dec. 1, 2004;126(47):15495-503.

Annis, et al. ALIS: An Affinity Selection—Mass Spectrometry System for the Discovery and Characterization of Protein-Ligand Interactions. In: Wanner, K. and Höfner, G. eds. Mass Spectrometry in Medicinal Chemistry. Wiley-VCH; 2007:121-156.

Austin et al., "A Template for Stabilization of a Peptide α-Helix: Synthesis and Evaluation of Conformational Effects by Circular Dichroism and NMR," J. Am. Chem. Soc. 119:6461-6472 (1997).

Baell, J.B. Prospects for Targeting the Bcl-2 Family of Proteins to Develop Novel cytotoxic drugs. Biochem Pharmacol. Sep. 2002;64(5-6):851-63.

Bakhshi, et al. Cloning the chromosomal breakpoint of t(14;18) human lymphomas: clustering around JH on chromosome 14 and near a transcriptional unit on 18. Cell. Jul. 1985;41(3):899-906.

Banerji et al., "Synthesis of Cyclic β-Turn Mimics from L-Pro-Phe/Phe-L-Pro Derived Di- and Tripeptides via Ring Closing Metathesis: The Role of Chirality of the Phe Residue During Cyclization," Tetrahedron Lett. 43:6473-6477 (2002).

Bang, et al. Total chemical synthesis of crambin. J Am Chem Soc. Feb. 11, 2004;126(5):1377-83.

Bernal, et al. A stapled p53 helix overcomes HDMX-mediated suppression of p53. Cancer Cell. Nov. 16, 2010;18(5):411-22. doi: 10.1016/j.ccr.2010.10.024.

Boguslavsky, et al. Effect of peptide conformation on membrane permeability. J Pept Res. Jun. 2003;61(6):287-97.

(56) References Cited

OTHER PUBLICATIONS

Bossy-Wetzel, et al. Assays for cytochrome c release from mitochondria during apoptosis. Methods Enzymol. 2000;322:235-42.

Bossy-Wetzel, et al. Detection of apoptosis by annexin V labeling. Methods Enzymol. 2000;322:15-8.

Brunel, et al. Synthesis of constrained helical peptides by thioether ligation: application to analogs of gp41. Chem Commun (Camb). May 28, 2005;(20):2552-4. Epub Mar. 11, 2005.

Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).

Chakrabartty et al., "Helix Capping Propensities in Peptides Parallel Those in Proteins," Proc. Nat'l Acad. Sci. USA 90:11332-11336 (1993).

Chapman et al., "A Highly Stable Short α-Helix Constrained by a Main-chain Hydrogen-bond Surrogate," J. Am. Chem. Soc. 126:12252-12253 (2004).

Chapman, et al. Optimized synthesis of hydrogen-bond surrogate helices: surprising effects of microwave heating on the activity of Grubbs catalysts. Org Lett. Dec. 7, 2006;8(25):5825-8.

Chin & Schepartz, "Design and Evolution of a Miniature Bcl-2 Binding Protein," Angew. Chem. Int. Ed. 40(20):3806-3809 (2001).

Chin et al., "Circular Dichroism Spectra of Short, Fixed-nucleus Alanine Helices," Proc. Nat'l Acad. Sci. USA 99(24):15416-15421 (2002).

Chittenden, et al. A conserved domain in Bak, distinct from BH1 and BH2, mediates cell death and protein binding functions. EMBO J. Nov. 15, 1995;14(22):5589-96.

Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci U S A. Nov. 1985;82(21):7439-43.

Danial, et al. Cell death: critical control points. Cell. 2004; 116:204-219.

Degterev et al., "Identification of Small-molecule Inhibitors of Interaction between the BH3 Domain and Bcl-xL," Nature Cell Biol. 3:173-182 (2001).

Deiters, et al. Adding amino acids with novel reactivity to the genetic code of Saccharomyces cerevisiae. J. Am. Chem. Soc. Oct. 1, 2003;125(39):11782-11783.

Designing Custom Peptide. from SIGMA Genosys, pp. 1-2. Accessed Dec. 16, 2004.

Dimartino, et al. Solid-phase synthesis of hydrogen-bond surrogate-derived alpha-helices. Org Lett. Jun. 9, 2005;7(12):2389-92.

European office action dated Aug. 20, 2012 for EP Application No. 09730445.5.

European search report and search opinion dated May 6, 2011 for Application No. 10195495.6.

European search report and search opinion dated May 9, 2011 for Application No. 10195490.7.

European search report dated Nov. 7, 2008 for Application No. 8016651.5.

European search report dated Aug. 22, 2008 for Application No. 4811198.3.

Felix et al., "Synthesis, Biological Activity and Conformational Analysis of Cyclic GRF Analogs," Int. J. Pep. Protein Res. 32:441-454 (1988).

Fields, et al. Chapter 3 in Synthetic Peptides: A User's Guide. Grant W.H. Freeman & Co. New York, NY. 1992, p. 77.

Fieser, et al. Fieser and Fieser's Reagents for Organic Synthesis. John Wiley and Sons. 1994.

Fischer, et al. Apoptosis-based therapies and drug targets. Cell Death and Differentiation. 2005; 12:942-961.

Fulda, et al. Extrinsic versus intrinsic apoptosis pathways in anticancer chemotherapy. Oncogene. Aug. 7, 2006;25(34):4798-811.

Galande, et al. An effective method of on-resin disulfide bond formation in peptides. J. Comb. Chem. Mar.-Apr. 2005;7(2):174-177.

Galluzzi, et al. Guidelines for the use and interpretation of assays for monitoring cell death in higher eukaryotes. Cell Death Differ. Aug. 2009;16(8):1093-107. Epub Apr. 17, 2009.

Ghadiri & Choi, "Secondary Structure Nucleation in Peptides. Transition Metal Ion Stabilized α-Helices," J. Am. Chem. Soc. 112:1630-1632 (1990).

Greene, et al. Protective Groups in Organic Synthesis, 2nd Ed. John Wiley and Sons. 1991.

Hiroshige, et al. Palladium-mediated macrocyclisations on solid support and its applica-tions to combinatorial synthesis. J. Am. Chem. Soc. 1995; 117:11590-11591.

Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).

International search report and written opinion dated Oct. 12, 2011 for PCT/US2011/047692.

International search report and written report dated May 23, 2013 for PCT/US2013/026241.

International search report and written report dated May 29, 2013 for PCT/US2013/026238.

International search report dated Nov. 30, 2009 for PCT Application No. US2009/02225.

International search report dated May 18, 2005 for PCT Application No. US2004/38403.

Kallen, et al. Crystal structures of human MdmX(HdmX) in complex with p53 peptide analogues reveal surprising conformational changes. Journal of Biological Chemistry. Mar. 27, 2009; 284:8812-8821.

Karle, et al. Structural charateristics of alpha-helical peptide molecules containing Aib residues. Biochemistry. Jul. 24, 1990;29(29):6747-56.

Karle. Flexibility in peptide molecules and restraints imposed by hydrogen bonds, the Aib residue, and core inserts. Biopolymers. 1996;40(1):157-80.

Kelso et al., "A Cyclic Metallopeptide Induces α Helicity in Short Peptide Fragments of Thermolysin," Angew. Chem. Int. Ed. 42(4):421-424 (2003).

Kelso et al., "α-Turn Mimetics: Short Peptide α-Helices Composed of Cyclic Metallopentapeptide Modules," J. Am. Chem. Soc. 126:4828-4842 (2004).

Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac—Hel1—OH)," J. Org. Chem. 56:6672-6682 (1991).

Kent. Advanced Biology. Oxford University Press. 2000.

Kilby et al., "Potent Suppression of HIV-1 Replication in Humans by T-20, a Peptide Inhibitor of gp41-Mediated Virus Entry," Nat. Med. 4(11):1302-1307 (1998).

Kritzer et al., "Helical β-Peptide Inhibitors of the p53—hDM2 Interaction," J. Am. Chem. Soc. 126:9468-9469 (2004).

Kutzki et al., "Development of a Potent Bcl-xL Antagonist Based on α-Helix Mimicry," J. Am. Chem. Soc. 124:11838-11839 (2002).

Kwon, et al. Quantitative comparison of the relative cell permeability of cyclic and linear peptides. Chem Biol. Jun. 2007;14(6):671-7.

Larock. Comprehensive Organic Transformations. VCH Publishers. 1989.

Lee, et al. A novel BH3 ligand that selectively targets Mcl-1 reveals that apoptosis can proceed without Mcl-1 degradation. J Cell Biol. Jan. 28, 2008;180(2):341-355.

Li, et al. A convenient preparation of 5-iodo-1,4-disubstituted-1,2,3-triazole: multicomponent one-pot reaction of azide and alkyne mediated by CuI-NBS. J Org Chem. May 2, 2008;73(9):3630-3. doi: 10.1021/jo800035v. Epub Mar. 22, 2008.

Litowski & Hodges, "Designing Heterodimeric Two-stranded α-Helical Coiled-coils: Effects of Hydrophobicity and α-Helical Propensity on Protein Folding, Stability, and Specificity," J. Biol. Chem. 277(40):37272-37279 (2002).

Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.

(56) References Cited

OTHER PUBLICATIONS

Lyu & Wemmer, "Capping Interactions in Isolated α Helices: Position-dependent Substitution Effects and Structure of a Serine-capped Peptide Helix," Biochemistry 32:421-425 (1993).

Lyu et al, "α-Helix Stabilization by Natural and Unnatural Amino Acids with Alkyl Side Chains," Proc. Nat'l Acad. Sci. USA 88:5317-5320 (1991).

Mai et al. A proapoptotic peptide for the treatment of solid tumors Cancer Res. Nov. 1, 2001;61(21):7709-12.

Mannhold, R., Kubinyi, H., Folkers, G., series eds. Molecular Drug Properties: Measurement and Prediction (Methods and Principles in Medicinal Chemistry). Wiley-VCH; 2007.

McGahon, et al. The end of the (cell) line: methods for the study of apoptosis in vitro. Methods Cell Biol. 1995;46:153-85.

Mosberg, et al. Dithioeter-containing cyclic peptides. J. Am. Chem. Soc. 1985;107(10):2986-2987.

Muchmore, et al. X-ray and NMR structure of human Bcl-xL, an inhibitor of programmed cell death. Nature. May 23, 1996;381(6580):335-41.

Mustapa, et al. Synthesis of a cyclic peptide containing norlanthionine: effect of the thioether bridge on peptide conformation. J Org Chem. Oct. 17, 2003;68(21):8193-8.

Nelson & Kallenbach, "Persistence of the α-Helix Stop Signal in the S-Peptide in Trifluoroethanol Solutions," Biochemistry 28:5256-5261 (1989).

Non-Final Office Action dated Dec. 5, 2008 from U.S. Appl. No. 10/981,873.

O'Neil & DeGrado, "A Thermodynamic Scale for the Helix-forming Tendencies of the Commonly Occurring Amino Acids," Science 250:646-651(1990).

Office action dated Jan. 26, 2009 for U.S. Appl. No. 11/148,976.
Office Action dated Jan. 30, 2008 for U.S. Appl. No. 10/981,873.
Office action dated Feb. 9, 2012 for U.S. Appl. No. 12/420,816.
Office action dated Mar. 22, 2013 for U.S. Appl. No. 12/233,555.
Office action dated Apr. 18, 2011 for U.S. Appl. No. 12/182,673.
Office action dated Jun. 28, 2012 for U.S. Appl. No. 12/233,555.
Office action dated Jul. 15, 2013 for U.S. Appl. No. 13/570,146.
Office action dated Aug. 9, 2010 for U.S. Appl. No. 12/182,673.
Office action dated Oct. 18, 2011 for U.S. Appl. No. 12/796,212.
Office action dated Nov. 5, 2002 for U.S. Appl. No. 09/574,086.
Office action dated Nov. 25, 2009 for U.S. Appl. No. 11/148,976.
Office action dated Dec. 29, 2011 for U.S. Appl. No. 12/233,555.

Or et al. Cysteine alkylation in unprotected peptides: synthesis of a carbavasopressin analogue by intramolecular cystein alkylation. J. Org. Chem. Apr. 1991;56(9):3146-3149.

Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).

Paquette. Encyclopedia of Reagents for Organic Synthesis. John Wiley and Sons. 1995.

Peryshkov, et al. Z-Selective olefin metathesis reactions promoted by tungsten oxo alkylidene complexes. J Am Chem Soc. Dec. 28, 2011;133(51):20754-7. doi: 10.1021/ja210349m. Epub Nov. 30, 2011.

Phan, et al. Structure-based design of high affinity peptides inhibiting the interaction of p53 with MDM2 and MDMX. J Biol Chem. Jan. 15, 2010;285(3):2174-83. doi: 10.7074/jbc.M109.073056. Epub Nov. 12, 2009.

Phelan, et al. A General Method for Constraining Short Peptides to an α-Helical Conformation. J. Am. Chem. Soc. 1997;119:455-460.

Punna, et al. Head-to-tail peptide cyclodimerization by copper-catalyzed azide-alkyne cycloaddition. Angew Chem Int Ed Engl. Apr. 8, 2005;44(15):2215-20.

Rasmussen, et al. Ruthenium-catalyzed cycloaddition of aryl azides and alkynes. Org. Lett. Dec. 20, 2007;9(26):5337-5339.

Roberts, et al. Efficient synthesis of thioether-based cyclic peptide libraries. Tetrahedon Letters. 1998; 39: 8357-8360.

Roberts, et al. Examination of methodology for the synthesis of cyclic thioether peptide libraries derived from linear tripeptides. J Pept Sci. Dec. 2007;13(12):811-21.

Rostovtsev, et al. A stepwise huisgen cycloaddition process: copper (i)-catalyzed regioselective "ligation" of azides and terminal alkynes. Angew. Chem. Int. Ed. Engl. Jul. 15, 2002;41(14):2596-2599.

Ruan et al., "Metal Ion Enhanced Helicity in Synthetic Peptides Containing Unnatural, Metal-ligating Residues," J. Am. Chem. Soc. 112:9403-9404 (1990).

Ruffolo and Shore. BCL-2 Selectively Interacts with the BID-Induced Open Conformer of BAK, Inhibiting BAK Auto-Oligomerization. J. Biol. Chern. 2003;278(27):25039-25045.

Sanchez-Garcia, et al. Tumorigenic activity of the BCR-ABL oncogenes is mediated by BCL2. Proc Natl Acad Sci U S A. Jun. 6, 1995;92(12):5287-91.

Scorrano, et al. A distinct pathway remodels mitochondrial cristae and mobilizes cytochrome c during apoptosis. Dev Cell. Jan. 2002;2(1):55-67.

Seebach, et al. Self-Regeneration of Stereocenters (SRS)—Applications, Limitations, and Abandonment of a Synthetic Principle. Angew. Chem. Int. Ed. Engl. 1996;35:2708-2748.

Shepherd et al., "Single Turn Peptide Alpha Helices with Exceptional Stability in Water," J. Am. Chem. Soc. 127:2974-2983 (2005).

Sia et al., "Short Constrained Peptides that Inhibit HIV-1 Entry," Proc. Nat'l Acad. Sci. USA 99(23):14664-14669 (2002).

Spierings, et al. Connected to death: the (unexpurgated) mitochondrial pathway of apoptosis. Science. 2005; 310:66-67.

Stewart, et al. Cell-penetrating peptides as delivery vehicles for biology and medicine. Org Biomol Chem. Jul. 7, 2008;6(13):2242-55. doi: 10.1039/b719950c. Epub Apr. 15, 2008.

Suzuki, et al. Structure of Bax: coregulation of dimer formation and intracellular localization. Cell. Nov. 10, 2000;103(4):645-54.

Szewczuk, et al. Synthesis and biological activity of new conformationally restricted analogues of pepstatin. Int. J. Pept. Protein Res. Sep.-Oct. 1992;40(3-4):233-42.

Taylor. The synthesis and study of side-chain lactam-bridged peptides. Biopolymers. 2002;66(1):49-75.

Titus, et al. Human K/natural killer cells targeted with hetero-cross-linked antibodies specifically lyse tumor cells in vitro and prevent tumor growth in vivo. J Immunol. Nov. 1, 1987;139(9):3153-8.

Trnka & Grubbs, "The Development of L2X2Ru=CHR Olefin Metathesis Catalysts: An Organometallic Success Story," Acc. Chem. Res. 34:18-29 (2001).

Tugyi, et al. The effect of cyclization on the enzymatic degradation of herpes simplex virus glycoprotein D derived epitope peptide. J Pept Sci. Oct. 2005;11(10):642-9.

Tyndall et al. Macrocycles mimic the extended peptide conformation recognized by aspartic, serine, cysteine and metallo proteases. Curr Med Chem. Jul. 2001;8(8):893-907.

Viallet, et al. Tallimustine is inactive in patients with previously treated small cell lung cancer. A phase II trial of the National Cancer Institute of Canada Clinical Trials Group. Lung Cancer. Nov. 1996;15(3):367-73.

Wang et al. Cell permeable Bcl-2 binding peptides: a chemical approach to apoptosis induction in tumor cells. Cancer Res. Mar. 15, 2000;60(6):1498-502.

Wang et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.

Wang, et al. BID: a novel BH3 domain-only death agonist. Genes Dev. Nov. 15, 1996;10(22):2859-69.

Wang, et al. Evaluation of biologically relevant short alpha-helices stabilized by a main-chain hydrogen-bond surrogate. J Am Chem Soc. Jul. 19, 2006;128(28):9248-56.

Wang, et al. Nucleation and stability of hydrogen-bond surrogate-based alpha-helices. Org Biomol Chem. Nov. 21, 2006;4(22):4074-81.

Wei, et al. tBID, a membrane-targeted death ligand, oligomerizes BAK to release cytochrome c. Genes Dev. Aug. 15, 2000;14(16):2060-71.

(56) References Cited

OTHER PUBLICATIONS

Wild et al., "Peptides Corresponding to a Predictive α-Helical Domain of Human Immunodeficiency Virus Type 1 gp41 are Potent Inhibitors of Virus Infection," Proc. Nat'l Acad. Sci. USA 91:9770-9774 (1994).
Wu, et al. Regiospecific Synthesis of 1,4,5-Trisubstituted-1,2,3-triazole via One-Pot Reaction Promoted by Copper(I) Salt. Synthesis. 2005(8): 1314-1318.
Yang, et al. Calculation of protein conformation from circular dichroism. Methods Enzymol. 1986;130:208-69.
Yu, et al. Synthesis of macrocyclic natural products by catalyst-controlled stereoselective ring-closing metathesis. Nature. Nov. 2, 2011;479(7371):88-93. doi: 10.1038/nature10563.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. 310 Helix versus alpha-helix: a molecular dynamics study of conformational preferences of Aib and Alanine. J. American Cancer Society. Dec. 1994; 116(26):11915-11921.
Zhang, et al. Ruthenium-catalyzed cycloaddition of alkynes and organic azides. J. Am. Chem. Soc. Nov. 23, 2005;127(46):15998-9.
U.S. Appl. No. 13/680,905, filed Nov. 19, 2012, Verdine et al.
Agola et al., Rab GTPases as regulators of endocytosis, targets of disease and therapeutic opportunities. Clin Genet. Oct. 2011; 80(4): 305-318.
Altschul et al., Basic local alignment search tool. J Mol Biol. Oct. 5, 1990;215(3):403-10.
Blundell et al., Atomic positions in rhombohedral 2-zinc insulin crystals. Nature. Jun. 25, 1971;231(5304):506-11.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Carillo et al., The Multiple Sequence Alignment Problem in Biology. SIAM J Applied Math. 1988;48:1073-82.
Carlson et al., Specificity landscapes of DNA binding molecules elucidate biological function. Proc Natl Acad Sci USA. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Chia et al., Emerging roles for Rab family GTPases in human cancer. Biochim Biophys Acta. Apr. 2009;1795(2):110-6.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor—I receptor binding and negative co-operativity, and its relevance to mitogenic versus metabolic signalling. Diabetologia. Sep. 1994;37 Suppl 2:S135-48.
Devereux et al., A comprehensive set of sequence analysis programs for the VAX. Nucleic Acids Res. Jan. 11, 1984;12(1 Pt 1):387-95.
Evans et al., The Rise of Azide—Alkyne 1,3-Dipolar 'Click' Cycloaddition and its Application to Polymer Science and Surface Modification. Australian Journal of Chemistry. 2007;60:384-95.
Fisher et al., Myc/Max and other helix-loop-helix/leucine zipper proteins bend DNA toward the minor groove. Proc Natl Acad Sci U S A. Dec. 15, 1992;89(24):11779-83.
Harris et al., Synthesis of proline-modified analogues of the neuroprotective agent glycyl-lprolyl-glutamic acid (GPE). Tetrahedron. 2005;61:10018-35.
Hellman et al., Electrophoretic mobility shift assay (EMSA) for detecting protein-nucleic acid interactions. Nat Protoc. 2007;2(8):1849-61.

Huang et al., How insulin binds: the B-chain alpha-helix contacts the L1 beta-helix of the insulin receptor. J Mol Biol. Aug. 6, 2004;341(2):529-50.
International Search Report and Written Opinion for PCT/US2012/042738, mailed Oct. 18, 2012 (H0824.70100W000).
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Junutula et al., Molecular characterization of Rab11 interactions with members of the family of Rab 11-interacting proteins. J Biol Chem. Aug. 6, 2004;279(32):33430-7. Epub Jun. 1, 2004.
Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.
Luscher et al., The basic region/helix-loop-helix/leucine zipper domain of Myc protooncoproteins: function and regulation. Oncogene. May 13, 1999;18(19):2955-66.
Marshall et al., Back to the future: ribonuclease A. Biopolymers. 2008;90(3):259-77.
McKern et al., Structure of the insulin receptor ectodomain reveals a folded-over conformation. Nature. Sep. 14, 2006;443(7108):218-21. Epub Sep. 6, 2006.
Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.
Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.
Mynarcik et al., Alanine-scanning mutagenesis of a C-terminal ligand binding domain of the insulin receptor alpha subunit. J Biol Chem. Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Notice of Allowance, mailed Aug. 6, 2012, in U.S. Appl. No. 12/796,212.
Pillutla et al., Peptides identify the critical hotspots involved in the biological activation of the insulin receptor. J Biol Chem. Jun. 21, 2002;277(25):22590-4. Epub Apr. 18, 2002.
Schaffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schaffer et al., Assembly of high-affinity insulin receptor agonists and antagonists from peptide building blocks. Proc Natl Acad Sci U S A. Apr. 15, 2003;100(8):4435-9. Epub Apr. 8, 2003.

(56) References Cited

OTHER PUBLICATIONS

Seabra et al., Rab GTPases, intracellular traffic and disease. Trends Mol Med. Jan. 2002;8(1):23-30.
Shiba et al., Structural basis for Rab11-dependent membrane recruitment of a family of Rab11interacting protein 3 (FIP3)/Arfophilin-1. Proc Natl Acad Sci U S A. Oct. 17, 2006;103(42):15416-21. Epub Oct. 9, 2006.
Siddle et al., Specificity in ligand binding and intracellular signalling by insulin and insulin-like growth factor receptors. Biochem Soc Trans. Aug. 2001;29(Pt 4):513-25.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Tornoe et al., Peptidotriazoles on solid phase: [1,2,3]-triazoles by regiospecific copper(i)catalyzed 1,3-dipolar cycloadditions of terminal alkynes to azides. J Org Chem. May 3, 2002;67(9):3057-64.
Wang, 4-Alkyl-2-trichloromethyloxazolidin-5-ones: Valuable Precursors to Enantiomerically Pure C- and N-Protected a-Alkyl Prolines. Synlett. 1999;1:33-36.
Wei et al., Disorder and structure in the Rab11 binding domain of Rab11 family interacting protein 2. Biochemistry. Jan. 27, 2009;48(3):549-57. doi: 10.1021/bi8020197.
Wilen, Tables of Resolving Agents and Optical Resolutions. E.L. Eliel, ed. Universtify of Notre Dame Press, Notre Dame, IN. 1972:268-98.
Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.
Zimm et al., Theory of the Phase Transition between Helix and Random Coil in Polypeptide Chains. J Chem Phys. 1959;31:526-35.
Bernal, et al. Reactivation of the p53 tumor suppressor pathway by a stapled p53 peptide. J Am Chem Soc. Mar. 7, 2007;129(9):2456-7.
Picksley, et al. Immunochemical analysis of the interaction of p53 with MDM2;—fine mapping of the MDM2 binding site on p53 using synthetic peptides. Oncogene. Sep. 1994;9(9):2523-9.
Uesugi, et al. The alpha-helical FXXPhiPhi motif in p53: TAF interaction and discrimination by MDM2. Proc Natl Acad Sci U S A. Dec. 21, 1999;96(26):14801-6.
Walensky, et al. A stapled BID BH3 helix directly binds and activates BAX. Mol Cell. Oct. 20, 2006;24(2):199-210.
Walensky, et al. Activation of apoptosis in vivo by a hydrocarbon-stapled BH3 helix. Science. Sep. 3, 2004;305(5689):1466-70.
[No Author Listed] Designing Custom Peptide. from SIGMA Genosys, pp. 1-2. Accessed Jul. 27, 2012.
Berendsen et al., A glimpse of the Holy Grail? Science. Oct. 23, 1998;282(5389):642-3.
Bradley et al., Limits of cooperativity in a structurally modular protein: response of the Notch ankyrin domain to analogous alanine substitutions in each repeat. J Mol Biol. Nov. 22, 2002;324(2):373-86.
European search report and opinion dated Jul. 20, 2012 for EP Application No. 12159110.1.
European search report and opinion dated Sep. 27, 2012 for EP Application No. 12159110.1.
Greenlee et al., A General Synthesis of a-vinyl-a-amino acids. Tetrahedron Letters. 1978;42:3999-40002.
International Preliminary Report on Patentability for PCT/US2010/001952, Jan. 26, 2012 (H0824.70004W000).
International Search Report and Written Opinion for PCT/US2011/052755, mailed Apr. 25, 2012 (H0824.70085W000).
Invitation to Pay Additional Fees for PCT/US2011/052755 mailed Feb. 16, 2012 (H0824.70085W000).
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846last accessed Apr. 9, 2012. Abstract only. 2 pages.
Kazmaier, Sythesis of Quaternary Amino Acids Containing 3, y- as well as 7,6-Unsaturated Side Chains via Chelate-Enolate Claisen Rearrangement. Tetrahedron Letters. 1996;37(30):5351-4.
McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94.
Ngo et al., Computational complexity, protein structure prediction, and the levinthal paradox. In: The Protein Folding Problem and Tertiary Structure Prediction. K. Mem, Jr., et al. Eds. 1994:433506.
Office action dated Jan. 3, 2013 for U.S. Appl. No. 12/593,384.
Office Communication, mailed Feb. 9, 2012, for U.S. Appl. No. 12/420,816.
Office Communication, mailed Oct. 18, 2011, for U.S. Appl. No. 12/796,212.
Rudinger, Characteristics of the amino acids as components of a peptide hormone sequence. In: Peptide Hormones. J. A. Parsons, ed. University Park Press. Jun. 1976:1-7.
Schinzel et al., The phosphate recognition site of *Escherichia coli* maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Tanaka, Design and synthesis of non-proteinogenic amino acids and secondary structures of their peptides. Yakugaku Zasshi. Oct. 2006:126(10):931-44. Japanese.
Voet et al., Biochemistry. Second Edition. John Wiley & Sons, Inc. 1995:235-241.
Office action dated Sep. 18, 2013 for U.S. Appl. No. 13/767,857.
Office action dated Sep. 23, 2013 for U.S. Appl. No. 13/680,905.
Office action dated Oct. 10, 2013 for U.S. Appl. No. 13/816,880.
U.S. Appl. No. 12/905,072, filed Oct. 14, 2010, Nash et al.
U.S. Appl. No. 13/097,930, filed Apr. 29, 2011, Nash.
U.S. Appl. No. 13/250,344, filed Sep. 30, 2011, Arora et al.
U.S. Appl. No. 13/252,751, filed Oct. 4, 2011, Walensky et al.
U.S. Appl. No. 13/366,113, filed Feb. 3, 2012, Nash et al.
U.S. Appl. No. 13/370,570, filed Feb. 9, 2012, Nash et al.
U.S. Appl. No. 61/385,405, filed Sep. 22, 2010, Verdine et al.
Adhikary, et al. Transcriptional regulation and transformation by Myc proteins. Nat Rev Mol Cell Biol. Aug. 2005;6(8):635-45.
Aman, et al. cDNA cloning and characterization of the human interleukin 13 receptor alpha chain. J Biol Chem. Nov. 15, 1996;271(46):29265-70.
Andrews, et al. Forming Stable Helical Peptides Using Natural and Artificial Amino Acids. Tetrahedron 55:11711-11743 (1999).
Andrews, et al. Kinetic analysis of the interleukin-13 receptor complex. J Biol Chem. Nov. 29, 2002;277(48):46073-8.
Armstrong, et al. X=Y-ZH Systems as potential 1,3-dipoles. 5. Intramolecular cycloadditions of imines of a-amino acid esters. Tetrahedron. 1985;41(17):3547-58.
Attisano, et al. TGFbeta and Wnt pathway cross-talk. Cancer Metastasis Rev. Jan.-Jun. 2004;23(1-2):53-61.
Babine, et al. Molecular Recognition of Proteinminus signLigand Complexes: Applications to Drug Design. Chem Rev. Aug. 5, 1997;97(5):1359-1472.
Banerjee, et al. Structure of a DNA glycosylase searching for lesions. Science. Feb. 24, 2006;311(5764):1153-7.

(56) References Cited

OTHER PUBLICATIONS

Banerjee, et al. Structure of a repair enzyme interrogating undamaged DNA elucidates recognition of damaged Dna. Nature. Mar. 31, 2005;434(7033):612-8.
Bang, et al. Total chemical synthesis of crambin. J Am Chem Soc. 2004; 126(5):1377-83.
Barandon, et al. Reduction of infarct size and prevention of cardiac rupture in transgenic mice overexpressing FrzA. Circulation. Nov. 4, 2003;108(18):2282-9. Epub Oct. 27, 2003.
Barker, et al. Mining the Wnt pathway for cancer therapeutics. Nat Rev Drug Discov. Dec. 2006;5(12):997-1014.
Beloken, et al. Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon, et al. Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998; 9:4249-52.
Bennett, et al. Regulation of osteoblastogenesis and bone mass by Wntl Ob. Proc Natl Acad Sci U S A. Mar. 1, 2005;102(9):3324-9.. Epub Feb. 22, 2005.
Berge, et al. Pharmaceutical salts. J Pharm Sci. Jan. 1977;66(1):1-19.
Biagini, et al. Cross-metathesis of Unsaturated a-amino Acid Derivatives. J Chem Soc Perkin Trans. 1998;1:2485-99.
Bierzynski, et al. A salt bridge stabilizes the helix formed by isolated C-peptide of RNase A. Proc Natl Acad Sci U S A. Apr. 1982;79(8):2470-4.
Blackwell, et al. Highly efficient synthesis of covalently cross-linked peptide helices by ring-closing metathesis. Angew Chem Int Ed. 1994; 37(23):3281-84.
Blackwell, et al. Ring-closing metathesis of olefinic peptides: design, synthesis, and structural characterization of macrocyclic helical peptides. J Org Chem. Aug. 10, 2001;66(16):5291-302.
Bode, et al. Chemoselective amide ligations by decarboxylative condensations of N-alkylhydroxylamines and alpha-ketoacids. Angew Chem Int Ed Engl. Feb. 13, 2006;45(8):1248-52.
Boyden, et al. High bone density due to a mutation in LDL-receptor-related protein 5. N Engl J Med. May 16, 2002;346(20):1513-21.
Bracken, et al. Synthesis and nuclear magnetic resonance structure determination of an alpha-helical, bicyclic, lactam-bridged hexpeptide. J Am Chem Soc. 1994; 116:6431-32.
Brubaker, et al. Solution structure of the interacting domains of the Mad-Sin3 complex: implications for recruitment of a chromatin-modifying complex. Cell. Nov. 10, 2000;103(4):655-65.
Brusselle, et al. Allergen-induced airway inflammation and bronchial responsiveness in wild-type and interleukin-4-deficient mice. Am J Respir Cell Mol Biol. Mar. 1995;12(3):254-9.
Burger, et al. Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Caricasole, et al. The Wnt pathway, cell-cycle activation and beta-amyloid: novel therapeutic strategies in Alzheimer's disease? Trends Pharmacol Sci. May 2003;24(5):233-8.
Chen, et al. Small molecule-mediated disruption of Wnt-dependent signaling in tissue regeneration and cancer.. Nat Chem Biol. Feb. 2009;5(2):100-7. Epub Jan. 4, 2009.
Cheon, et al. beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chiaramonte, et al. Studies of murine schistosomiasis reveal interleukin-13 blockade as a treatment for established and progressive liver fibrosis. Hepatology. Aug. 2001;34(2):273-82.
Christodoulides, et al. WNT10B mutations in human obesity. Diabetologia. Apr. 2006;49(4):678-84. Epub Feb. 14, 2006.
Clark, et al. Supramolecular Design by Covalent Capture. Design of a Peptide Cylinder via Hydrogen-Bond-Promoted Intermolecular Olefin Metathesis. J Am Chem Soc. 1995;117:12364-65.
Clevers. Wnt/beta-catenin signaling in development and disease. Cell. Nov. 3, 2006;127(3):469-80.
Cohn, et al. IL-4-independent induction of airway hyperresponsiveness by Th2, but not Th1, cells. J Immunol. Oct. 15, 1998;161(8):3813-6.
Cole, et al. Transcription-independent functions of MYC: regulation of translation and DNA replication. Nat Rev Mol Cell Biol. Oct. 2008;9(10):810-5.
Cong, et al. A protein knockdown strategy to study the function of beta-catenin in tumorigenesis. BMC Mol Biol. Sep. 29, 2003;4:10.
Cossu, et al. Wnt signaling and the activation of myogenesis in mammals. EMBO J. Dec. 15, 1999;18(24):6867-72.
Cusack, et al. 2,4,6-Tri-isopropylbenzenesulphonyl Hydrazide: A Convenient Source of Di-imide. Tetrahedron. 1976;32:2157-62.
Dawson, et al. Synthesis of proteins by native chemical ligation. Science. Nov. 4, 1994;266(5186):776-9.
De Guzman, et al. Structural basis for cooperative transcription factor binding to the CBP coactivator. J Mol Biol. Feb. 3, 2006;355(5):1005-13.
Debinski, et al. Retargeting interleukin 13 for radioimmunodetection and radioimmunotherapy of human high-grade gliomas. Clin Cancer Res. Oct. 1999;5(10 Suppl):3143s-3147s.
Denmark, et al. Cyclopropanation with Diazomethane and Bis(oxazoline)palladium(II) Complexes. J Org Chem. May 16, 1997;62(10):3375-3389.
Doron, et al. Probiotics: their role in the treatment and prevention of disease. Expert Rev Anti Infect Ther. Apr. 2006;4(2):261-75.
Eisenmesser, et al. Solution structure of interleukin-13 and insights into receptor engagement. J Mol Biol. Jun. 29, 2001;310(1):231-41.
Ellis, et al. Design, synthesis, and evaluation of a new generation of modular nucleophilic glycine equivalents for the efficient synthesis of sterically constrained alpha-amino acids. J Org Chem. Oct. 27, 2006;71(22):8572-8.
Erlanson, et al. The leucine zipper domain controls the orientation of AP-1 in the NFAT.AP-1.DNA complex. Chem Biol. Dec. 1996;3(12):981-91.
Favrin, et al. Two-state folding over a weak free-energy barrier. Biophys J. Sep. 2003;85(3):1457-65.
Fischback, et al. Specific biochemical inactivation of oncogenic Ras proteins by nucleoside diphosphate kinase. Cancer Res. Jul. 15, 2003;63(14):4089-94.
Fischer, et al. The HIV-1 Rev activation domain is a nuclear export signal that accesses an export pathway used by specific cellular RNAs. Cell. Aug. 11, 1995;82(3):475-83.
Formaggio, et al. Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Fromme, et al. Structural basis for removal of adenine mispaired with 8-oxoguanine by MutY adenine DNA glycosylase. Nature. Feb. 12, 2004;427(6975):652-6.
Fuchs, et al. Socializing with the neighbors: stem cells and their niche. Cell. Mar. 19, 2004;116(6):769-78.
Furstner, et al. Alkyne metathesis: development of a novel molybdenum-based catalyst system and its application to the total synthesis of epothilone A and C. Chemistry. Dec. 17, 2001;7(24):5299-317.
Furstner, et al. Mo[N(t-Bu)(AR)]3 Complexes as catalyst precursors: In situ activation and application to metathesis reactions of alkynes and diynes. J Am chem Soc. 1999; 121:9453-54.
Furstner, et al. Nozaki-Hiyama-Kishi reactions catalytic in chromium. J Am Chem Soc. 1996; 118:12349-57.
Gallivan, et al. A neutral, water-soluble olefin metathesis catalyst based on an N-heterocyclic carbene ligand. Tetrahedron Letters. 2005; 46:2577-80.
Gante. Peptidomimetics—Tailored enzyme inhibitors. J Angew Chem Int Ed Engl. 1994; 33:1699-1720.
Gat, et al. De Novo hair follicle morphogenesis and hair tumors in mice expressing a truncated beta-catenin in skin. Cell. Nov. 25, 1998;95(5):605-14.
Gavathiotis, et al. BAX activation is initiated at a novel interaction site. Nature. Oct. 23, 2008;455(7216):1076-81.
Gerber-Lemaire, et al. Glycosylation pathways as drug targets for cancer: glycosidase inhibitors. Mini Rev Med Chem. Sep. 2006;6(9):1043-52.

(56) References Cited

OTHER PUBLICATIONS

Giannis, et al. Peptidomimetics for receptor ligands—Discovery, development, and medical perspectives. Angew Chem Int Ed Engl. 1993; 32:1244-67.
Gong, et al. LDL receptor-related protein 5 (LRP5) affects bone accrual and eye development. Cell. Nov. 16, 2001;107(4):513-23.
Goodson, et al. Potential Growth Antagonists. I. Hydantoins and Disubstituted Glycines. J Org Chem. 1960;25:1920-24.
Gorlich, et al. Transport between the cell nucleus and the cytoplasm. Annu Rev Cell Dev Biol. 1999; 15:607-60.
Goun, et al. Molecular transporters: synthesis of oligoguanidinium transporters and their application to drug delivery and real-time imaging. Chembiochem. Oct. 2006;7(10):1497-515.
Greenfield, et al. Computed circular dichroism spectra for the evaluation of protein conformation. Biochemistry. Oct. 1969;8(10):4108-16.
Grubbs, et al. Ring-closing metathesis and related processes in organic synthesis. Acc Chem Res. 1995; 28:446-52.
Grunig, et al. Requirement for IL-13 independently of IL-4 in experimental asthma. Science. Dec. 18, 1998;282(5397):2261-3.
Guinn, et al. Synthesis and characterization of polyamides containing unnatural amino acids. Biopolymers. May 1995;35(5):503-12.
Harper, et al. Efficacy of a bivalent L1 virus-like particle vaccine in prevention of infection with human papillomavirus types 16 and 18 in young women: a randomised controlled trial. Lancet. Nov. 13-19, 2004;364(9447):1757-65.
Hartmann, et al. Dual roles of Wnt signaling during chondrogenesis in the chicken limb. Development. Jul. 2000;127(14):3141-59.
Hartmann. A Wnt canon orchestrating osteoblastogenesis. Trends Cell Biol. Mar. 2006;16(3):151-8. Epub Feb. 7, 2006.
Henchey, et al. Contemporary strategies for the stabilization of peptides in the a-helical conformation. Curr Opin Chem Biol. 2008;12:692-97.
Hipfner, et al. Connecting proliferation and apoptosis in development and disease. Nat Rev Mol Cell Biol. Oct. 2004;5(10):805-15.
Hoang, et al. Dickkopf 3 inhibits invasion and motility of Saos-2 osteosarcoma cells by modulating the Wnt-beta-catenin pathway. Cancer Res. Apr. 15, 2004;64(8):2734-9.
Holford, et al. Adding 'splice' to protein engineering. Structure. Aug. 15, 1998;6(8):951-6.
Huang, et al. Tankyrase inhibition stabilizes axin and antagonizes Wnt signalling. Nature. Oct. 1, 2009;461(7264):614-20. Epub Sep. 16, 2009.
International preliminary report on patentability dated Feb. 3, 2011 for PCT/US2009/004260.
International preliminary report on patentability dated Oct. 8, 2009 for PCT/US2008/058575.
International search report and written opinion dated Feb. 2, 2011 for PCT/US2010/001952.
International search report and written opinion dated Oct. 15, 2010 for PCT/US2009/004260.
International search report dated Nov. 17, 2008 for PCT/US2008/058575.
Invitation to pay additional fees dated Mar. 19, 2010 for PCT/US2010/004260.
Invitation to pay additional fees dated Oct. 29, 2010 for PCT/US2010/001952.
Jackson, et al. General Approach to the Synthesis of Short a-Helical Peptides. J Am Chem Soc. 1991;113:9391-93.
Jamieson, et al. Granulocyte-macrophage progenitors as candidate leukemic stem cells in blast-crisis CML. N Engl J Med. Aug. 12, 2004;351(7):657-67.
Jordan, et al. Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Karwoski, et al. Lysinonorleucine cross-link formation in alpha amino heptenoic acid-substituted peptide derivatives. Biopolymers. 1978;17(5):1119-27.

Katoh, et al. Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.
Katsu, et al. The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul, et al. Stereochemical control of peptide folding. Bioorg Med Chem. Jan. 1999;7(1):105-17.
Kelly-Welch, et al. Interleukin-4 and interleukin-13 signaling connections maps. Science. Jun. 6, 2003;300(5625):1527-8.
Kim, et al. Stereochemical effects of all-hydrocarbon tethers in i,i+4 stapled peptides. Bioorg Med Chem Lett. May 1, 2009;19(9):2533-6.
Kimmerlin, et al. '100 years of peptide synthesis': ligation methods for peptide and protein synthesis with applications to beta-peptide assemblies. J Pept Res. Feb. 2005;65(2):229-60.
Kinzler, et al. Identification of FAP locus genes from chromosome 5q21. Science. Aug. 9, 1991;253(5020):661-5.
Kinzler, et al. Lessons from hereditary colorectal cancer. Cell. Oct. 18, 1996;87(2):159-70.
Knackmuss, et al. Specific inhibition of interleukin-13 activity by a recombinant human single-chain immunoglobulin domain directed against the IL-13 receptor alpha1 chain. Biol Chem. Mar. 2007;388(3):325-30.
Kondo, et al. Frizzled 4 gene (FZD4) mutations in patients with familial exudative vitreoretinopathy with variable expressivity. Br J Ophthalmol. Oct. 2003;87(10):1291-5.
Korcsmaros, et al. Uniformly curated signaling pathways reveal tissue-specific cross-talks and support drug target discovery. Bioinformatics. Aug. 15, 2010;26(16):2042-50. Epub Jun. 11, 2010.
Korinek, et al. Depletion of epithelial stem-cell compartments in the small intestine of mice lacking Tcf-4. Nat Genet. Aug. 1998;19(4):379-83.
Kotha, et al. Modification of constrained peptides by ring-closing metathesis reaction. Bioorg Med Chem Lett. Jun. 4, 2001;11(11):1421-3.
Kouzarides, et al. Acetylation: a regulatory modification to rival phosphorylation? EMBO J. Mar. 15, 2000;19(6):1176-9.
Kozlovsky, et al. GSK-3 and the neurodevelopmental hypothesis of schizophrenia. Eur Neuropsychopharmacol. Feb. 2002;12(1):13-25.
Kussie, et al. Structure of the MDM2 oncoprotein bound to the p53 tumor suppressor transactivation domain. Science. Nov. 8, 1996;274(5289):948-53.
Kutchukian, et al. All-atom model for stabilization of alpha-helical structure in peptides by hydrocarbon staples. J Am Chem Soc. Apr. 8, 2009;131(13):4622-7.
Lacombe, et al. Reduction of Olefms on Solid Support Using Diimide. Tetranderon Lett. 1998;39:6785-86.
Lammi, et al. Mutations in AXIN2 cause familial tooth agenesis and predispose to colorectal cancer. Am J Hum Genet. May 2004;74(5):1043-50. Epub Mar. 23, 2004.
Laporte, et al. Molecular and structural basis of cytokine receptor pleiotropy in the interleukin-4/13 system. Cell. Jan. 25, 2008;132(2):259-72.
Le Geuzennec, et al. Molecular characterization of Sin3 PAH-domain interactor specificity and identification of PAH partners. Nucleic Acids Res. 2006;34(14):392937. Epub Aug. 12, 2006.
Le Geuzennec, et al. Molecular determinants of the interaction of Mad with the PAH2 domain of mSin3. J Biol Chem. Jun. 11, 2004;279(24):25823-9.
Leduc, et al. Helix-stabilized cyclic peptides as selective inhibitors of steroid receptor-coactivator interactions. Proc Natl Acad Sci U S A. Sep. 30, 2003;100(20):11273-8.
Liang, et al. Wnt5a inhibits B cell proliferation and functions as a tumor suppressor in hematopoietic tissue. Cancer Cell. Nov. 2003;4(5):349-60.
Liskamp, et al. Conformationally restricted amino acids and dipeptides, (non)peptidomimetics and secondary structure mimetics. Recl Travl Chim Pays-Bas. 1994; 113:1-19.
Little, et al. A Mutation in the LDL Receptor-Related Protein 5 Gene Results in the Autosomal Dominant High-Bone-Mass Trait. Am J Hum Genet. 2002;70:11-19.

(56) References Cited

OTHER PUBLICATIONS

Liu, et al. Chemical ligation approach to form a peptide bond between unprotected peptide segments. Concept and model study. J Am Chem Soc. 1994; 116(10):4149-53.
Liu, et al. Targeted degradation of beta-catenin by chimeric F-box fusion proteins. Biochem Biophys Res Commun. Jan. 23, 2004;313(4):1023-9.
Lo, et al. Phosphorylation by the beta-catenin/MAPK complex promotes 14-3-3-mediated nuclear export of TCF/POP-1 in signal-responsive cells in C. elegans. Cell. Apr. 2, 2004;117(1):95-106.
Logan, et al. The Wnt signaling pathway in development and disease. Annu Rev Cell Dev Biol. 2004;20:781-810.
Losey, et al.Crystal structure of Staphylococcus aureus tRNA adenosine deaminase TadA in complex with RNA. Nat Struct Mol Biol. Feb. 2006;13(2):153-9.
Loughlin, et al. Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Luo, et al. Wnt signaling and hunian diseases: what are the therapeutic implications? Lab Invest. Feb. 2007;87(2):97-103. Epub Jan. 8, 2007.
Luu, et al. Wnt/beta-catenin signaling pathway as a novel cancer drug target. Curr Cancer Drug Targets. Dec. 2004;4(8):653-71.
MacMillan. Evolving strategies for protein synthesis converge on native chemical ligation. Angew Chem Int Ed Engl. Nov. 27, 2006;45(46):7668-72.
Miloux, et al. Cloning of the human IL-13R alpha1 chain and reconstitution with the IL4R alpha of a functional IL-4/IL-13 receptor complex. FEBS Lett. Jan. 20, 1997;401(2-3):163-6.
Miyaoka, et al. Increased expression of Wnt-1 in schizophrenic brains. Schizophr Res. Jul. 27, 1999;38(1):1-6.
Moellering, et al. Direct inhibition of the NOTCH transcription factor complex. Nature. Nov. 12, 2009;462(7270):182-8.
Moon, et al. WNT and beta-catenin signalling: diseases and therapies. Nat Rev Genet. Sep. 2004;5(9):689-699.
Morin. beta-catenin signaling and cancer. Bioessays. Dec. 1999;21(12):1021-30.
Moy, et al. Solution structure of human IL-13 and implication for receptor binding. J Mol Biol. Jun. 29, 2001;310(1):219-30.
Mudher, et al. Alzheimer's disease-do tauists and baptists fmally shake hands? Trends Neurosci. Jan. 2002;25(1):22-6.
Muir, et al. Expressed protein ligation: a general method for protein engineering. Proc Nath Acad Sci U S A. Jun. 9, 1998;95(12):6705-10.
Muir. Semisynthesis of proteins by expressed protein ligation. Annu Rev Biochem. 2003;72:249-89.
Myung, et al. The ubiquitin-proteasome pathway and proteasome inhibitors. Med Res Rev. Jul. 2001;21(4):245-73.
Nair, et al. X-ray structures of Myc-Max and Mad-Max recognizing DNA. Molecular bases of regulation by proto-oncogenic transcription factors. Cell. Jan. 24, 2003;112(2):193-205.
Nakashima, et al. Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Niemann, et al. Homozygous WNT3 mutation causes tetra-amelia in a large consanguineous family. Am J Hum Genet. Mar. 2004;74(3):558-63. Epub Feb. 5, 2004.
Nilsson, et al. Staudinger ligation: a peptide from a thioester and azide. Org Lett. Jun. 29, 2000;2(13):1939-41.
Nishisho, et al. Mutations of chromosome 5q21 genes in FAP and colorectal cancer patients. Science. Aug. 9, 1991;253(5020):665-9.
Node, et al. Hard acid and soft nucleophile systems. 3. Dealkylation of esters with aluminum halide-thiol and aluminum halide-sulfide stustems. J Org Chem. 1981; 46:1991-93.
Office action dated Feb. 17, 2011 for U.S. Appl. No. 12/796,212.
Okamura, et al. Redundant regulation of T cell differentiation and TCRalpha gene expression by the transcription factors LEF-1 and TCF-1. Immunity. Jan. 1998;8(1):11-20.
Olson, et al. Sizing up the heart: development redux in disease. Genes Dev. Aug. 15, 2003;17(16):1937-56. Epub Jul. 31, 2003.
Pakotiprapha, et al. Crystal structure of Bacillus stearothermophilus UvrA provides insight into ATP-modulated dimerization, UvrB interaction, and DNA binding. Mol Cell. Jan. 18, 2008;29(1):122-33.
Perantoni. Renal development: perspectives on a Wnt-dependent process. Semin Cell Dev Biol. Aug. 2003;14(4):201-8.
Phelan, et al. A general method for constraining short peptides to an alpha-helical conformation. J Am Chem Soc. 1997; 119(3):455-60.
Polakis. The oncogenic activation of beta-catenin. Curr Opin. Genet Dev. Feb. 1999;9(1):15-21.
Qiu, et al. Convenient, large-scale asymmetric synthesis of enantiomerically pure trans-cinnamylglycine and -alpha-alanine. Tetrahedron. 2000; 56:2577-82.
Rawlinson, et al. CRM1-mediated nuclear export of dengue virus RNA polymerase NS5 modulates interleukin-8 induction and virus production. J Biol Chem. Jun. 5, 2009;284(23):15589-97.
Reya, et al. Wnt signalling in stem cells and cancer. Nature. Apr. 14, 2005;434(7035):843-50.
Rich, et al. Synthesis of the cytostatic cyclic tetrapeptide, chlamydocin. Tetranderon Letts. 1983;24(48):5305-08.
Robitaille, et al. Mutant frizzled-4 disrupts retinal angiogenesis in familial exudative vitreoretinopathy. Nat Genet. Oct. 2002;32(2):326-30. Epub Aug. 12, 2002.
Rodova, et al. The polycystic kidney disease-1 promoter is a target of the beta-catenin/T-cell factor pathway. J Biol Chem. Aug. 16, 2002;277(33):29577-83. Epub Jun. 4, 2002.
Roos, et al. Synthesis of alpha-substituted alpha-amino acids via cationic intermediates. J Org Chem. 1993; 58:3259-68.
Ross, et al. Inhibition of adipogenesis by Wnt signaling. Science. Aug. 11, 2000;289(5481):950-3.
Sampietro, et al. Crystal structure of a beta-catenin/BCL9/Tcf4 complex. Mol Cell. Oct. 20, 2006;24(2):293-300.
Satoh, et al. AXIN1 mutations in hepatocellular carcinomas, and growth suppression in cancer cells by virus-mediated transfer of AXIN1. Nat Genet. Mar. 2000;24(3):245-50.
Sattler, et al. Structure of Bcl-xL-Bak peptide complex: recognition between regulators of apoptosis. Science. Feb. 14, 1997;275(5302):983-6.
Saxon, et al. Cell surface engineering by a modified Staudinger reaction. Science. Mar. 17, 2000;287(5460):2007-10.
Schafmeister, et al. An all-hydrocarbon cross-linking system for enhancing the helicity and metabolic stability of peptides. Journal of the American Chemical Society. 2000;122(24):5891-5892.
Scheffzek, et al. The Ras-RasGAP complex: structural basis for GTPase activation and its loss in oncogenic Ras mutants. Science. Jul. 18, 1997;277(5324):333-8.
Scholtz, et al. The mechanism of alpha-helix formation by peptides. Annu Rev Biophys Biomol Struct. 1992;21:95-118.
Schrock, et al. Tungsten(VI) neopentylidyne complexes. Organometallics. 1982; 1:1645-51.
Shair. A closer view of an oncoprotein-tumor suppressor interaction. Chem Biol. Nov. 1997;4(11):791-4.
Si, et al. CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Soucek, et al. Modelling Myc inhibition as a cancer therapy. Nature. Oct. 2, 2008;455(7213):679-83.
Still, et al. Semianalytical treatment of solvation for molecular mechanics and dynamics. J Am Chem Soc. 1990; 112:6127-29.
Su, et al. Eradication of pathogenic beta-catenin by Skpl/Cullin/F box ubiquitination machinery. Proc Natl Acad Sci U S A. Oct. 28, 2003;100(22):12729-34. Epub Oct. 16, 2003.
Takeda, et al. Human sebaceous tumors harbor inactivating mutations in LEF1. Nat Med. Apr. 2006;12(4):395-7. Epub Mar. 26, 2006.
Thompson, et al. Mutants of interleukin 13 with altered reactivity toward interleukin 13 receptors. J Biol Chem. 1999; 275(42):29944-50.
Tian, et al. The role of the Wnt-signaling antagonist DKK1 in the development of osteolytic lesions in multiple myeloma. N Engl J Med. Dec. 25, 2003;349(26):2483-94.

(56) References Cited

OTHER PUBLICATIONS

Toomes, et al. Mutations in LRP5 or FZD4 underlie the common familial exudative vitreoretinopathy locus on chromosome 11q. Am J Hum Genet. Apr. 2004;74(4):721-30. Epub Mar. 2004.
Torrance, et al. Combinatorial chemoprevention of intestinal neoplasia. Nat Med. Sep. 2000;6(9):1024-8.
Tsuji, et al. Antiproliferative activity of REIC/Didc-3 and its significant down-regulation in non¬small-cell lung carcinomas. Biochem Biophys Res Commun. Nov. 23, 2001;289(1):257-63.
Vaickus, et al. Immune markers in hematologic malignancies.Crit Rev Oncol Hematol. Dec. 1991;11(4):267-97.
Van Genderen, et al. Development of several organs that require inductive epithelial-mesenchymal interactions is impaired in LEF-1-deficient mice. Genes Dev. Nov. 15, 1994;8(22):2691-703.
Van Gun, et al.,The wnt-frizzled cascade in cardiovascular disease. Cardiovasc Res. Jul. 2002;55(1):16-24.
Varallo, et al. Beta-catenin expression in Dupuytren's disease: potential role for cell-matrix interactions in modulating beta-catenin levels in vivo and in vitro. Oncogene. Jun. 12, 2003;22(24):3680-4.
Venancio, et al.Reconstructing the ubiquitin network: cross-talk with other systems and identification of novel functions. Genome Biol. 2009;10(3):R33.
Verdine, et al. The challenge of drugging undruggable targets in cancer: lessons learned from targeting BCL-2 family members. Clin Cancer Res. Dec. 15, 2007;13(24):7264-70.
Verma, et al. Small interfering RNAs directed against beta-catenin inhibit the in vitro and in vivo growth of colon cancer cells. Clin Cancer Res. Apr. 2003;9(4):1291-300.
Walter, et al. Critical role for IL-13 in the development of allergen-induced airway hyperreactivity. J Immunol. Oct. 15, 2001;167(8):4668-75.
Wang, et al. Inhibition of p53 degradation by Mdm2 acetylation. FEBS Lett. Mar. 12, 2004;561(1-3):195-201.
Wilen, et al. Strategies in optical resolution. Tetrahedron. 1977; 33:2725-36.
Williams, et al. Asymmetric Synthesis of Monosubstituted and a,a-Disubstituted a-Amino Acids via Diastereoselective Glycine Enolate Allcylations. J Am Chem Soc. 1991;113:9276-86.
Wills-Karp, et al. Interleukin-13: central mediator of allergic asthma. Science. Dec. 18, 1998;282(5397):2258-61.
Wills-Karp. Interleukin-13 in asthma pathogenesis. Immunol Rev. 2004; 202:175-90.
Wills-Karp. The gene encoding interleukin-13: a susceptibility locus for asthma and related traits. Respir Res. 2000;1(1):19-23.
Xi, et al. Use of DNA and peptide nucleic acid molecular beacons for detection and quantification of rRNA in solution and in whole cells. Appl Environ Microbiol. Sep. 2003, 69(9):5673-8.
Xing, et al. Crystal structure of a beta-catenin/axin complex suggests a mechanism for the beta¬catenin destruction complex. Genes Dev. Nov. 15, 2003;17(22):2753-64. Epub Nov. 4, 2003.
Yang, et al. Synthesis and helical structure of lactam bridged BH3 peptides derived from pro-apoptotic Bcl2 family proteins. Bioorg Med Chem Lett. 2004; 14:1403-06.
Yang, et al. Therapeutic dosing with anti-interleukin-13 monoclonal antibody inhibits asthma progression in mice. J Pharmacol Exp Ther. Apr. 2005;313(1):8-15.
Yu, et al. The role of Axin2 in calvarial morphogenesis and craniosynostosis. Development. Apr. 2005;132(8):1995-2005.
Zhou, et al. Identification of ubiquitin target proteins using cell-based arrays. J Proteome Res. 2007; 6:4397-4406.
Zhou, et al. Lymphoid enhancer factor 1 directs hair follicle patterning and epithelial cell fate. Genes Dev. Mar. 15, 1995;9(6):700-13.
Zhou, et al. Tyrosine kinase inhibitor STI-571/Gleevec down-regulates the beta-catenin signaling activity. Cancer Lett. Apr. 25, 2003;193(2):161-70.
Zor, et al. Solution structure of the KIX domain of CBP bound to the transactivation domain of c-Myb. J Mol Biol. Mar. 26, 2004;337(3):521-34.
U.S. Appl. No. 14/068,844, filed Oct. 31, 2013, Verdine et al.
U.S. Appl. No. 14/156,350, filed Jan. 15, 2014, Nash et al.
Office action dated Apr. 9, 2014 for U.S. Appl. No. 13/767,852.
U.S. Appl. No. 13/957,667, filed Aug. 2, 2013, Nash et al.
U.S. Appl. No. 14/070,354, filed Nov. 1, 2013, Walensky et al.
U.S. Appl. No. 14/070,367, filed Nov. 1, 2013, Nash.
Brown, et al. A spiroligomer α-helix mimic that binds HDM2, penetrates human cells and stabilizes HDM2 in cell culture. PLoS One. 2012;7(10):e45948. doi: 10.1371/journal.pone.0045948. Epub Oct. 18, 2012.
Brown, et al. Stapled peptides with improved potency and specificity that activate p53. ACS Chem Biol. Mar. 15, 2013;8(3):506-12. doi: 10.1021/cb3005148. Epub Dec. 18, 2012.
Chang, et al. Stapled α-helical peptide drug development: a potent dual inhibitor of MDM2 and MDMX for p53-dependent cancer therapy. Proc Natl Acad Sci U S A. Sep. 3, 2013;110(36):E3445-54. doi: 10.1073/pnas.1303002110. Epub Aug. 14, 2013.
David, et al. Expressed protein ligation. Method and applications. Eur J Biochem. Feb. 2004;271(4):663-77.
Grossman, et al. Inhibition of oncogenic Wnt signaling through direct targeting of-catenin. Proc. Natl. Acad. Sco. 2012; 109(44):17942-179747.
International preliminary report on patentability dated Jan. 3, 2014 for PCT/US2012/042738.
International preliminary report on patentability dated Apr. 4, 2013 for PCT/US2011/052755.
International search report and written opinion dated Jan. 30, 2014 for PCT/US2013/062929.
International search report and written opinion dated May 16, 2008 for PCT/US2008/052580.
Ji, et al. In vivo activation of the p53 tumor suppressor pathway by an engineered cyclotide. J Am Chem Soc. Aug. 7, 2013;135(31):11623-33. doi: 10.1021/ja405108p. Epub Jul. 25, 2013.
Khalil, et al. An efficient and high yield method for the N-tert-butoxycarbonyl protection of sterically hindered amino acids. Tetrahedron Lett. 1996; 37(20):3441-44.
Office action dated Jan. 13, 2014 for U.S. Appl. No. 13/767,857.
Office action dated Jan. 17, 2014 for U.S. Appl. No. 13/816,880.
Office action dated Feb. 6, 2014 for U.S. Appl. No. 13/680,905.
Pellois, et al. Semisynthetic proteins in mechanistic studies: using chemistry to go where nature can't Curr. Opin. Chem. Biol. 2006; 10(5):487-91.
Sadot, et al. Down-regulation of beta-catenin by activated p53. Mol. Cell Biol. 2001; 21(20):6768-81.
Schwarzer, et al. Protein semisynthesis and expressed protein ligation: chasing a protein's tail. Curr. Opin. Chem. Biol. 2005; 9(6):561-9.
Tolbert, et al. New methods for proteomic research: preparation of protein with N-terminal cysteines for labeling and conjugation. Angew Chem. Int. Ed. Engl. 2002; 41(12):2171-4.
Vartak, et al. Allosteric modulation of the dopamine receptor by conformationally constrained type VI B-turn peptidomimetics of Pro-Leu-Gly-NH2. J. Med. Chem. 2007; 50(26):6725-6729.
Woon, et al. Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.
Office action dated Jul. 16, 2014 for U.S. Appl. No. 13/767,857.
Office action dated Jul. 21, 2014 for U.S. Appl. No. 13/370,057.

\* cited by examiner

| compound | sequence *=R$_8$ *=S$_5$ | charge at pH 7.4 | α helicity | K$_d$ (nM) | cell permeable | cell death |
|---|---|---|---|---|---|---|
| WT | Ac-LSQETFSDLWKLLPEN-NH$_2$ | -2 | 11% | 410±19 | no | - |
| SAH-p53-1 | Ac-LSQETFSD*WKLLPE*-NH$_2$ | -2 | 25% | 100±8 | no | - |
| SAH-p53-2 | Ac-LSQE*FSDLWK*LPEN-NH$_2$ | -2 | 10% | 400±50 | no | - |
| SAH-p53-3 | Ac-LSQ*TFSDLW*LLPEN-NH$_2$ | -2 | 12% | 1200±89 | no | - |
| SAH-p53-4 | Ac-LSQETF*DLWKLL*EN-NH$_2$ | -2 | 59% | 0.92±0.11 | no | - |
| SAH-p53-5 | Ac-LSQETF*NLWKLL*QN-NH$_2$ | 0 | 20% | 0.80±0.05 | yes | - |
| SAH-p53-6 | Ac-LSQQTF*NLWRLL*QN-NH$_2$ | +1 | 14% | 56±11 | yes | - |
| SAH-p53-7 | Ac-QSQQTF*NLWKLL*QN-NH$_2$ | +1 | 36% | 50±10 | yes | - |
| SAH-p53-8 | Ac-QSQQTF*NLWRLL*QN-NH$_2$ | +1 | 85% | 55±11 | yes | + |
| SAH-p53-8$_{F19A}$ | Ac-QSQQTA*NLWRLL*QN-NH$_2$ | +1 | 39% | >4000 | yes | - |
| UAH-p53-8 | Ac-QSQQTF*NLWRKK*QN-NH$_2$ | +1 | 36% | 100±10 | yes | - |

FIG. 1B

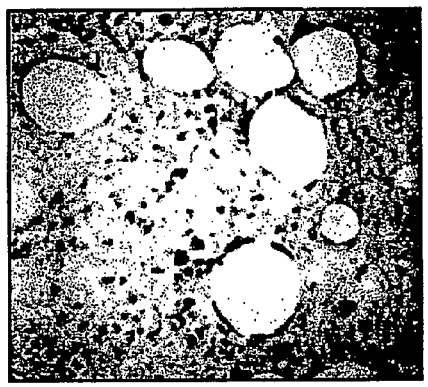

FIG. 14A

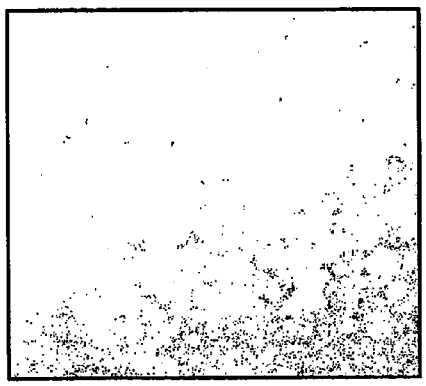

FIG. 14B

```
  1 meepqsdpsv epplsqetfs dlwkllpenn vlsplpsqam ddlmlspddi eqwftedpgp
 61 deaprmpeaa prvapapaap tpaapapaps wplsssvpsq ktyqgsygfr lgflhsgtak
121 svtctyspal nkmfcqlakt cpvqlwvdst pppgtrvram aiykqsqhmt evvrrcphhe
181 rcsdsdglap pqhlirvegn lrveylddrn tfrhsvvvpy eppevgsdct tihynymcns
241 scmggmnrrp iltiitleds sgnllgrnsf evrvcacpgr drrteeenlr kkgephhelp
301 pgstkralpn ntssspqpkk kpldgeyftl qirgrerfem frelnealel kdaqagkepg
361 gsrahsshlk skkgqstsrh kklmfktegp dsd
```

FIG. 15

1. Cap-Linker-L-*-Q-E-T-F-S-D-*-W-K-L-L-P-E-N-NH$_2$
2. Cap-Linker-L-S-Q-*-T-F-S-D-L-W-*-L-L-P-E-N-NH$_2$
3. Cap-Linker-L-S-Q-E-*-F-S-D-L-W-K-*-L-L-P-E-N-NH$_2$
4. Cap-Linker-L-S-Q-E-T-*-S-D-L-W-K-L-*-P-E-N-NH$_2$
5. Cap-Linker-L-S-Q-E-T-F-*-D-L-W-K-L-L-*-E-N-NH$_2$ (SAH-p53-4)
6. Cap-Linker-L-*-Q-E-T-F-S-*-L-W-K-L-L-P-*-N-NH$_2$
7. Cap-Linker-L-S-Q-E-T-F-S-D-*-W-K-L-L-P-E-*-NH$_2$
- "Cap" denotes Ac (acetyl) or FITC (fluorescein thiocarbomoyl); "Linker" denotes β-alanine or no linker; "*" indicates the amino acid pairs R$_5$-S$_8$ or R$_8$-S$_5$ in either uncross-linked (unstapled, unmetathesized) or cross-linked (stapled, metathesized) form
8. Cap-Linker-L-S-Q-Q-T-F-*-D-L-W-K-L-L-*-E-N-NH$_2$
9. Cap-Linker-L-S-Q-E-T-F-*-D-L-W-K-L-L-*-Q-N-NH$_2$
10. Cap-Linker-L-S-Q-Q-T-F-*-D-L-W-K-L-L-*-Q-N-NH$_2$
11. Cap-Linker-L-S-Q-E-T-F-*-N-L-W-K-L-L-*-Q-N-NH$_2$
12. Cap-Linker-L-S-Q-Q-T-F-*-N-L-W-K-L-L-*-Q-N-NH$_2$
13. Cap-Linker-L-S-Q-Q-T-F-*-N-L-W-R-L-L-*-Q-N-NH$_2$
14. Cap-Linker-Q-S-Q-Q-T-F-*-N-L-W-K-L-L-*-Q-N-NH$_2$
15. Cap-Linker-Q-S-Q-Q-T-F-*-N-L-W-R-L-L-*-Q-N-NH$_2$ (SAH-p53-8)
16. Cap-Linker-Q-S-Q-Q-T-A-*-N-L-W-R-L-L-*-Q-N-NH$_2$ (SAH-p53-8$_{F19A}$)
- "Cap" denotes Ac (acetyl), FITC (fluorescein thiocarbamoyl), DOTA (cryptand capable of chelating radoactive In), lauroyl, heptanoyl, and myristoyl; "Linker" denotes β-alanine or no linker; "*" indicates the amino acid pairs R$_5$-S$_8$ or R$_8$-S$_5$ in either uncross-linked (unstapled, unmetathesized) or cross-linked (stapled, metathesized) form
17. Cap-Linker-Q-Q-T-F-*-D-L-W-R-L-L-*-E-N-NH$_2$
18. Cap-Linker-Q-Q-T-F-*-D-L-W-R-L-L-*-NH$_2$
19. Cap-Linker-L-S-Q-Q-T-F-*-D-L-W-*-L-L-NH$_2$
20. Cap-Linker-Q-Q-T-F-*-D-L-W-*-L-L-NH
21. Cap-Linker-Q-Q-T-A-*-D-L-W-R-L-L-*-E-N-NH$_2$
- "Cap" denotes Ac (acetyl), FITC (fluorescein thiocarbamoyl), lauroyl, heptanoyl, and myristoyl; "Linker" denotes β-alanine or no linker; "*" indicates the amino acid pairs R$_8$-S$_5$ (peptides 17, 18, and 21) or S$_5$-S$_5$ (peptides 19 and 20) in either uncross-linked (unstapled, unmetathesized) or cross-linked (stapled, metathesized) forms
22. Cap-K(Myr)-Linker-Q-S-Q-Q-T-F-*-N-L-W-R-L-L-*-Q-N-NH$_2$
23. Cap-K(Biotin)-Linker-Q-S-Q-Q-T-F-*-N-L-W-R-L-L-*-Q-N-NH$_2$
24. Cap-K(PEG3)-Linker-Q-S-Q-Q-T-F-*-N-L-W-R-L-L-*-Q-N-NH$_2$
25. Cap-Linker-Q-S-Q-Q-T-F-*-N-L-W-R-L-L-*-Q-N-NH$_2$ diol
26. Cap-Linker-Q-S-Q-Q-T-A-*-N-L-W-R-L-L-*-Q-N-NH$_2$ diol
- "Cap" denotes Ac (acetyl) or FITC (fluorescein thiocarbamoyl); "Linker" denotes β-alanine or no linker; "*" indicates the amino acid pair R$_8$-S$_5$ in either uncross-linked (unstapled, unmetathesized) or cross-linked (stapled, metathesized) form; "diol" indicates a dihydroxylated cross-link olefin

FIG. 16-1

27. Cap-Linker-Q-S-Q-Q-T-F-*-D-L-W-R-L-L-*-Q-N-NH$_2$ (SAH-p53-10)
28. Cap-Linker-Q-T-F-*-N-L-W-R-L-L-*-NH$_2$ (SAH-p53-11)
29. Cap-Linker-Q-S-Q-Q-T-F-*-N-L-W-*-L-L-P-Q-N-NH$_2$ (SAH-p53-8S$_A$)
30. Cap-Linker-Q-S-*-Q-T-F-*-N-L-W-R-L-L-P-Q-N-NH$_2$ (SAH-p53-8S$_B$)
31. Cap-Linker-*-T-F-S-*-L-W-K-L-L-NH$_2$ (SAH-p53-12)
32. Cap-Linker-E-T-F-*-D-L-W-*-L-L-NH$_2$ (SAH-p53-13)
33. Cap-Linker-Q-T-F-*-N-L-W-*-L-L-NH$_2$ (SAH-p53-14)
34. Cap-Linker-*-S-Q-E-*-F-S-N-L-W-K-L-L-NH$_2$ (SAH-p53-15)

FIG. 16-2

STABILIZED P53 PEPTIDES AND USES THEREOF

CROSS-REFERENCE TO RELATED APPLICATIONS

This application is the National Stage of International Application No. PCT/US2008/052580 filed on Jan. 31, 2008, which claims priority to U.S. Provisional Application Ser. No. 60/887,526, filed on Jan. 31, 2007, the entire contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 18, 2014, is named 35224-751.831_SL.txt and is 31,675 bytes in size.

BACKGROUND

The human p53 transcription factor induces cell cycle arrest and apoptosis in response to DNA damage[1] and cellular stress,[2] thereby playing a critical role in protecting cells from malignant transformation. The E3 ubiquitin ligase HDM2 controls p53 levels through a direct binding interaction that neutralizes p53 transactivation activity, exports nuclear p53, and targets it for degradation via the ubiquitylation-proteasomal pathway.[3, 4] Loss of p53 activity, either by deletion, mutation, or HDM2 overexpression, is the most common defect in human cancer.[5] Tumors with preserved expression of wild type p53 are rendered vulnerable by pharmacologic approaches that stabilize native p53. In this context, HDM2 targeting has emerged as a validated approach to restore p53 activity and resensitize cancer cells to apoptosis in vitro and in vivo.[6] HDMX (HDM4) has also been identified as a regulator of p53. Moreover, studies have shown a similarity between the p53 binding interface of HDM2 and that of HDMX.[6a]

The p53-HDM2 protein interaction is mediated by the 15-residue α-helical transactivation domain of p53, which inserts into a hydrophobic cleft on the surface of HDM2.[7] Three residues within this domain (F19, W23, and L26) are essential for HDM2-binding.[8, 9]

SUMMARY

Described below are stably cross-linked peptides related to a portion of human p53 ("stapled p53 peptides"). These cross-linked peptides contain at least two modified amino acids that together form an internal cross-link (also referred to as a tether) that can help to stabilize the alpha-helical secondary structure of a portion of p53 that is thought to be important for binding of p53 to HDM2. Accordingly, a cross-linked polypeptide described herein can have improved biological activity relative to a corresponding polypeptide that is not cross-linked. The stapled p53 peptides are thought to interfere with binding of p53 to HDM2 thereby inhibiting the destruction of p53. The stapled p53 peptide described herein can be used therapeutically, e.g., to treat a variety of cancers in a subject. For example, cancers and other disorders characterized by an undesirably low level or a low activity of p53 and/or cancers and other disorders characterized by an undesirably high level of activity of HDM2. The modified peptides may also be useful for treatment of any disorder associated with disrupted regulation of the p53 transcriptional pathway, leading to conditions of excess cell survival and proliferation (e.g., cancer and autoimmunity), in addition to conditions of inappropriate cell cycle arrest and apoptosis (e.g., neurodegeneration and immune deficiency).

In one aspect, the invention features a modified polypeptide of Formula (I),

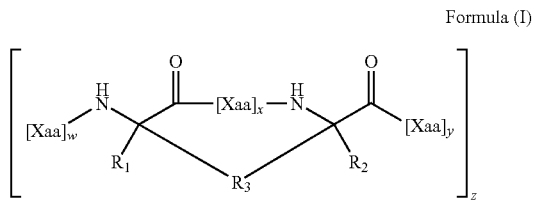

or a pharmaceutically acceptable salt thereof,
wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene, or $[R_4'—K—R_4]_n$; each of which is substituted with 0-6 $R_5$;

$R_4$ and $R_4'$ are independently alkylene, alkenylene or alkynylene (e.g., each are independently a C1, C2, C3, C4, C5, C6, C7, C8, C9 or C10 alkylene, alkenylene or alkynylene);

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

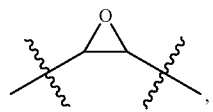

aziridine, episulfide, diol, amino alcohol;

$R_6$ is H, alkyl, or a therapeutic agent;

n is 2, 3, 4 or 6;

x is an integer from 2-10;

w and y are independently an integer from 0-100;

z is an integer from 1-10 (e.g., 1, 2, 3, 4, 5, 6, 7, 8, 9, 10); and each Xaa is independently an amino acid (e.g., one of the 20 naturally occurring amino acids or any naturally occurring non-naturally occurring amino acid);

wherein the polypeptide, comprises at least 8 contiguous amino acids of SEQ ID NO:1 (human p53) or a variant thereof, SEQ ID NO:2 or a variant thereof, or another polypeptide sequence described herein except that: (a) within the 8 contiguous amino acids of SEQ ID NO:1 the side chains of at least one pair of amino acids separated by 3, 4 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (II),

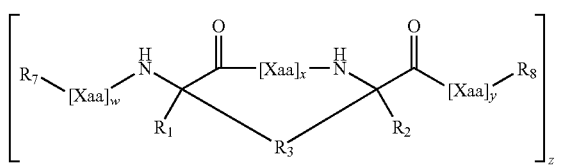

Formula (II)

or a pharmaceutically acceptable, salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene, or $[R_4'-K-R_4]_n$; each of which is substituted with 0-6 $R_5$;

$R_4$ and $R_4'$ are independently alkylene, alkenylene or alkynylene (e.g., each are independently a C1, C2, C3, C4, C5, C6, C7, C8, C9 or C10 alkylene, alkenylene or alkynylene);

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

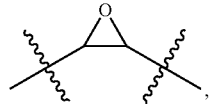 [SMILES: *C1OC1* ; ","]

aziridine, episulfide, diol, amino alcohol;

$R_6$ is H, alkyl, or a therapeutic agent;

n is 2, 3, 4 or 6;

x is an integer from 2-10;

w and y are independently an integer from 0-100;

z is an integer from 1-10 (e.g., 1, 2, 3, 4, 5, 6, 7, 8, 9, 10); and each Xaa is independently an amino acid (e.g., one of the 20 naturally occurring amino acids or any naturally occurring non-naturally occurring amino acid);

$R_7$ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage;

$R_8$ is H, OH, $NH_2$, $NHR_{8a}$, $NR_{8a}R_{8b}$;

wherein the polypeptide comprises at least 8 contiguous amino acids of SEQ ID NO:1 (human p53) or a variant thereof, SEQ ID NO:2 or a variant thereof, or another polypeptide sequence described herein except that: (a) within the 8 contiguous amino acids of SEQ ID NO:1 the side chains of at least one pair of amino acids separated by 3, 4 or 6 amino acids is replaced by the linking group, $R_3$, which connects the alpha carbons of the pair of amino acids as depicted in formula I; and (b) the alpha carbon of the first of the pair of amino acids is substituted with $R_1$ as depicted in Formula II and the alpha carbon of the second of the pair of amino acids is substituted with $R_2$ as depicted in Formula II.

In the case of Formula I or Formula II, the following embodiments are among those disclosed.

In cases where x=2 (i.e., i+3 linkage), $R_3$ can be a C7 alkylene, alkenylene. Where it is an alkenylene there can be one or more double bonds. In cases where x=6 (i.e., i+7 linkage), $R_3$ can be a C11, C12 or C13 alkylene or alkenylene. Where it is an alkenylene there can be one or more double bonds. In cases where x=3 (i.e., i+4 linkage), $R_3$ can be a C8 alkylene, alkenylene. Where it is an alkenylene there can be one or more double bonds.

SEQ ID NO:1 is the sequence of human p53. The stapled peptides can include the sequence Leu Ser Gln Glu Thr Phe Ser Asp Leu Trp Lys Leu Leu Pro Glu Asn (SEQ ID NO:2; corresponds to amino acids 14 to 29 of SEQ ID NO:1). The stapled peptide can also include the sequence Phe Ser Asn Leu Trp Arg Leu Leu Pro Gln Asn (SEQ ID NO:5) or the sequence. Gln Ser Gln Gln Thr Phe Ser Asn Leu Trp Arg Leu Leu Pro Gln Asn (SEQ ID NO:6). In these sequence as in SEQ ID NO:1, 2, 3 and 4), the side chains of two amino acids separated by 2, 3, 4 or 6 amino acids can be replaced by the linking group $R_3$. For example, in SEQ ID NO:5, the side chains of Ser and Pro can be replaced by the linking group $R_3$.

The stapled polypeptide can include all or part (e.g., at least 10, at least 11, at least 12, at least 13) of the following amino acid sequence:

$Xaa_1Ser_2Gln_3Xaa_4Thr_5Phe_6Xaa_7Xaa_8Leu_9Trp_{10}Xaa_{11}$-$Leu_{12}Leu_{13}Xaa_{14}Xaa_{15}Asn_{16}$. (SEQ ID NO:3) wherein each of $Xaa_1$, $Xaa_4$, $Xaa_7$, $Xaa_8$, $Xaa_{11}$, $Xaa_{14}$, $Xaa_{15}$ are any amino acid (e.g., any of the 20 naturally occurring amino acids).

In some situations:

$Xaa_1$=Leu or Gln or the linking group $R_3$ $Xaa_4$=Glu or Gln or the linking group $R_3$ $Xaa_7$=Ser or the linking group $R_3$ $Xaa_8$=Asp or any amino acid other than Asp and Glu (preferably Asn; e.g., $Xaa_8$ can be Asp or Asn) or the linking group $R_3$ $Xaa_{11}$=Lys or a positively charged amino acid (preferably Arg) or the linking group $R_3$ $Xaa_{14}$=Pro or the linking group $R_3$ $Xaa_{15}$=Glu or any amino acid other than Asp and Glu (preferably Gln) or the linking group $R_3$.

In some situations, the peptide comprises SEQ ID NO:3 wherein $Xaa_1$=Leu or Gln or the linking group $R_3$; $Xaa_4$=Glu or Gln or the linking group $R_3$; $Xaa_7$=Ser or the linking group $R_3$; $Xaa_8$=Asp, Asn or the linking group $R_3$; $Xaa_{11}$=Lys, Arg or the linking group $R_3$; $Xaa_{14}$=Pro or the linking group $R_3$; $Xaa_{15}$=Glu, Gln or the linking group $R_3$. In the stapled peptides, any position occupied by Gln can be Glu instead and any position occupied by Glu can be Gln instead. Similarly, any position occupied by Asn can be Asp instead and any position occupied by Aps can be Asn instead. The choice of Asn or Arg and Gln or Glu will depend on the desired charge of the stapled peptide.

In some cases the peptide comprises a portion of SEQ ID NO:3 having the sequence: $Gln_3Xaa_4Thr_5Phe_6Xaa_7Xaa_8Leu_9Trp_{10}Xaa_{11}Leu_{12}Leu_{13}$ (SEQ ID NO:4).

Within SEQ ID NO:3, the pairs of amino acid that can be cross-linked include, but are not limited to: the $5^{th}$ and $12^{th}$ amino acids; $4^{th}$ and $11^{th}$ amino acids; $7^{th}$ and $11^{th}$ amino acids; and $7^{th}$ and $14^{th}$ amino acids In some instances, the modified peptide binds to HDM2 (e.g., GenBank® Accession No.: 228952; GI:228952) and/or HDM4 (also referred to as HDMX; GenBank® Accession No.: 88702791; GI:88702791). In some instances it can be useful to create an inactive stapled peptide by replacing one or more (e.g., all three) of $Phe_6$, $Trp_{10}$, $Leu_{13}$ with another amino acid, e.g., Ala.

Additional useful peptides include non-cross-linked peptides having the following amino acid sequence:

$Xaa_1Ser_2Gln_3Xaa_4Thr_5Phe_6Xaa_7Xaa_8Leu_9Trp_{10}Xaa_{11}$-$Leu_{12}Leu_{13}Xaa_{14}Xaa_{15}Asn_{16}$. (SEQ ID NO:3) wherein each of $Xaa_1$, $Xaa_4$, $Xaa_7$, $Xaa_8$, $Xaa_{11}$, $Xaa_{14}$, $Xaa_{15}$ are any amino acid (e.g., any of the 20 naturally occurring amino acids).

In some cases of such non-cross-linked peptides:

$Xaa_1$=Leu or Gln or the linking group $R_3$
$Xaa_4$=Glu or Gln or the linking group $R_3$
$Xaa_7$=Ser or the linking group $R_3$
$Xaa_8$=Asp or any amino acid other than Asp and Glu (preferably Asn) or the linking group $R_3$
$Xaa_{11}$=Lys or a positively charged amino acid (preferably Arg) or the linking group $R_3$
$Xaa_{14}$=Pro or the linking group $R_3$
$Xaa_{15}$=Glu or any amino acid other than Asp and Glu (preferably Gln) or the linking group $R_3$ In some cases the non-cross-linked peptide comprises a portion of SEQ ID NO:3 having the sequence: $Gln_3Xaa_4Thr_5Phe_6Xaa_7Xaa_8Leu_9Trp_{10}Xaa_{11}Leu_{12}Leu_{13}$ (SEQ ID NO:4).

In some instance the modified peptide further comprises, for example: PEG, a fatty acid, or an antibody (e.g., an antibody that targets the modified peptide to a cell expressing p53, HDM2 or HDM4).

In some instances, each w is independently an integer between 3 and 15. In some instances each y is independently an integer between 1 and 15. In some instances, $R_1$ and $R_2$ are each independently H or $C_1$-$C_6$ alkyl. In some instances, $R_1$ and $R_2$ are each independently $C_1$-$C_3$ alkyl. In some instances, at least one of $R_1$ and $R_2$ are methyl. For example $R_1$ and $R_2$ are both methyl. In some instances $R_3$ is alkyl (e.g., $C_8$ alkyl) and x is 3. In some instances, $R_3$ is $C_{11}$ alkyl and x is 6. In some instances, $R_3$ is alkenyl (e.g., $C_8$ alkenyl) and x is 3. In some instances x is 6 and $R_3$ is $C_{11}$ alkenyl. In some instances, $R_3$ is a straight chain alkyl, alkenyl, or alkynyl. In some instances $R_3$ is —$CH_2$—$CH_2$—$CH_2$—CH=CH—$CH_2$—$CH_2$—$CH_2$—. In some instances $R_3$ is —$CH_2$—$CH_2$—$CH_2$—$CH_2$—$CH_2$—CH=CH—$CH_2$—$CH_2$—$CH_2$—. In some instances $R_3$ is —$CH_2$—$CH_2$—$CH_2$—CH=CH—$CH_2$—$CH_2$—$CH_2$—$CH_2$—$CH_2$—.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

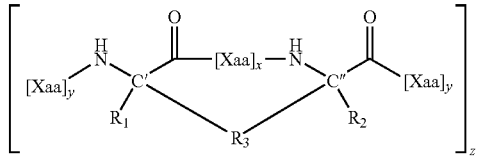

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration. The $R_3$ double bond may be in the E or Z stereochemical configuration. Similar configurations are possible for the carbons in Formula II corresponding to C' and C" in the formula depicted immediately above.

In some instances $R_3$ is $[R_4—K—R_4']_n$; and $R_4$ and $R_4'$ are independently alkylene, alkenylene or alkynylene (e.g., each are independently a C1, C2, C3, C4, C5, C6, C7, C8, C9 or C10 alkylene, alkenylene or alkynylene In some instances, the polypeptide includes an amino acid sequence which, in addition to the amino acids side chains that are replaced by a cross-link, have 1, 2, 3, 4 or 5 amino acid changes in any of SEQ ID NOs:1-4.

The tether can include an alkyl, alkenyl, or alkynyl moiety (e.g., $C_5$, $C_8$ or $C_{11}$, alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). $[Xaa]_y$ and $[Xaa]_w$ are peptides that can independently comprise at least 1, 2, 3, 4, 5, 6, 7, 8, 9, 10, 11, 12, 13, 14, 15, 16, 17, 18, 19, 20, 25 or more contiguous amino acids (preferably 2 or 5 contiguous amino acids) of a p53 polypeptide (e.g., any of SEQ ID NOs:1-4) and $[Xaa]_x$ is a peptide that can comprise 3 or 6 contiguous amino acids of acids of a p53 peptide.

The peptide can comprise 8, 9, 10, 11, 12, 13, 14, 15, 16, 17, 18, 19, 20, 25, 30, 35, 40, 45, 50 amino acids of p53 polypeptide. The amino acids are contiguous except that one or more pairs of amino acids separated by 3 or 6 amino acids are replaced by amino acid substitutes that form a cross-link, e.g., via $R_3$. Thus, at least two amino acids can be replaced by tethered amino acids or tethered amino acid substitutes. Thus, where formula I is depicted as

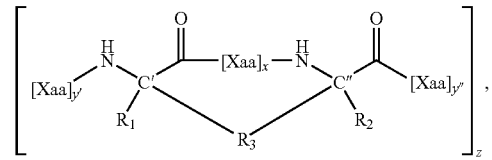

$[Xaa]_{y'}$, $[Xaa]_x$ and $[Xaa]_{y''}$ can each comprise contiguous polypeptide sequences from the same or different p53 peptides. The same is true for Formula II.

The peptides can include 10 (11, 12, 13, 14, 15, 16, 17, 18, 19, 20, 21, 22, 23, 24, 25, 30, 35, 40, 45, 50 or more) contiguous amino acids of a p53 polypeptide wherein the alpha carbons of two amino acids that are separated by three amino acids (or six amino acids) are linked via $R_3$, one of the two alpha carbons is substituted by $R_1$ and the other is substituted by $R_2$ and each is linked via peptide bonds to additional amino acids.

In some instances the polypeptide acts as dominant negative inhibitor p53 degradation. In some instances, the polypeptide also includes a fluorescent moiety or radioisotope or a moiety that, can chelate a radioisotope (e.g., mercaptoacetyltriglycine or 1,4,7,10-tetraazacyclododecane-N, N',N",N'''-tetraacetic acid (DOTA)) chelated to a radioactive isotope of Re, In or Y). In some instances, $R_1$ and $R_2$ are methyl; $R_3$ is $C_8$ alkyl, $C_{11}$ alkyl, $C_8$ alkenyl, $C_{11}$ alkenyl, $C_8$ alkynyl, or $C_{11}$ alkynyl; and x is 2, 3, or 6. In some instances, the polypeptide includes a PEG linker, a tat protein, an affinity label, a targeting moiety, a fatty acid-derived acyl group, a biotin moiety, a fluorescent probe (e.g. fluorescein or rhodamine).

Also described herein is a method of treating a subject including administering to the subject any of the compounds described herein. In some instances, the method also includes administering an additional therapeutic agent, e.g., a chemotherapeutic agent.

The peptides may contain one or more asymmetric centers and thus occur as racemates and racemic mixtures, single enantiomers, individual diastereomers and diastereomeric mixtures and geometric isomers (e.g. Z or cis and E or trans) of any olefins present. All such isomeric forms of these compounds are expressly included in the present invention. The compounds may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are included as are all crystal forms.

Amino acids containing both an amino group and a carboxyl group bonded to a carbon referred to as the alpha carbon. Also bonded to the alpha carbon is a hydrogen and a side-chain. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes. The table below provides the structures of the side chains for each of the 20 common naturally-occurring amino acids. In this table the "—" at right side of each structure is the bond to the alpha carbon.

| Amino acid | Single Letter | Three Letter | Structure of side chain |
| --- | --- | --- | --- |
| Alanine | A | Ala | $CH_3-$ |
| Arginine | R | Arg | $HN=C(NH_2)-NH-(CH_2)_3-$ |
| Asparagine | N | Asn | $H_2N-C(O)-CH_2-$ |
| Aspartic acid | D | Asp | $HO(O)C-CH_2-$ |
| Cysteine | C | Cys | $HS-CH_2-$ |
| Glutamine | Q | Gln | $H_2N-C(O)-(CH_2)_2-$ |
| Glutamic acid | E | Glu | $HO(O)C-(CH_2)_2-$ |
| Glycine | G | Gly | $H-$ |
| Histidine | H | His | $N=CH-NH-CH=C-CH_2-$ (ring) |
| Isoleucine | I | Ile | $CH_3-CH_2-CH(CH_3)-$ |
| Leucine | L | Leu | $(CH_3)_2-CH-CH_2-$ |
| Lysine | K | Lys | $H_2N-(CH_2)_4-$ |
| Methionine | M | Met | $CH_3-S-(CH_2)_2-$ |
| Phenylalanine | F | Phe | Phenyl-$CH_2-$ |
| Proline | P | Pro | $-N-(CH_2)_3-CH-$ (ring) |
| Serine | S | Ser | $HO-CH_2-$ |
| Threonine | T | Thr | $CH_3-CH(OH)-$ |
| Tryptophan | W | Trp | Phenyl—NH—CH=C—$CH_2$— (ring) |
| Tyrosine | Y | Tyr | 4-OH-Phenyl-$CH_2-$ |
| Valine | V | Val | $CH_3-CH(CH_2)-$ |

A "non-essential" amino acid residue is a residue that can be altered from the wild-type sequence of a polypeptide (without abolishing or substantially altering its activity. An "essential" amino acid residue is a residue that, when altered from the wild-type sequence of the polypeptide, results in abolishing or substantially abolishing the polypeptide activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The symbol

" ⚞ "

when used as part of a molecular structure refers to a single bond or a trans or cis double bond.

The term "amino acid side chain" refers to a moiety attached to the α-carbon in an amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., a amide bond). Polypeptides as described herein include full length proteins (e.g., fully processed proteins) as well as shorter amino acids sequences (e.g., fragments of naturally occurring proteins or synthetic polypeptide fragments).

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, 1,2,3-triazolyl, 1,2,4-triazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 14 Immunohistochemistry on mouse tumor xenografts. Two mice each containing three SJSA-1-derived tumor xenografts were treated with 10 mg kg$^{-1}$ SAH-p53-8 (A) or vehicle (B) every 12 hours for two days. Paraffin sections were obtained from the tumor xenografts and were stained using an α-p53 antibody. p53 deficiency due to HDM2 amplification is evidenced in the untreated control (B), while p53 accumulation near capillaries is seen in the sample treated with SAH-p53-8(A).

FIG. 15 Amino acid sequence of human p53 (GenBank® Accession No. CAA42627; gi:50637 (SEQ ID NO: 1)).

FIG. 16 Sequences of various stapled peptides (SEQ ID NOS 20-53, respectively, in order of appearance).

DETAILED DESCRIPTION

Described herein are internally cross-linked alpha helical domain polypeptides related to human p53. The polypeptides include a tether (also called a cross-link) between two non-natural amino acids that significantly enhance the alpha helical secondary structure of the polypeptide. Generally, the tether or cross-link (sometimes referred to as staple) extends across the length of one or two helical turns (i.e., about 3, 4 or about 7 amino acids). Accordingly, amino acids positioned at i and i+3; i and i+4; or i and i+7 are ideal candidates for chemical modification and cross-linking. Thus, for example, where a peptide has the sequence . . . $Xaa_1, Xaa_2, Xaa_3, Xaa_4, Xaa_5, Xaa_6, Xaa_7, Xaa_8, Xaa_9$ . . . (wherein " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc. The polypeptides can include more than one crosslink within the polypeptide sequence to either further stabilize the sequence or facilitate the stabilization of longer polypeptide stretches. If the polypeptides are too long to be readily synthesized in one part, independently synthesized, cross-linked peptides can be conjoined by a technique called native chemical ligation (Bang, et al., *J. Am. Chem Soc.* 126:1377).

Described herein are stabilized alpha-helix of p53 (SAH-p53) peptides that exhibit high affinity for HDM2, and, in contrast to the corresponding unmodified p53 peptide, readily enter cells through an active uptake mechanism. As described below, SAH-p53 treatment reactivated the p53 tumor suppressor cascade by inducing the transcription of p53-responsive genes, providing the first example of a stapled peptide that kills cancer cells by targeting a transcriptional pathway.

Figure 1A:
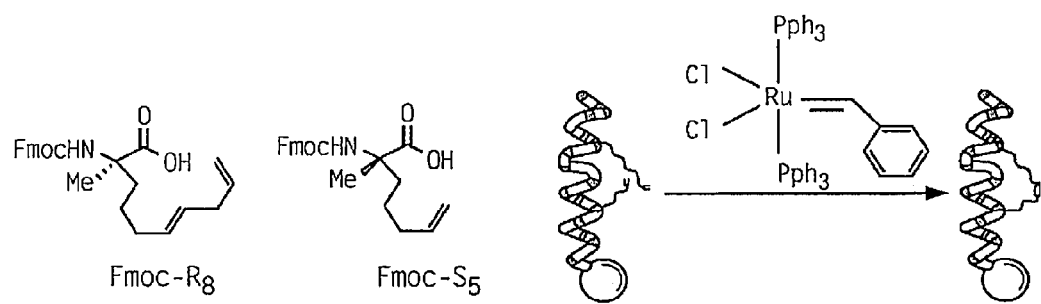
FIG. 1 Synthesis, Sequence, and Biochemical Analysis of SAH-p53 Peptides. (A) Non-natural amino acids were synthesized as described and cross-linked by ruthenium-catalyzed ring-closing olefin metathesis. (B) SAH-p53 compounds (SEQ ID NOS 9-19, respectively, in order of appearance) were generated by stapling the $p53_{14-29}$ sequence at the indicated positions. Charge, α-helicity, HDM2 binding affinity, cell permeability, and cell viability are indicated for each compound. (C, E) Circular dichroism spectra revealed enhancement of alpha-helicity for SAH-p53 compounds. (D, F) Fluorescence polarization assays using FITC-peptides and $HDM2_{17-125}$ demonstrated subnanomolar HDM2-binding affinities for select SAH-p53 peptides. Note: UAH-p53-8 is the "unstapled" form of SAH-p53-8.
Figure 1C:
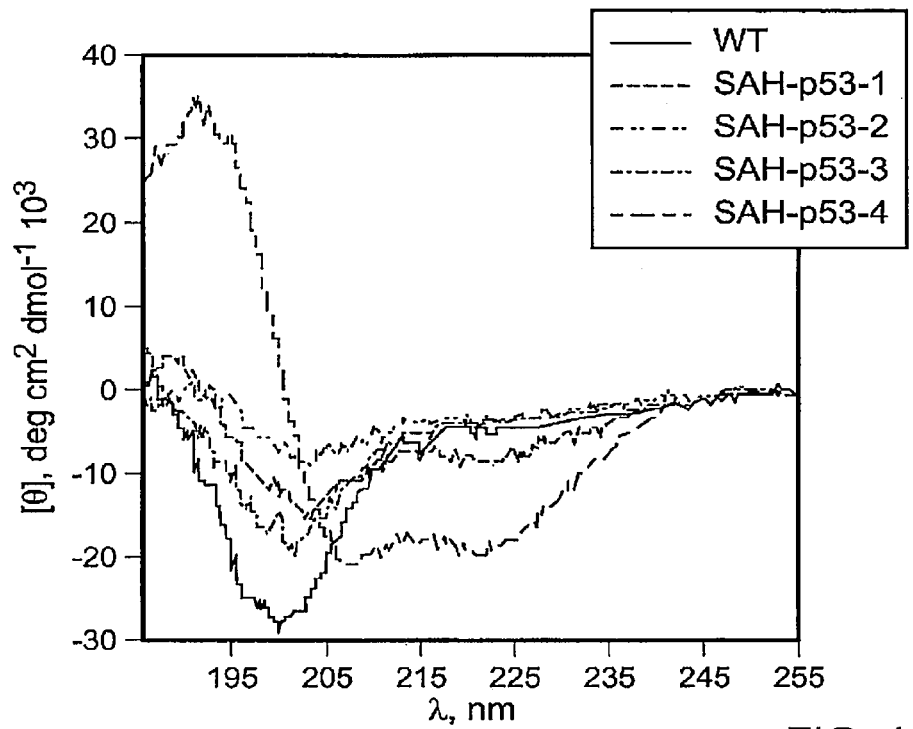
Figure 1D:
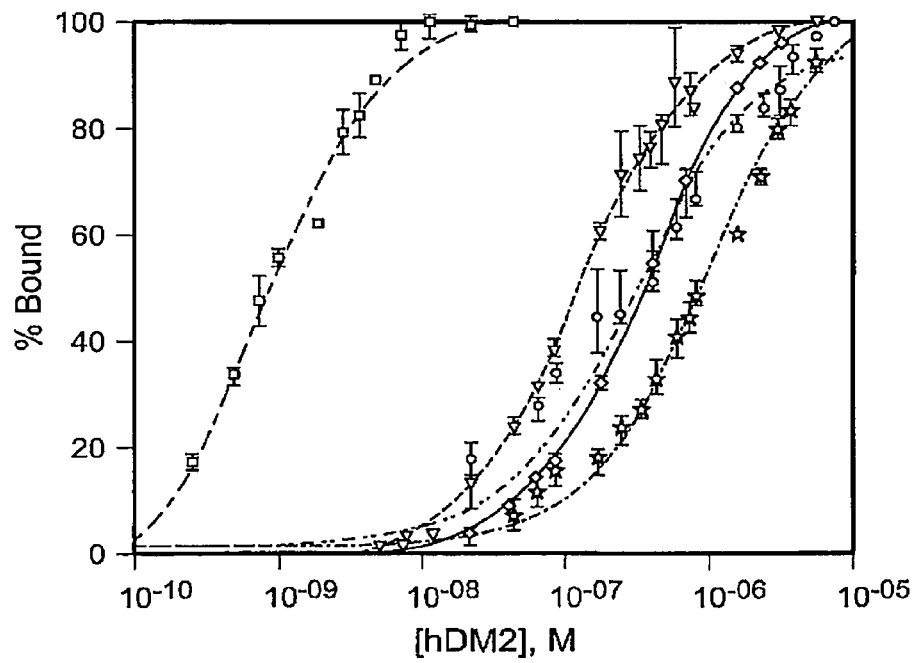
Figure 1E:
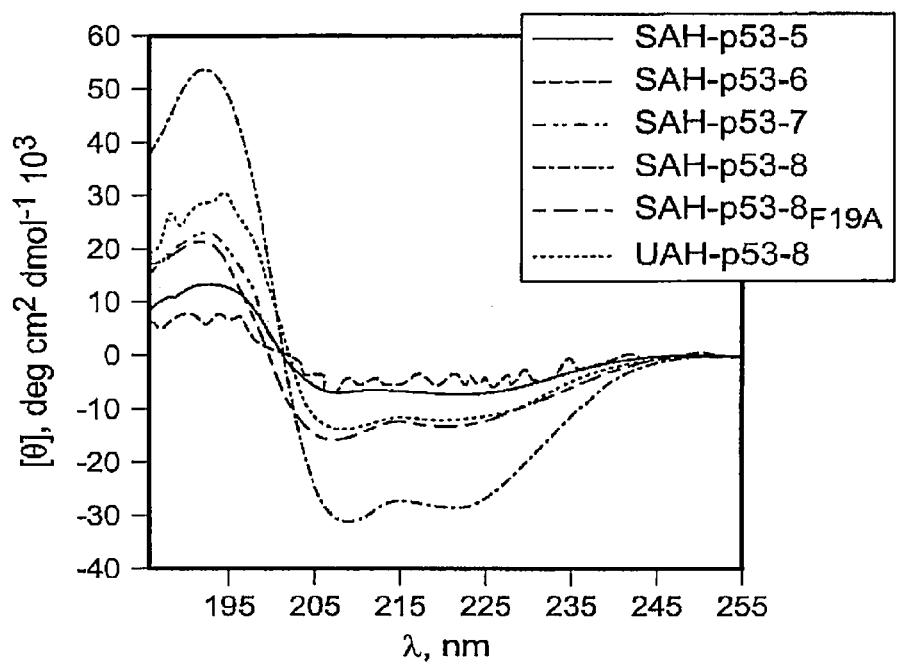
Figure 1F:
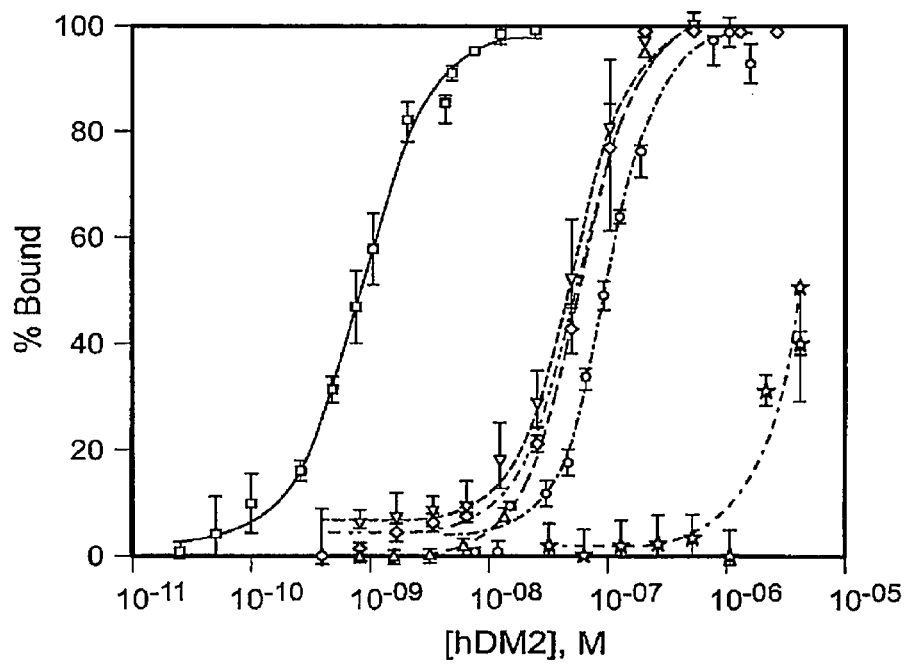
Figure 5:
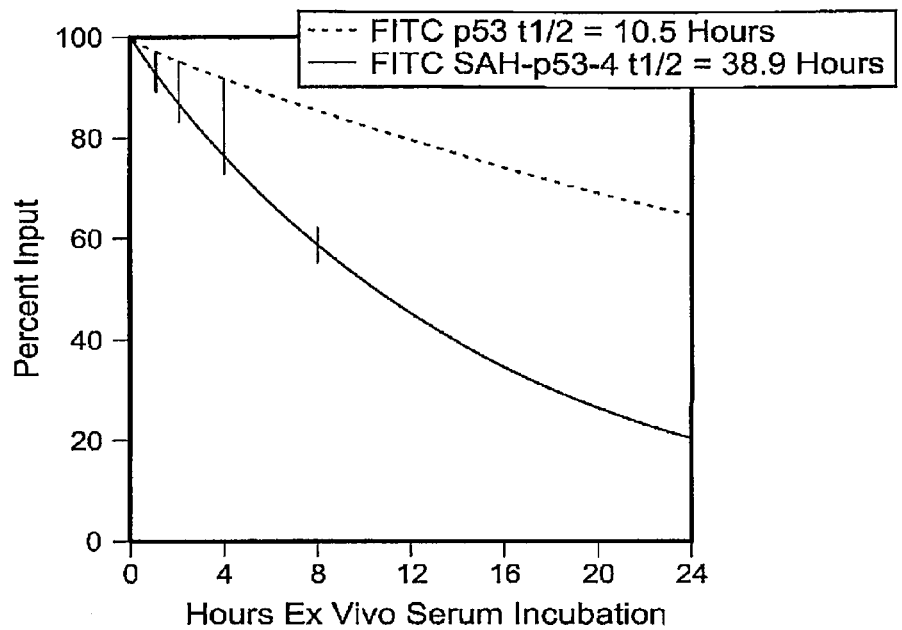
FIG. 5 To determine whether SAH-p53 peptides have increased proteolytic stability, the wild type $p53_{14-29}$ peptide and SAH-p53-4 were exposed to serum ex vivo. SAH-p53-4 displayed a serum half-life ($t_{1/2}$) almost four times longer than that of the unmodified wild type peptide.

To design SAH-p53 compounds, we placed synthetic olefinic derivatives at positions that avoid critical HDM2-binding residues. Hydrocarbon staples spanning the i, i+7 positions were generated by olefin metathesis (FIG. 1A). An initial panel of four SAH-p53 peptides was synthesized, each containing a distinctively localized cross-link (FIG. 1B). To evaluate the structural impact of installing an all-hydrocarbon i, i+7 staple, we conducted circular dichroism (CD) experiments to determine α-helicity. While the wild type p53 peptide displayed 11% α-helical content in water at pH 7.0, SAH-p53s 1-4 demonstrated 10-59% α-helicity (FIGS. 1B and 1C). Fluorescence polarization binding assays using $HDM2_{17-125}$ and FITC-labeled derivatives of SAH-p53s 1-4 identified SAH-p53-4 as a subnanomolar interactor, having an affinity for HDM2 almost three orders of magnitude greater than that of the wild type peptide (FIGS. 1B and 1D). SAH-p53-4 also demonstrated improved proteolytic stability (FIG. 5).

Figure 4A:
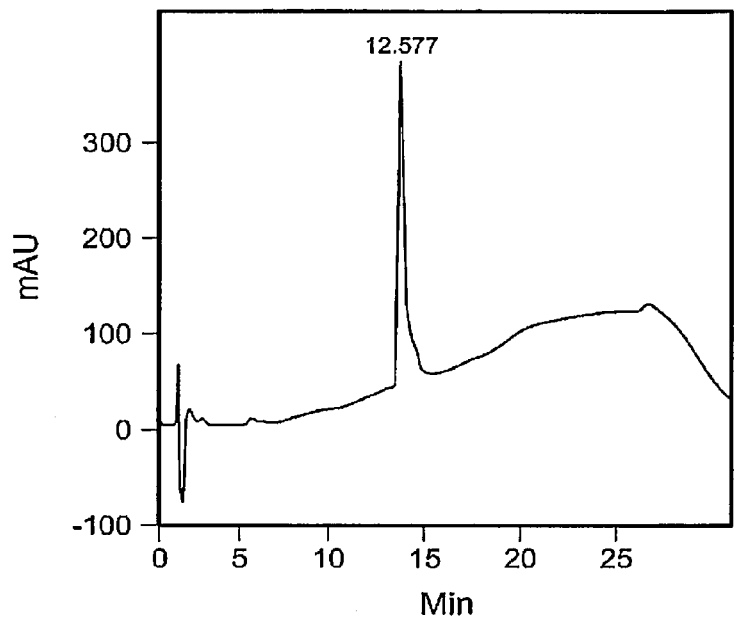
FIG. 4 Electrospray mass spectrum (positive ion mode) of peptide SAH-p53-4.
Figure 6:
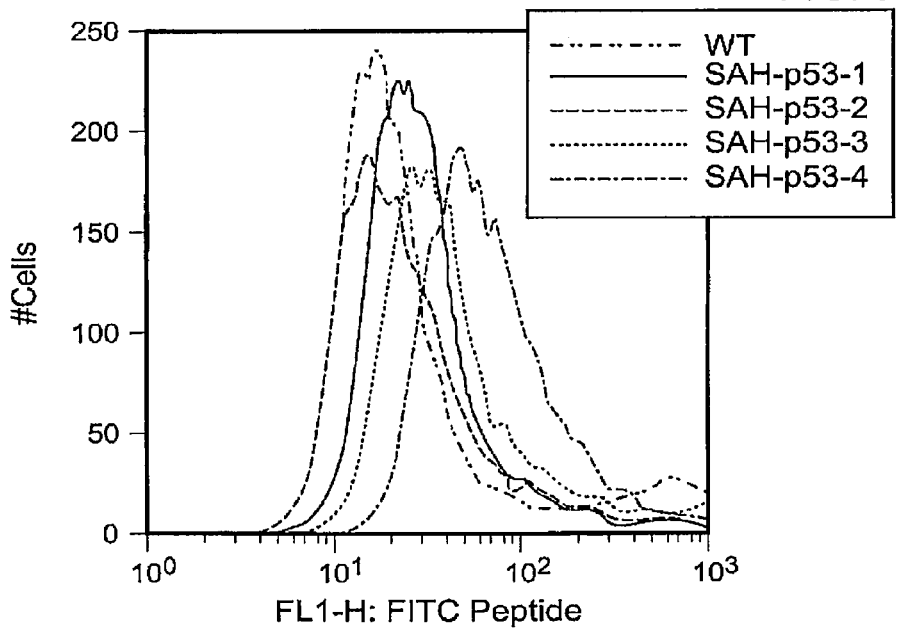
FIG. 6 To determine if SAH-p53 peptides 1-4 were cell permeable, Jurkat T-cell leukemia cells were incubated with fluoresceinated p53 peptides for 4 hours followed by washing, trypsinization, and FACS analysis to evaluate cellular fluorescence. None of the peptides tested produced cellular fluorescence.
Figure 7A:
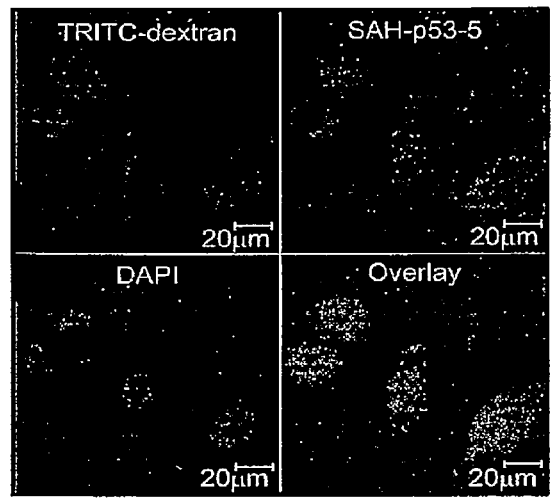
FIG. 7 (A) SJSA-1 cells were treated with FITC-SAH-p53-5 and 4.4 kDa TRITC-dextran for 4 hours. Confocal microscopy revealed co-localization of FITC-SAH-p53-5 peptide with TRITC-dextran in pinosomes. (B) To assess whether the permeability of FITC-SAH-p53-5 was temperature-dependent, Jurkat T-cell leukemia cells were incubated with fluoresceinated p53 peptides for 4 hours at either 4° C. or 37° C. followed by washing, trypsinization, and FACS analysis to evaluate cellular fluorescence. (C) To determine the kinetics of cell permeability, Jurkat T-cell leukemia cells were exposed to FITC-SAH-p53-5 peptide and cellular fluorescence was evaluated by FACS analysis at successive time points. FITC-SAH-p53-5-treated cells displayed a time-dependent increase in cellular fluorescence. (D) SJSA-1 cells were treated with FITC-wild type, SAH-p53-8, and SAH-p53-$8_{F19A}$ peptides for 4 hours followed by FACS and confocal microscopy analyses. Cellular fluorescence was observed after treatment with FITC-SAH-p53 peptides, but not with FITC-wild type p53 peptide.
Figure 7B:
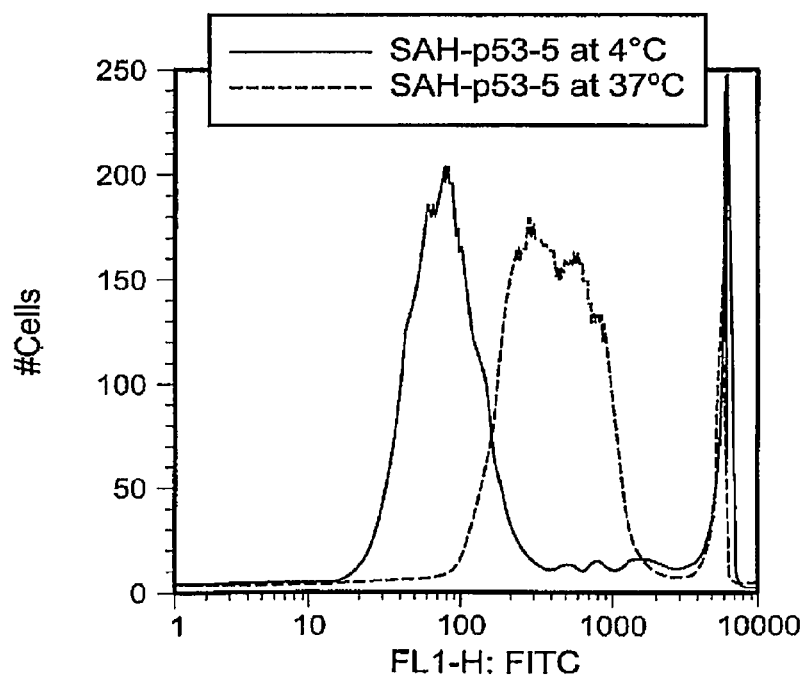
Figure 7C:
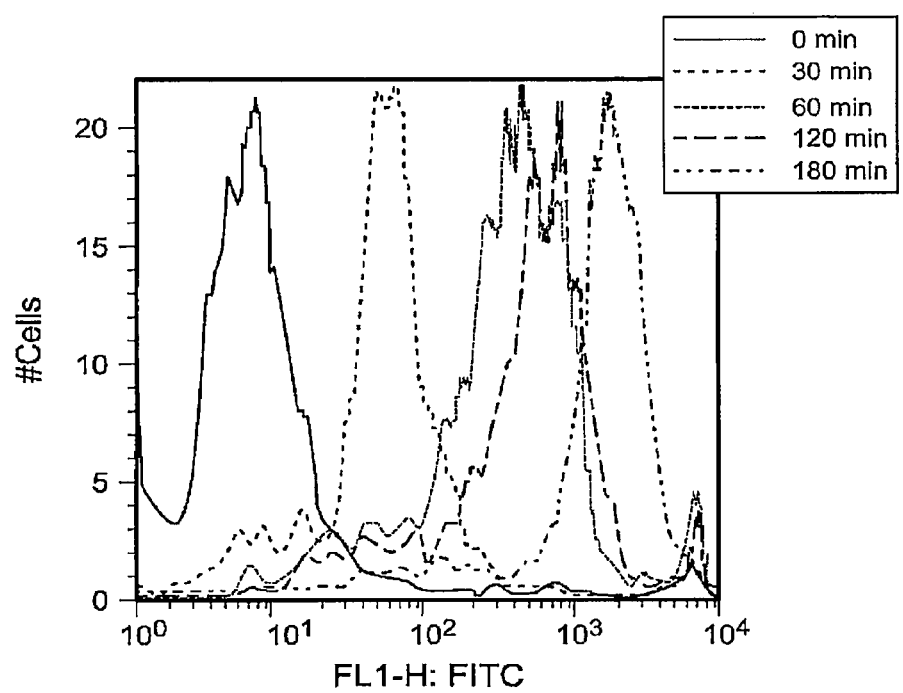
Figure 7D:
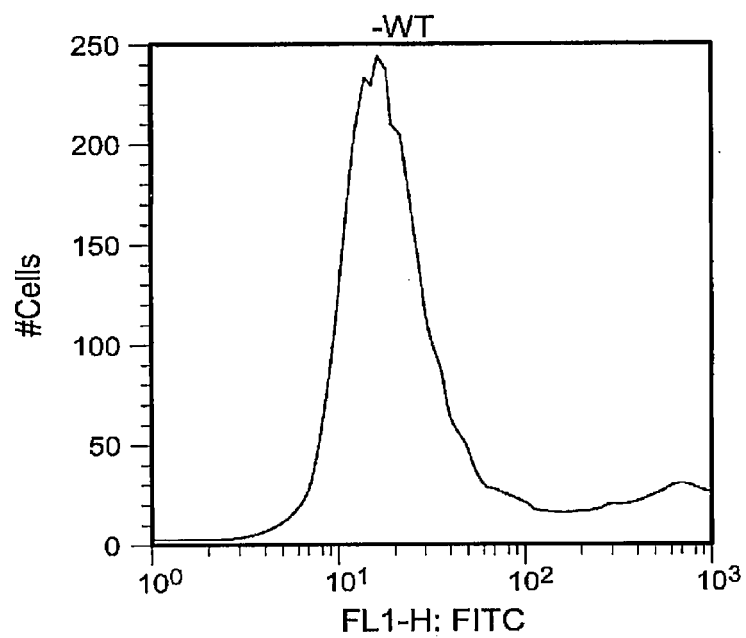
Figure 1:
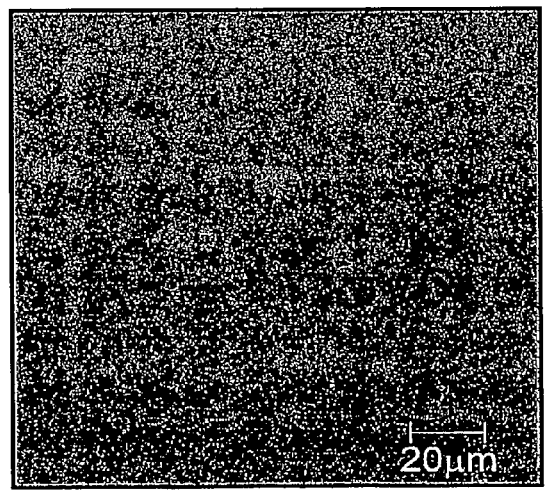
Figure 7D:
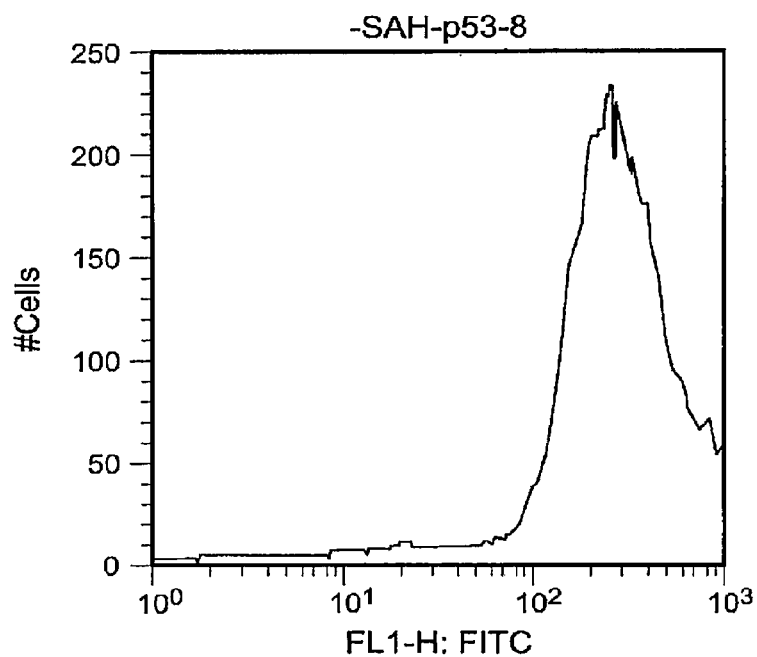
Figure 2:
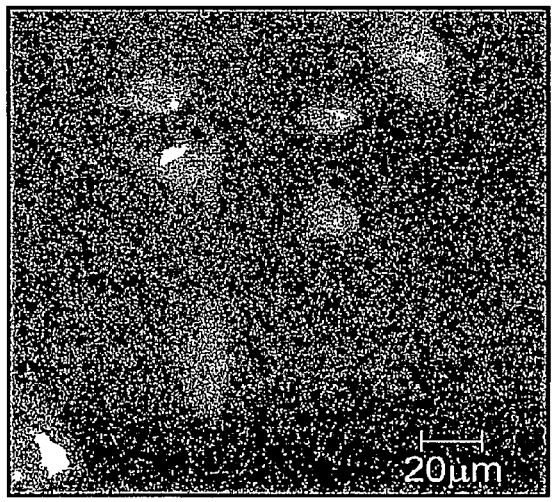
Figure 7D:
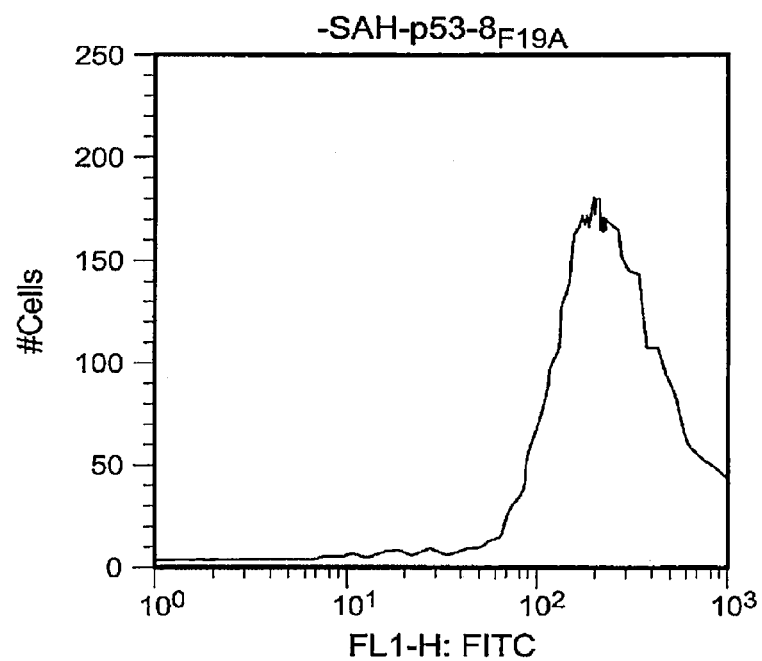

We found that the initial SAH-p53 compounds generated were incapable of penetrating intact Jurkat T-cells (FIG. 1B and FIG. 6). We noted that SAH-p53s 1-4 were negatively charged (−2) at physiological pH. Positive charge is a characteristic feature of certain classes of cell penetrating peptides.[11] In developing a second generation of compounds, we replaced aspartic and glutamic acids with asparagines and glutamines to adjust peptide charge and mutated select amino acids previously reported to participate in p53 nuclear export (L14Q) and ubiquitylation (K24R)[4, 12] (FIG. 1B). SAH-p53s 5-8 exhibited a 2-8.5 fold enhancement in α-helical content, retained high binding affinity for HDM2, and demonstrated time- and temperature-dependent cellular uptake by FACS and confocal microscopy (FIGS. 1B, 1E, 1F and 7). Cell viability assays using RKO or SJSA-1 cancer cells exposed to SAH-p53 peptides indicated that SAH-p53-8, which contained point mutations in both nuclear export and ubiquitylation sites, was the only structurally-stabilized, cell-permeable, and high affinity HDM2 binder that adversely affected cell viability (FIGS. 1B and 4A).

Figure 2:
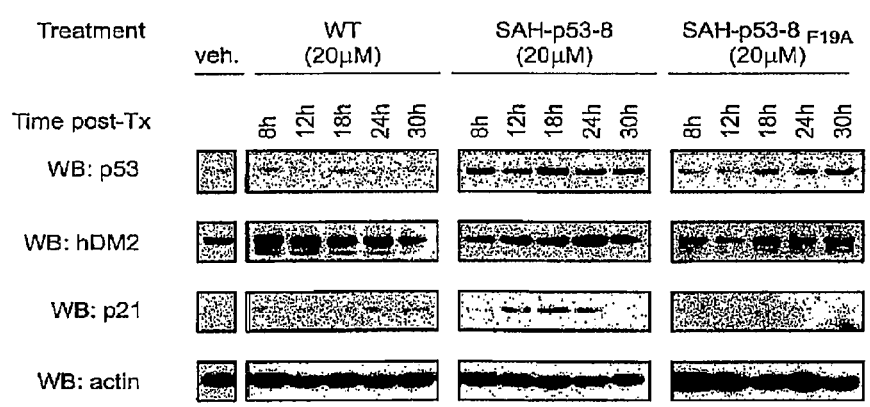
FIG. 2 SAH-p53-8 Reactivates the p53 Transcriptional Pathway. HDM2 overexpressing SJSA-1 cells were exposed to the indicated peptides and Western analyses for p53, HDM2 and p21 were performed at 8-30 h of treatment.

To determine if HDM2-targeting by SAH-p53-8 could specifically restore native p53 levels; we treated SJSA-1 cells with wild-type, 8, and $8_{F19A}$ peptides for 8-30 hours and monitored p53 protein levels by Western analysis (FIG. 2). Cells exposed to SAH-p53-8 demonstrated increased p53 proteins levels that peaked at 18 hours post-treatment. p53 resuppression by 24 hours correlated with the time-dependent upregulation of HDM2 by p53, consistent with an intact p53-HDM2 counter-regulatory mechanism.[13] SAH-p53-8 likewise induced upregulation of the cyclin-dependent kinase inhibitor p21.[14] p21 upregulation in cells treated with 8 was detected at 12 hours, reaching peak levels at 18 hours. Baseline levels were restored by 30 hours, consistent with resuppression of native p53. HDM2 and p21 levels were unchanged in SJSA-1 cells treated with wild-type or $8_{F19A}$, highlighting the specificity of SAH-p53-8 modulation of the p53 signaling pathway.

Figure 3A:
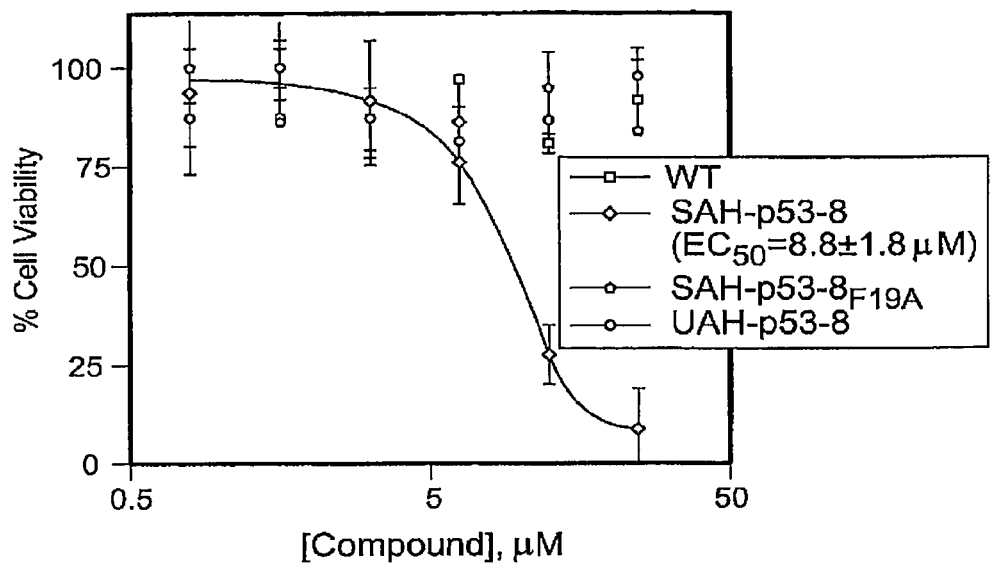
FIG. 3 Reactivation of Apoptosis in SAH-p53-8-treated SJSA-1 Cells. SAH-p53-8 demonstrated specific, dose-dependent cytotoxicity and apoptosis induction. Cell viability assay of SJSA-1 cells treated with SAH-p53 peptides (A). Caspase-3 activation assay of SJSA-1 cells treated with SAH-p53 peptides (B). Comparison of caspase-3 activation in SJSA-1, HCT-116 $p53^{+/+}$, and HCT-116 $p53^{-/-}$ cells treated with SAH-p53-peptides (25 μM) (C).
Figure 3B:
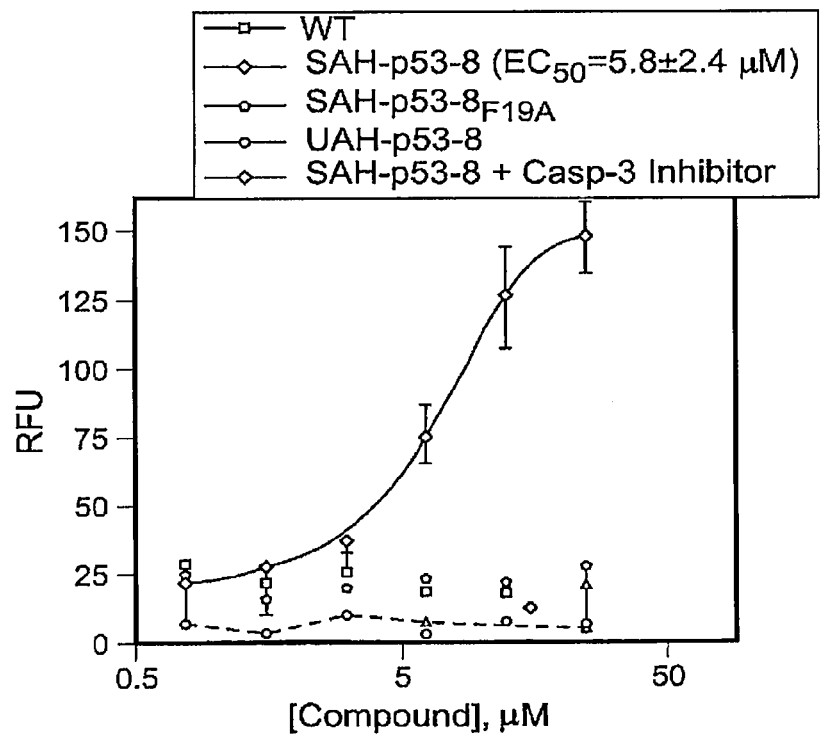
Figure 3C:
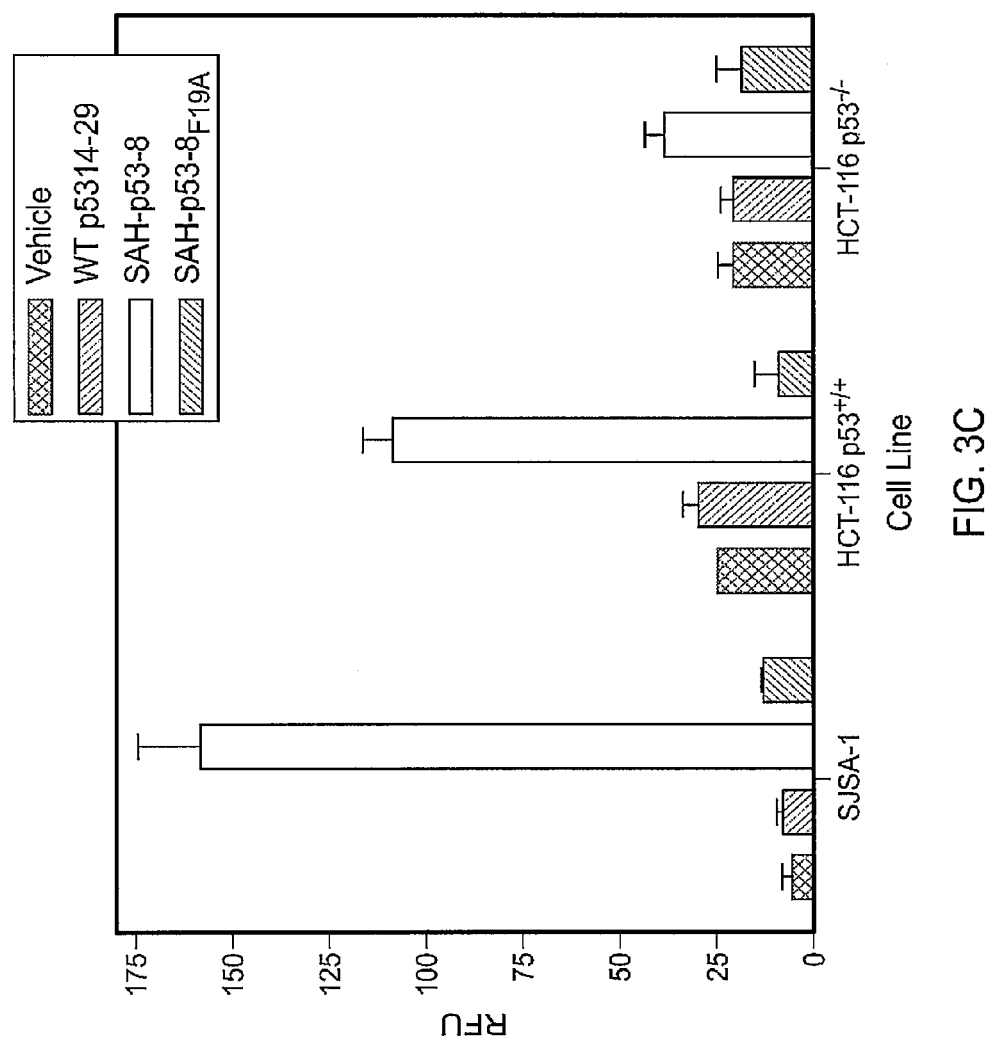
Figure 3:
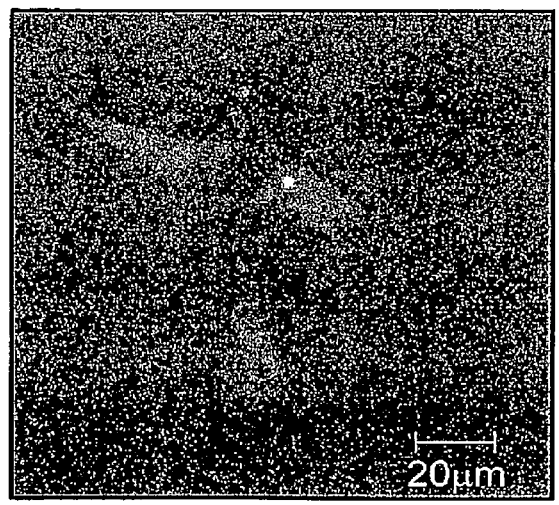

To examine whether SAH-p53-8-mediated stabilization of native p53 could inhibit cancer cells by reactivating the apoptotic pathway, we conducted viability and caspase-3 assays using SJSA-1 cells exposed to wild-type, 8, and $8_{F19A}$ for 24 hours (FIG. 3). Whereas the wild-type and $S_{F19A}$ peptides had no effect on cell viability, SAH-p53-8 exhibited dose-dependent inhibition of SJSA-1 cell viability ($EC_{50}$=8.8 μM) (FIG. 3A). Caspase-3 activation by fluorescence monitoring of the cleaved caspase-3 substrate Ac-DEVD-AMC[15] ('DEVD' disclosed as SEQ ID NO: 7) showed that neither the wild-type nor the $8_{F19A}$ peptides had any effect; however, 8 triggered dose-dependent caspase-3 activation ($EC_{50}$=5.8 μM) that was blocked by DEVD-CHO ('DEVD' disclosed as SEQ ID NO: 7), a specific caspase-3 inhibitor, demonstrating that SAH-p53-8 specifically inhibited cell viability by activating apoptosis in HDM2-overexpressing SJSA-1 cells (FIG. 3B). As can be seen from FIG. 3C, the SAH-p53-8-meidated inhibition of cell viability observed in SJSA-1 cells was also observed in HCT 116 cells, a colon cancer cell line, but not in an HCT 116 cell line variant lacking p53 (HCT 116 p53$^{-/-}$.

Figure 8:
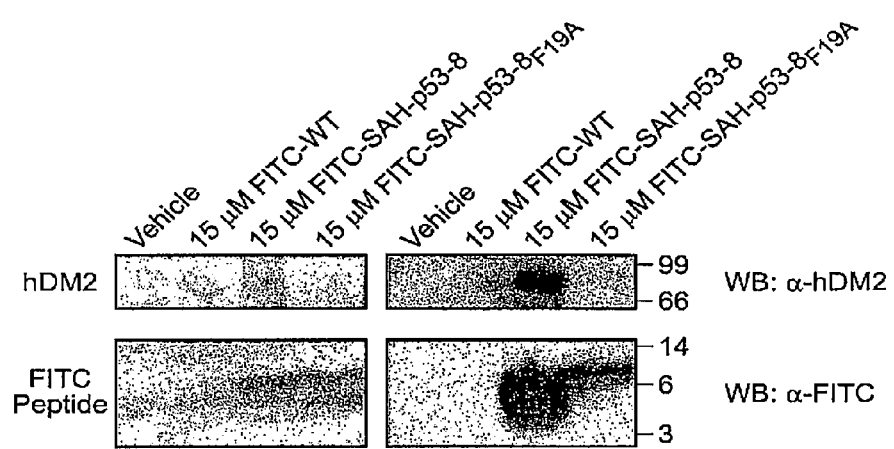
FIG. 8 SJSA-1 cells were incubated with FITC-peptides followed by lysis and anti-FITC pull down. Native HDM2 co-immununoprecipitated with FITC-SAH-p53-8 but not with wild-type or mutant SAH-p53-$8_{F19A}$ peptides. Left: silver stained gel; right: Western Blots.

The identification of multiple organic compounds and p53 peptidomimetics with anti-HDM2 activity[8, 16] holds promise for achieving clinical benefit from manipulating the p53 pathway. By generating a stapled peptide-based HDM2 inhibitor, we have documented an in situ interaction between SAH-p53-8 and HDM2 (FIG. 8), confirming that its pro-apoptotic activity derives from restoration of the p53 pathway.

Figure 9:
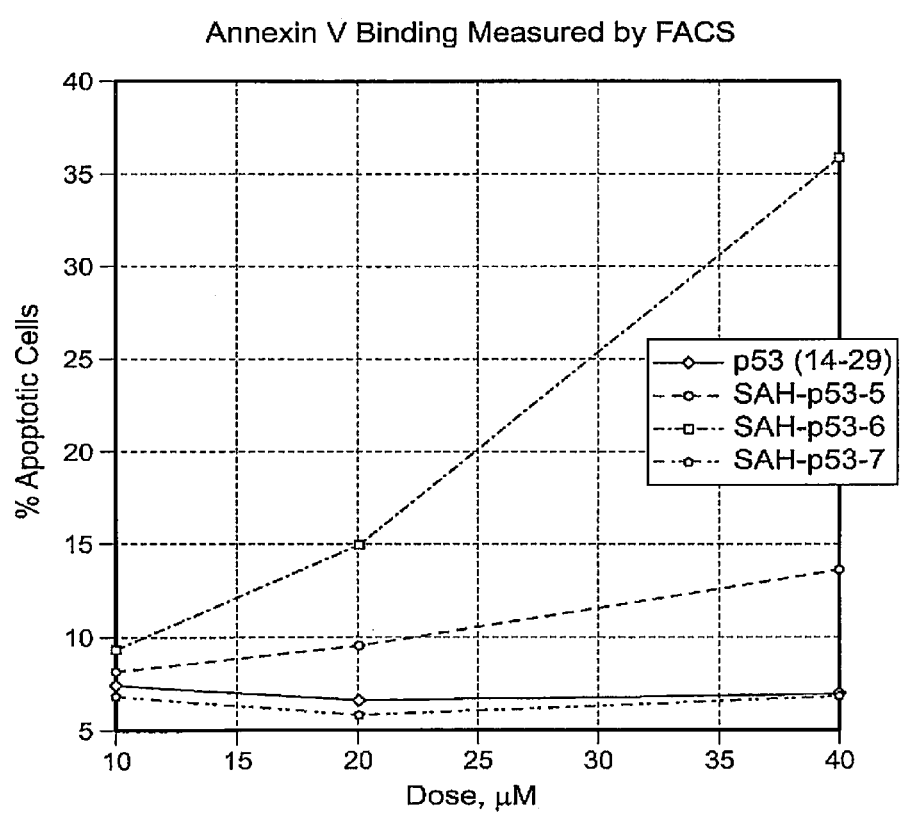
FIG. 9 Annexin V binding as an indicator of apoptosis. RKO cells were treated with peptides at different doses for 24 hours followed by staining with propidium iodide and FITC-tagged annexin V. Apoptosis induction was quantified by FACS and the data analyzed with FloJo software.

RKO cells were treated with peptides at different doses for 24 hours followed by staining with propidium iodide and FITC-tagged annexin V. Apoptosis induction was quantified by FACS and the data analyzed with FloJo software. As shown in FIG. 9, p53-SAH-p53-6 caused significant apoptosis.

Figure 10:
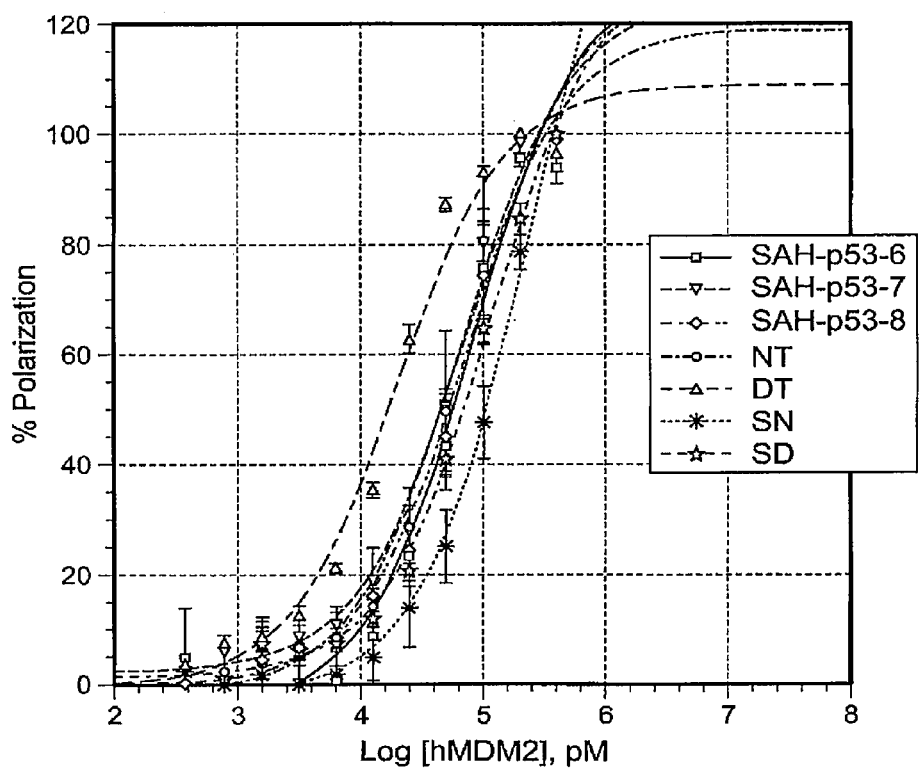
FIG. 10 Fluorescence polarization binding assay of stapled peptides. Fluoresceinated peptides (5 nM) were incubated with recombinant $HDM2_{17-125}$ (25 μM-10 μM) at room temperature. Binding activity was measured by fluorescence polarization, and Kd values were obtained by linear regression.

A fluorescence polarization binding assay was used to assess binding of peptides to $HDM2_{17-125}$. Fluoresceinated peptides (5 nM) were incubated with recombinant $HDM2_{17-125}$ (25 pM-10 μM) at room temperature. Binding activity was measured by fluorescence polarization, and $K_D$ values were obtained by linear regression. The results of this analysis are shown in FIG. 10.

Figure 11:
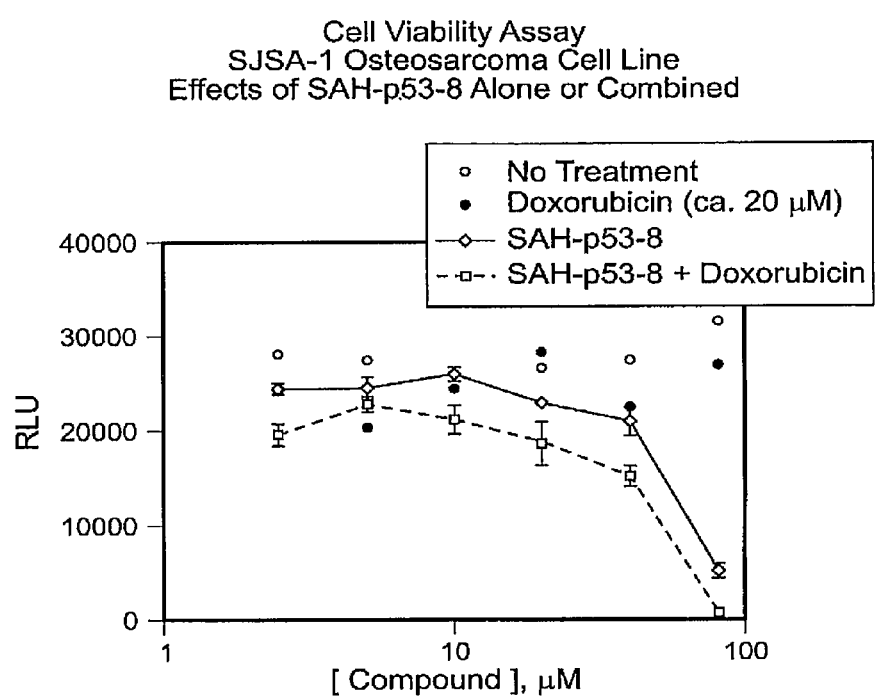
FIG. 11 Cell viability assay. SJSA-1 osteosarcoma cells were treated with different concentrations of SAH-p53-8 alone or in combination with the chemotherapeutic agent doxorubicin (20 μM) for 24 h. Cell viability was assayed by addition of CellTiter-Glo™ bioluminescence reagent and reading on a plate reader.

The effect of SAH-p53-8 alone or in combination with doxorubicin was examined as follows. SJSA-1 osteosarcoma cells were treated with different concentrations of SAH-p53-8 alone or in combination with the chemotherapeutic agent doxorubicin (20 μM) for 24 h. Cell viability was assayed by addition of CellTiter-Glo™ bioluminescence reagent and reading on a plate reader. The results of this analysis are shown in FIG. 11.

Figure 12:
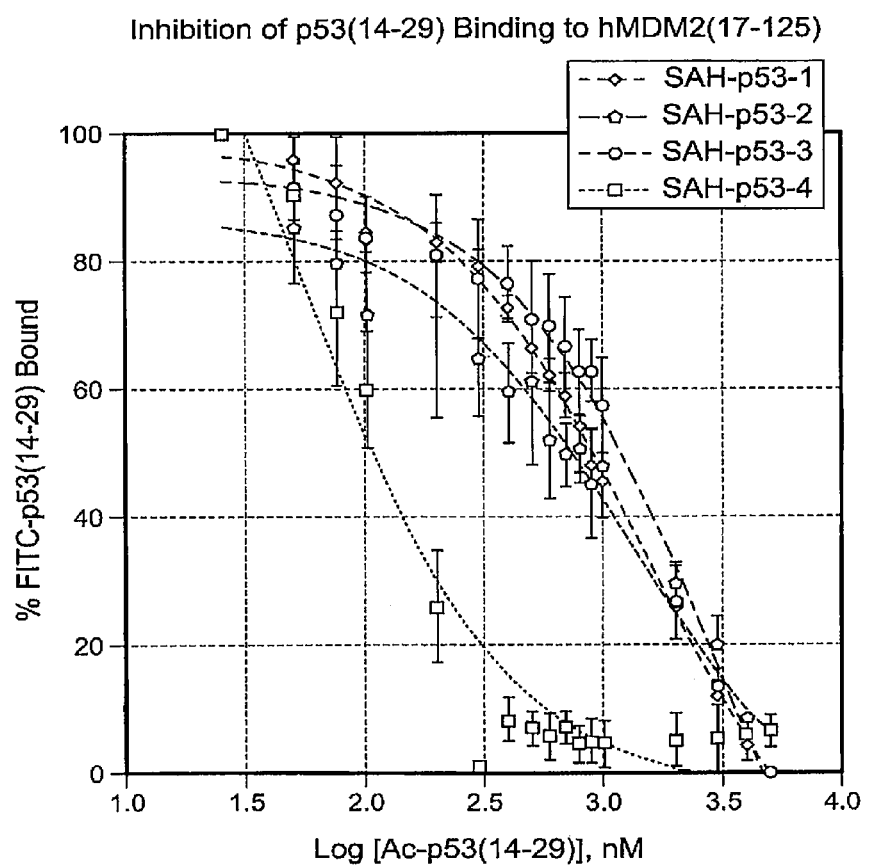
FIG. 12 Competition by fluorescence polarization. Fluoresceinated, wild type $p53_{14-29}$ (25 nM) was incubated with recombinant $HDM2_{17-125}$. Unlabeled SAH-p53s were titrated into the mixture, and displacement of the labeled ligand was measured by fluorescence polarization.

The ability of various SAH-p53s to compete with wild-type $p53_{14-29}$ for binding to $HDM2_{17-125}$ was assessed as follows. Fluoresceinated, wild type $p53_{14-29}$ (25 nM) was incubated with recombinant $HDM2_{17-125}$. Unlabeled SAH-p53s were titrated into the mixture, and displacement of the labeled ligand was measured by fluorescence polarization. The results of this analysis are shown in FIG. 12.

Figure 13:
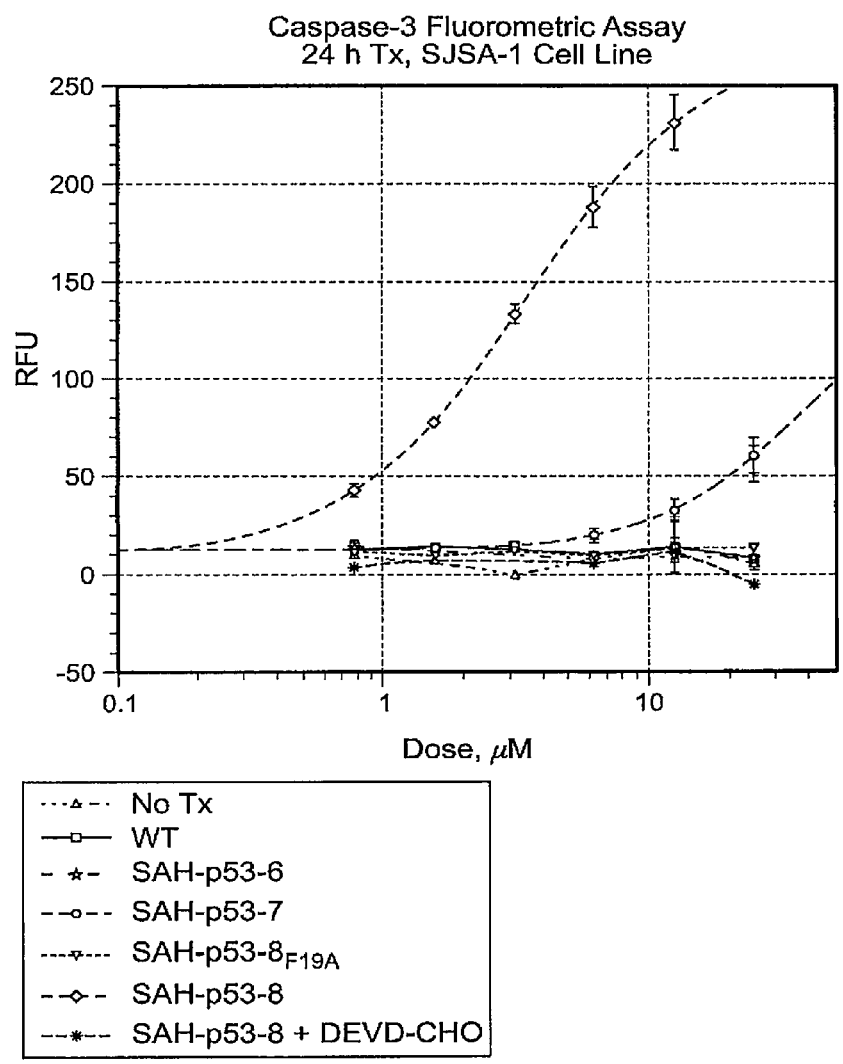
FIG. 13 Caspase-3 activation assay. SJSA-1 osteosarcoma cells were treated with different concentrations of SAH-p53s for 24 h. The cells were then exposed to a caspase-3 specific substrate (Ac-DEVD-AMC ('DEVD' disclosed as SEQ ID NO: 7)). Fluorescence as a result of cleavage was measured in a microplate reader. To determine the specificity of the activity, certain peptides were incubated alongside DEVD-CHO ('DEVD' disclosed as SEQ ID NO: 7), a substrate known to inhibit caspase-3 specifically.

The effect of various peptides on caspase-3 activation was examined as follows. SJSA-1 osteosarcoma cells were treated with different concentrations of SAH-p53s for 24 h. The cells were then exposed to a caspase-3 specific substrate. Fluorescence as a result of cleavage was measured in a microplate reader. To determine the specificity of the activity, certain peptides were incubated alongside DEVD-CHO ('DEVD' disclosed as SEQ ID NO: 7), a substrate known to inhibit caspase-3 specifically. The results of this analysis are shown in FIG. 13.

α,α-Disubstituted non-natural amino acids containing olefinic side chains of varying length can synthesized by known methods (Williams et al. 1991 *J. Am. Chem. Soc.* 113:9276; Sehafineister et al. 2000 *J. Am. Chem Soc.* 122:5891). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxiliary confers the R-alkyl-stereoisomer. Also, 8-iodooctene is used in place of 5-iodopentene Inhibitors are synthesized on a solid support using solid-phase peptide synthesis (SPPS) on MBHA resin.

Amino Acid and Peptide Synthesis

In the studies described above, Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA resin were purchased from Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine were purchased from Sigma-Aldrich and used as supplied. The synthesis of the olefinic amino acids has been described elsewhere.[1,2]

The polypeptides in the studies described above were synthesized manually using Fmoc solid phase peptide chemistry on Rink amide MBHA resin with loading levels of 0.4-0.6 mmol/g resin. The following protocol was used:

1. The Fmoc protective group was removed with 20% piperidine in NMP for 30 min.
2. The resin was washed with NMP five times.
3. The subsequent Fmoc-protected amino acid was coupled for 30 min (60 min for a cross-linker) using Fmoc-AA (10 equiv., 4 equiv. for a cross-linker), HCTU (9.9 equiv., 3.9 equiv. for a cross-linker), and DIEA (20 equiv., 7.8 equiv. for a cross-linker).
4. The resin was washed with NMP five times.
5. Repeat from step 1.

All peptides were capped with a β-alanine residue at the N-terminus. CD experiments make use of peptides that have been acetylated at the N-terminus. The acetylation reaction consisted of deprotection of the Fmoc group as outlined above, followed by reaction with acetic anhydride and DIEA. All other experiments shown make use of fluoresceinated peptides at the N-terminus. To this end, the peptides with the deprotected N-terminus were exposed to fluorescein isothiocyanate in DMF overnight in the presence of DIEA.

The ring-closing metathesis reaction was performed on the N-terminal capped peptide while still on the solid support in a disposable fitted reaction vessel. The resin was exposed to a 10 mM solution of bis(tricyclohexylphosphine)benzylidine ruthenium (IV) dichloride (Grubbs First Generation Catalyst) in 1,2-dichloroethane or dichloromethane for 2 hours. The catalyst addition and 2 hour metathesis reaction was repeated once. The resin-bound peptide was washed with $CH_2Cl_2$ three times and dried under a stream of nitrogen.

The peptide was cleaved from the resin and deprotected by exposure to Reagent K (82.5% TFA, 5% thioanisole, 5% phenol, 5% water, 2.5% 1,2-ethanedithiol) and precipitated with methyl-tert-butyl ether at 4° C. and lyophilized.

Figure 4B:
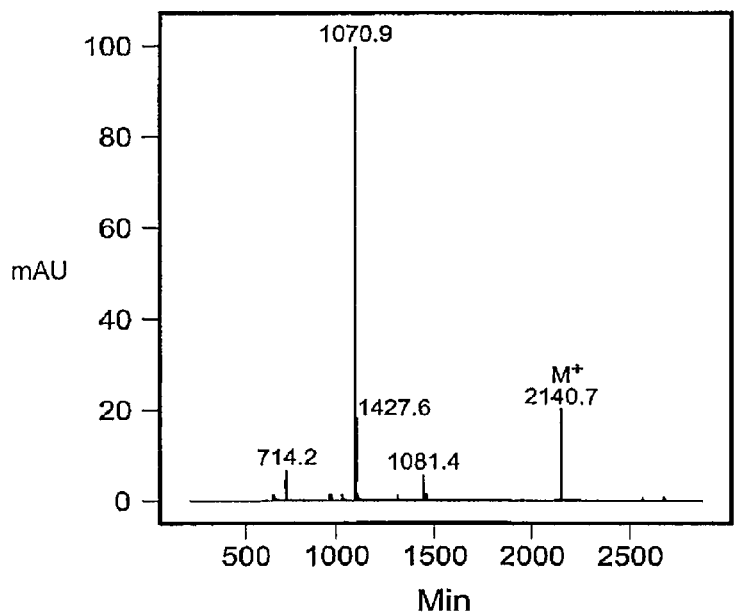

The lyophilized peptides were purified by reverse phase HPLC using a $C_{18}$ column (Agilent). The peptides were characterized by LC-MS and amino acid analysis. Mass spectra were obtained either by electrospray in positive ion mode or by MALDI-TOF. A representative LC trace and mass spectrum are shown below (FIGS. 4-A and 4-B) and the mass spectral data for all the compounds are likewise shown below in Table 2.

TABLE 2

Mass spectral data for various polypeptides

| Compound | Calculated Mass | Found Mass | Method |
| --- | --- | --- | --- |
| WT $p53_{14-29}$ | 2033.26 | 2033.12 [M + H] | MALDI-TOF |
| SAH-p53-1 | 2097.41 | 2097.14 [M + H] | MALDI-TOF |
| SAH-p53-2 | 2132.40 | 2132.84 [M + Na] | MALDI-TOF |
| SAH-p53-3 | 2089.37 | 2089.18 [M + Na] | MALDI-TOF |
| SAH-p53-4 | 2140.48 | 2140.70 [M + H] | MALDI-TOF |
| SAH-p53-5 | 2138.5 | 2139.0 [M + H] | ESI |
| SAH-p53-6 | 2165.5 | 1083.2 [M/2 + H] | ESI |
| SAH-p53-7 | 2152.4 | 1077.2 [M/2 + H] | ESI |
| SAH-p53-8 | 2180.5 | 1112.9 [M/2 + Na] | ESI |
| SAH-p53-$8_{F19A}$ | 2104.4 | 1052.9 [M + H] | ESI |
| unstapled SAH-p53-8 | 2208.5 | 2209.1 [M + H] | ESI |
| FITC-WT $p53_{14-29}$ | 2401.59 | 2402.94 [M + Na] | MALDI-TOF |

TABLE 2-continued

Mass spectral data for various polypeptides

| Compound | Calculated Mass | Found Mass | Method |
|---|---|---|---|
| FITC-SAH-p53-1 | 2466.74 | 2467.29 [M + Na] | MALDI-TOF |
| FITC-SAH-p53-2 | 2479.74 | 2479.27 [M + Na] | MALDI-TOF |
| FITC-SAH-p53-3 | 2437.72 | 2437.31 [M + Na] | MALDI-TOF |
| FITC-SAH-p53-4 | 2509.81 | 2509.10 [M + Na] | MALDI-TOF |
| FITC-SAH-p53-5 | 2401.59 | 2402.94 [M + Na] | MALDI-TOF |
| FITC-SAH-p53-6 | 2512.8 | 1257.2 [M/2 + H] | ESI |
| FITC-SAH-p53-7 | 2499.8 | 1250.6 [M/2 + H] | ESI |
| FITC-SAH-p53-8 | 2527.8 | 1286.3 [M/2 + Na] | ESI |
| FITC-SAH-p53-8$_{F19A}$ | 2451.7 | 1248.5 [M/2 + Na] | ESI |
| unstapled FITC-SAH-p53-8 | 2555.9 | 1278.5 [M/2 + Na] | ESI |

Circular Dichroism (CD) Spectroscopy

For circular dichroism (CD) spectroscopy compounds were dissolved in $H_2O$ to concentrations ranging from 10-50 µM. The spectra were obtained on a Jasco J-715 spectropolarimeter at 20° C. The spectra were collected using a 0.1 cm pathlength quartz cuvette with the following measurement parameters: wavelength, 185-255 nm; step resolution 0.1 nm; speed, 20 nm min$^{-1}$; accumulations, 6; bandwidth, 1 nm The helical content of each peptide was calculated as reported previously.[3]

Ex Vivo Protease Stability

To assess the protease stability of the peptides, fluorescinated peptides (2.5 µg) were incubated with fresh mouse serum (20 µL) at 37° C. for 0-24 hours. The level of intact fluoresceinated compound was determined by flash freezing the serum specimens in liquid nitrogen, lyophilization, extraction in 1:1 $CH_3CN$:$H_2O$ containing 0.1% TFA, followed by HPLC-based quantitation using fluorescence detection at excitation/emission settings of 495/530 nm.

Protein Production and Fluorescence Polarization

Purified HDM2$_{17-125}$ was prepared as follows. *Escherichia coli* BL21 (DE3) containing the plasmid encoding HDM2$_{17-125}$ with an N-terminal hexahistidine tag (SEQ ID NO: 8) and a thrombin cleavage site were cultured in kanamycin- and chloramphenicol-containing Luria Broth and induced with 0.1 mM isopropyl β-D-thiogalactoside (IPTG). The cells were harvested after 4 hours by centrifugation for 20 min at 3200 rpm, resuspended in buffer A (20 mM Tris pH 7.4, 0.5 M NaCl) and lysed by sonication. Cellular debris was pelleted by centrifugation for 30 minutes at 15,000 rpm, and the supernatant was incubated with Ni-NTA agarose (QIAGEN) for 2 h. The resin was washed with buffer A and eluted with a gradient of imidazole ranging from 5 mM to 500 mM. The fractions containing the eluted protein were concentrated and diluted 1:1 with thrombin cleavage buffer (5 mM $CaCl_2$, 20 mM Tris pH 7.4, 1 µL ML$^{-1}$ β-mercaptoethanol, and 0.8 U mL$^{-1}$ thrombin). The cleavage reaction was incubated overnight at 4° C. The reaction was concentrated to 2 mL and purified by gel filtration using a G75 column. Purity of the protein was assessed by SDS-PAGE, FPLC and MALDI-TOF and determined to be >90%. Its identity was further confirmed by digestion followed by mass spectrometry of the resulting peptide fragments.

Fluoresceinated compounds ($L_T$=5-25 nM) were incubated with HDM2$_{17-125}$ in binding assay buffer (140 mM NaCl, 50 mM, Tris pH 8.0) at room temperature. Binding activity was measured by fluorescence polarization on a Perkin-Elmer LS50B luminescence spectrophotometer using a cuvette containing a stirbar or a Spectramax M5 Microplate Reader (Molecular Devices). $K_d$ values were determined by nonlinear regression analysis of dose response curves using Prism software 4.0 Graphpad. In the case of compounds where $L_T < K_d$ and under the assumption that $L_T \approx L_{free}$, binding isotherms were fitted to the equation $$P = P_f + \left[(P_b - P_f) \times \frac{R_T}{K_D + R_T}\right] \quad (1)$$

where P is the measured polarization value, $P_f$ is the polarization of the free fluorescent ligand, $P_b$ is the polarization of the bound ligand, and $R_T$ is the receptor/protein concentration.

With compounds where $L_T > K_d$, the assumption that $L_T \approx L_{free}$ does not hold due to ligand depletion. As such, binding isotherms were fitted to the more explicit equation $$P = P_f + (P_b - P_f)\left[\frac{(L_T + K_D + R_T) - \sqrt{(L_T + K_D + R_T)^2 - 4L_T R_T}}{2L_T}\right] \quad (2)$$

where P is the measured polarization value, $P_f$ is the polarization of the free fluorescent ligand, $P_b$ is the polarization of the bound ligand, $L_T$ is the total concentration of fluorescent ligand and $R_T$ is the receptor/protein concentration.[4] Each data point represents the average of an experimental condition performed in at least triplicate.

Flow Cytometry

Jurkat T-cell leukemia cells were grown in RPMI-1640 (Gibco) medium with 10% fetal bovine serum, 100 U mL$^{-1}$ penicillin, 100 µg mL$^{-1}$, 2 mM glutamine, 50 mM Hepes pH 7, and 50 µM β-mercaptoethanol. SJSA-1 cells were cultured in McCoy's 5A media (ATCC) supplemented with 10% fetal bovine serum and 100 U mL$^{-1}$ penicillin. Jurkat cells (50,000 cells per well) were treated with fluoresceinated peptides (10 µM) for up to 4 hours at 37° C. After washing with media, the cells were exposed to trypsin (0.25%; Gibco) digestion (30 min, 37° C.), washed with PBS, and resuspended in PBS containing 0.5 mg mL$^{-1}$ propidium iodide (BD Biosciences). Cellular fluorescence and propidium iodide positivity were analyzed using a FACSCalibur flow cytometer (Becton Dickinson) and FlowJo software (TreeStar). The identical experiment was performed with 30 min pre-incubation of cells at 4° C. followed by 4 hour incubation with fluoresceinated peptides at 4° C. to assess temperature-dependence of fluorescent labeling.

Confocal Microscopy

Jurkat T-cell leukemia cells were incubated with fluoresceinated compounds for 24 hours at 37° C. After washing with PBS, the cells were cytospun at 600 rpm for 5 minutes onto Superfrost plus glass slides (Fisher Scientific). The cells were fixed in 4% paraformaldehyde, washed with PBS, incubated with TOPRO-3 iodide (100 nM; Molecular Probes) to conterstain nuclei, treated with Vectashield mounting medium (Vector), and imaged by confocal microscopy (Bio-Rad 1024 or Nikon E800).

In a similar fashion, SJSA-1 osteosarcoma cells (1×10$^5$ cells) were incubated in with fluoresceinated compounds for 24 hours at 37° C. in Lab-Tek™-CC2 Chamber Slides (Nunc). After washing with PBS, the cells were fixed in 4% paraformaldehyde, washed with PBS, and treated with DAPI-containing (nuclear counterstain) Vectashield mounting medium (Vector), coverslipped and imaged by confocal microscopy (BioRad 1024 or Nikon E800).

Western Blotting

SJSA-1 osteosarcoma cells ($1\times10^6$) incubated at 37° C. were treated with p53 peptides (20 μM) in serum-free media for 4 hours, followed by serum replacement and additional incubation for 4-26 additional hours. The cells were lysed (20 mM Tris-HCl pH 8.0, 0.8% SDS, 1 mM PMSF, 1 U mL$^{-1}$ benzonase nuclease) and the crude lysates were clarified by brief centrifugation and total protein concentration was determined by using the Pierce BCA protein assay. Aliquots containing 5 μg of total protein were run on 4-12% Bis-Tris polyacrylamide gels (Invitrogen). Proteins were detected by chemiluminescence reagent (Perkin Elmer) using antibodies specific for p53 (DO-1 clone; Calbiochem), HDM2 (IF2 clone; EMD Biosciences), p21 (EA10 clone; Calbiochem), and β-actin (Sigma-Aldrich).

Cell Viability and Apoptosis High-Throughput Assays

SJSA-1 osteosarcoma cells ($4\times10^5$ cells per well) were incubated in 96-well plates and treated with p53 peptides in serum-free media for 4 hours, followed by serum replacement and additional incubation for 20 hours. Cell viability was assayed by addition of CellTiter-Glo™ bioluminescence reagent (Promega) and reading luminescence in a Spectramax M5 microplate reader (Molecular Devices). The extent of apoptosis was measured through the detection of caspase-3 activity by exposing the cells to a caspase-3-specific substrate (Oncogene). Fluorescence as a result of substrate cleavage was measured in a Spectramax M5 microplate reader (Molecular Devices).

Co-Immunoprecipitation of FITC-SAH-p53 Peptides and Endogenous HDM2

SJSA-1 osteosarcoma cells ($1\times10^6$) were treated with FITC-p53 peptides (15 μM) in serum-free media for 4 hours, followed by serum replacement and additional 8 hour incubation. The cells were thoroughly washed with serum-containing media and PBS and exposed to lysis buffer (50 mM Tris pH 7.6, 150 mM NaCl, 1% Triton-X100, 1 mM PMSF, 1 U mL$^{-1}$ benzonase nuclease [EMD Biosciences] and complete protease inhibitor tablet [Roche]) at room temperature. All subsequent steps were all performed at 4° C. The extracts were centrifuged, and the supernatants were incubated with protein A/G sepharose (50 μL 50% bead slurry per 0.5 mL lysates; Santa Cruz Biotechnology). The pre-cleared supernatants (500 μL) were collected after centrifugation, incubated with 10 μL of goat-anti-FITC antibody (AbCam) for 1.5 h followed by protein A/G sepharose for an additional 1.5 hours. The immunoprecipitation reactions were pelleted and washed three times with lysis buffer. The precipitated proteins were suspended in SDS-containing loading buffer, boiled, and the supernatants were processed by SDS-PAGE on 4-12% Bis-Tris gels (Invitrogen). The proteins were blotted into Immobilon-P membranes (Millipore). After blocking, the blots were incubated with either a 1:100 dilution of mouse anti-human HDM2 antibody (IF2 clone; EMD Biosciences) or a 1:200 dilution rabbit anti-FITC antibody (Zymed) in 3% BSA in PBS followed by anti-mouse or anti-rabbit horseradish peroxidase-conjugated IgG (Pharmingen). The HDM2 protein and FITC peptides were visualized using the Western Lightning™ chemiluminescence reagent (Perkin Elmer) and exposing to film. The gels were stained using a silver stain kit (Bio-Rad) following manufacturer's instructions.

Polypeptides

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

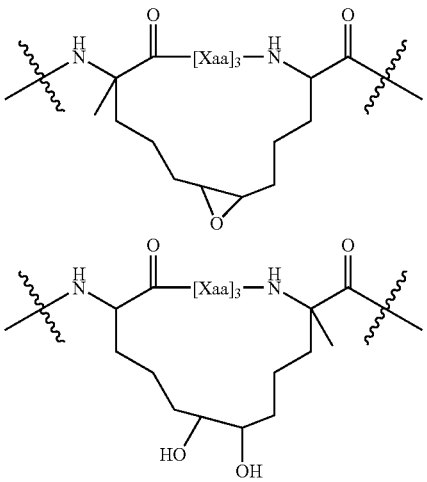

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivitization can alternatively be achieved by synthetic manipulation of the amino or carboxy terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

In the modified polypeptides one or more conventional peptide bonds replaced by a different bond that may increase the stability of the polypeptide in the body. Peptide bonds can be replaced by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O)) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. The polypeptides of the invention may also be conjugated to, for example, polyethylene glycol (PEG); alkyl groups (e.g., C1-C20 straight or branched alkyl groups); fatty acid radicals; and combinations thereof.

Methods of Treatment

The present invention provides for both prophylactic and therapeutic methods of treating a subject at risk of (or susceptible to) a disorder or having a disorder associated with reduced p53 activity. This is because the polypeptides are expected to act as inhibitors of p53 binding to HDM2 and/or HDMX. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

The polypeptides described herein can be used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease, state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The compounds (i.e., polypeptides) can act as novel therapeutic agents for controlling osteosarcomas, colon cancer, breast cancer, T cell cancers and B cell cancer. The polypeptides may also be useful for treating mucoepidermoid carcinoma, retinoblastoma and medulloblastoma. The compounds can be used to treat disorders associated with unwanted proliferation of cells having reduced activity and/or expression of p53, particularly where the cells produce at least some active p53.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Exemplary disorders include: acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), multiple mylenoma, hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Pharmaceutical Compositions and Routes of Administration

As used herein, the compounds of this invention, including the compounds of formulae described herein, are defined to include pharmaceutically acceptable derivatives or prodrugs thereof A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central-nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include alkali metal (e.g., sodium), alkaline earth metal (e.g., magnesium), ammonium and $N-(alkyl)_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, or according to the requirements of the, particular drug. The, methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional agent including for example, morphine or codeine; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic agents if present, in amounts effective for achieving a modulation of disease or disease symptoms. The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disoditun hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and δ-cyclodextrin, may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Modification of Polypeptides

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:
$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —NH(CH$_2$)$_n$C(O)—, wherein n=2-20 can be used. These alkyl linkers may further be substituted by any non-sterically hindering group such as lower alkyl (e.g., C$_1$-C$_6$ lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

Screening Assays

The invention provides methods (also referred to herein as "screening assays") for identifying polypeptides, small molecules, or bifunctional derivatives which bind to HDM2 and/or HDMX.

The binding affinity of polypeptides that bind HDM2 and/or HDMX can be measured using the methods described herein, for example, by using a titration binding assay. HDM2 and/or HDMX can be exposed to varying concentrations of a candidate compound (i.e., polypeptide) (e.g., 1 nM, 10 nM, 100 nM, 1 μM, 10 μM, 100 μM, 1 mM, and 10 mM) and binding can be measured using surface plasmon resonance to determine the Kd for binding. Additionally, the binding interactions of fluorescently-labeled SAH-p53 peptides to HDM2 and/or HDMX can be used in a competitive binding assay to screen for and identify peptides, small molecules, or bifunctional derivatives thereof that compete with FITC-SAH-p53 peptides, and further calculate Ki values for binding competition. Candidate compounds could also be screened for biological activity in vivo. Cell permeability screening assays in which fluorescently labeled candidate compounds are applied to intact cells, which are then assayed for cellular fluorescence by microscopy or high-throughput cellular fluorescence detection can also be used.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

Thus, one can expose HDM2 (e.g., purified MDM2) or HDMX (e.g., purified MDM2) purified to a test compound in the presence of a stapled p53 peptide and determining whether the test compound reduces (inhibits) binding of the stapled p53 peptide to MDM2 or MDMX. A test compound that inhibits binding is a candidate inhibitor of the interaction between p53 and MDM2 or MDMX (or both). Test compounds can be tested for their ability to inhibit binding to MDM2 and MDMX in order to identify compounds that are relatively selective for inhibit p53 binding. In some cases, nutlin-3 (CAS 548472-68-0) can be used as a control since nutlin-3 is a selective inhibitor of p53 binding to HMD2

Other Applications

A number of embodiments of the invention have been described. Nevertheless, it will be understood that various modifications may be made without departing from the spirit and scope of the invention. Accordingly, other embodiments are within the scope of the following claims.

REFERENCES (1) Kastan, M. B.; Onyekwere, O.; Sidransky, D.; Vogelstein, B.; Craig, R. W., Cancer Res. 1991, 51, 6304-6311.
(2) Wu, X.; Bayle, J. H.; Olson, D.; Levine, A. J., Genes Dev. 1993, 7, 1126-1132; Yonish-Rouach, E.; Resnftzky, D.; Lotem, J.; Sachs, L.; Kimchi, A.; Oren, M., Nature 1991, 352, 345-347; Momand, J.; Zambetti, G. P.; Olson, D. C.; George, D.; Levine, A. J., Cell 1992, 69, 1237.
(3) Levine, A. J.; Hu, W.; Feng, Z., Cell Death Differ 2006, 13, 1027; Honda, R.; Tanaka, H.; Yasuda, H., FEBS Lett. 1997, 420, 25; Tao, W.; Levine, A. J., Proc. Nat. Acad. Sci. U.S.A. 1999, 96, 3077-3080.
(4) Li, M.; Brooks, C. L.; Wu-Baer, F.; Chen, D.; Baer, R.; Gu, W., Science 2003, 302, 1972-1975.
(5) Hollstein, M.; Sidransky, D.; Vogelstein, B.; Harris, C. C., Science 1991, 253, 49-53.
(6) Chène, P., Nat. Rev. Cancer 2003, 3, 102-109.
(6a) Toledo, F.; Wahl, G. M., Int. J. Biochem. Cell Biol. 2007, 39, 1476-82.
(7) Kussie, P. H.; Gorina, S.; Marechal, V.; Elenbaas, B.; Moreau, J.; Levine, A. J.; Pavletich, N. P., Science 1996, 274, 948-953.
(8) Sakurai, K.; Chung, H. S.; Kahne, D., J. Am. Chem. Soc. 2004, 126, 16288-16289; Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A., Science 2004, 303, 844-848.
(9) Lin, J.; Chen, J.; Elenbaas, B.; Levine, A. J., Genes Dev. 1994, 8, 1235-1246.
(10) Schafineister, C. E.; Po, J.; Verdine, G. L., J. Am. Chem. Soc. 2000, 122, 5891-5892; Walensky, L. D.; Kung, A. L.; Escher, I.; Malia, T. J.; Barbuto, S.; Wright, R. D.; Wagner, G.; Verdine, G. L.; Korsmeyer, S. J.; Science, 2004, 305, 1466-1470.
(11) Vivès, E.; Lebleu, B., The Tat-Derived Cell-Penetrating Peptide. In Cell-Penetrating Peptides Processes and Applications, Langel, Ü., Ed. CRC Press: Boca Raton, 2002; pp 3-21.
(12) Zhang, Y.; Xiong, Y., Science 2001, 292, 1910-1915.
(13) Barak, Y.; Juven, T.; Haffner, R.; Oren, M., EMBO J. 1993, 12, 461-468; Juven, T.; Barak, Y.; Zauberman, A.; George, D. L.; Oren, M., Oncogene 1993, 8, 3411-3416.
(14) Dulic, V.; Kaufmann, W. K.; Wilson, S. J.; Tisty, T. D.; Lees, E.; Harper, J. W.; Elledge, S. J.; Reed, S. I., Cell 1994, 76, 1013; El-Deiry, W. S.; Tokino, T.; Velculescu, V. E.; Levy, D. B.; Parsons, R.; Trent, J. M.; Lin, D.; Mercer, W. E.; Kinzler, K. W.; Vogelstein, B., Cell 1993, 75, 817.
(15) Pochampally, R.; Fodera, B.; Chen, L.; Lu, W.; Chen, J., J. Biol. Chem. 1999, 274, 15271-15277.
(16) Duncan, S. J.; Gruschow, S.; Williams, D. H.; McNicholas, C.; Purewal, R.; Hajek, M.; Gerlitz, M.; Martin, S.; Wrigley, S. K.; Moore, M., J. Am. Chem. Soc. 2001, 123, 554-560; Chène, P.; Fuchs, J.; Bohn, J.; Garcia-Echeverria, C.; Furet, P.; Fabbro, D., J. Mol. Biol. 2000, 299, 245; Sakurai, K.; Schubert, C.; Kahne, D., J. Am. Chem. Soc. 2006, 128, 11000-11001; Kritzer, J. A.; Hodsdon, M. E.; Schepartz, A., J. Am. Chem. Soc. 2005, 127, 4118-4119; Kritzer, J. A.; Lear, J. D.; Hodsdon, M. E.; Schepartz, A., J. Am. Chem. Soc. 2004, 126, 9468-9469; Wasylyk, C.; Salvi, R.; Argentini, M.; Dureuil, C.; Delumeau, I.; Abecassis, J.; Debussche, L.; Wasylyk, B., Oncogene 1999, 18, 1921-1934; Garcia-Echeverria, C; Chène, P.; Blommers, M. J. J.; Furet, P., J. Med. Chem. 2000, 43, 3205-3208; Grasberger, B. L., et al., J. Med. Chem. 2005, 48, 909-912.

The invention claimed is:

1. A modified polypeptide of Formula (I)

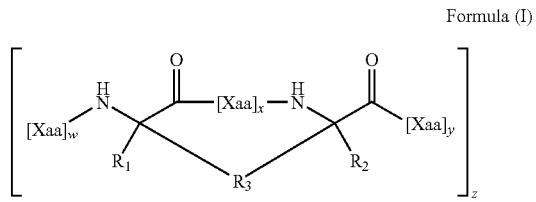

Formula (I)

or a pharmaceutically acceptable salt thereof,
wherein:
each $R_1$ and $R_2$ are independently H, alkyl, alkenyl, alkynyl, arylalkyl, cycloalkylalkyl, heteroarylalkyl, or heterocyclylalkyl;
each $R_3$ is independently alkylene, alkenylene, alkynylene, or $[R_4—K—R_4']_n$, each of which is substituted with 0-6 $R_5$;
each $R_4$ and $R_4'$ are independently alkylene, alkenylene, or alkynylene;
each $R_5$ is independently halo, alkyl, $OR_6$, $N(R_6)_2$, $SR_6$, $SOR_6$, $SO_2R_6$, $CO_2R_6$, $R_6$, a fluorescent moiety, or a radioisotope;
each K is independently O, S, SO, $SO_2$, CO, $CO_2$, $CONR_6$, or

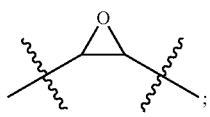

each $R_6$ is independently H, alkyl, or a therapeutic agent;
each n is independently an integer from 1-4;
x is 6;
each y is independently an integer from 1-15;
each w is independently an integer from 3 to 15;
z is an integer from 1-10; and
each Xaa is independently an amino acid;
wherein the modified polypeptide or the pharmaceutically acceptable salt thereof comprises at least 8 contiguous amino acids of $Leu_1$ $Ser_2$ $Gln_3$ $Glu_4$ $Thr_5$ $Phe_6$ $Ser_7$ $Asp_8$ $Leu_9$ $Trp_{10}$ $Lys_{11}$ $Leu_{12}$ $Leu_{13}$ $Pro_{14}$ $Glu_{15}$ $Asn_{16}$ (SEQ ID NO:2), wherein the side chains of $Ser_7$ and $Pro_{14}$ are replaced by the linking group $R_3$, and none or up to 6 amino acids other than $Phe_6$, $Trp_{10}$ and $Leu_{13}$ are independently replaced by any other amino acid.

2. The modified polypeptide or the pharmaceutically acceptable salt thereof of claim 1, wherein the modified polypeptide or the pharmaceutically acceptable salt thereof binds to HDM2.

3. The modified polypeptide or the pharmaceutically acceptable salt thereof of claim 1, wherein each $R_3$ is independently an alkenylene containing a single double bond, and both $R_1$ and $R_2$ are H.

4. The modified polypeptide or the pharmaceutically acceptable salt thereof of claim 1, wherein the modified polypeptide or the pharmaceutically acceptable salt thereof does not have a net negative charge at pH 7.

5. The modified polypeptide or the pharmaceutically acceptable salt thereof of claim 4, wherein the modified polypeptide or the pharmaceutically acceptable salt thereof comprises at least one amino acid that has a positive charge at pH 7, wherein the at least one amino acid is at either: (a) amino terminal to $Leu_1$ or the amino acid substituted for $Leu_1$ or (b) carboxy terminal to $Asn_{16}$ or the amino acid substituted for $Asn_{16}$.

6. The modified polypeptide or the pharmaceutically acceptable salt thereof of claim 1, wherein $R_1$ and $R_2$ are each independently H or $C_1$-$C_6$ alkyl.

7. The modified polypeptide or the pharmaceutically acceptable salt thereof of claim 1, wherein each $R_3$ is independently $C_8$ alkylene.

8. The modified polypeptide or the pharmaceutically acceptable salt thereof of claim 1, wherein each $R_3$ is independently $C_{11}$ alkylene.

9. The modified polypeptide or the pharmaceutically acceptable salt thereof of claim 1, wherein each $R_3$ is independently alkenylene.

10. The modified polypeptide or the pharmaceutically acceptable salt thereof of claim 1, wherein each $R_3$ is independently $C_8$ alkenylene.

11. The modified polypeptide or the pharmaceutically acceptable salt thereof of claim 1, wherein each $R_3$ is independently $C_{11}$ alkenylene.

12. The modified polypeptide or the pharmaceutically acceptable salt thereof of claim 1, wherein each $R_3$ is independently a straight chain alkylene, alkenylene, or alkynylene.

13. The modified polypeptide or the pharmaceutically acceptable salt thereof of claim 1, further comprising a copolymer of lactic and glycolic acid.

14. The modified polypeptide or the pharmaceutically acceptable salt thereof of claim 1, further comprising an amino-terminal fatty acid.

15. The modified polypeptide or the pharmaceutically acceptable salt thereof of claim 1, further comprising a biotin moiety.

16. The modified polypeptide or the pharmaceutically acceptable salt thereof of claim 1, wherein the modified polypeptide or the pharmaceutically acceptable salt thereof is capable of being transported through a cell membrane.

17. The modified polypeptide or the pharmaceutically acceptable salt thereof of claim 1, further comprising a PEG, a tat protein, an affinity label, a targeting moiety, a fatty acid-derived acyl group, a biotin moiety, or a fluorescent probe.

18. The modified polypeptide or the pharmaceutically acceptable salt thereof of claim 17, wherein the fluorescent probe is fluorescein or rhodamine.

19. The modified polypeptide or the pharmaceutically acceptable salt thereof of claim 17, wherein the fluorescent probe is linked via a thiocarbamate or carbamate linkage to the modified polypeptide or the pharmaceutically acceptable salt thereof.

20. The modified polypeptide or the pharmaceutically acceptable salt thereof of claim 1, wherein each $R_1$ and $R_2$ are independently $C_1$-$C_3$ alkyl.

21. The modified polypeptide or the pharmaceutically acceptable salt thereof of claim 1, wherein both $R_1$ and $R_2$ are methyl.

22. The modified polypeptide or the pharmaceutically acceptable salt thereof of claim 1, further comprising a targeting moiety.

23. The modified polypeptide or the pharmaceutically acceptable salt thereof of claim 1, wherein the modified polypeptide or the pharmaceutically acceptable salt thereof binds to HDMX.

24. The modified polypeptide or the pharmaceutically acceptable salt thereof of claim 1, wherein the modified polypeptide or the pharmaceutically acceptable salt thereof binds to HDMX and HDM2.

25. The modified polypeptide or the pharmaceutically acceptable salt thereof of claim 1, 2, 3, 6, 7, 8, 9, 10, 11, 12, 20, 21, 23 or 24, wherein z is 1.

* * * * *

UNITED STATES PATENT AND TRADEMARK OFFICE
CERTIFICATE OF CORRECTION

| | | |
|---|---|---|
| PATENT NO. | : 8,889,632 B2 | Page 1 of 1 |
| APPLICATION NO. | : 12/525123 | |
| DATED | : November 18, 2014 | |
| INVENTOR(S) | : Fredrico Bernal et al. | |

It is certified that error appears in the above-identified patent and that said Letters Patent is hereby corrected as shown below:

In the specification

Col. 1, before line 13, please insert the below paragraph:

-- STATEMENT AS TO FEDERALLY SPONSORED RESEARCH

This invention was made with support of the United States government under Grant No. CA103510-0 by the National Institute of Health (NIH); Grant No. R37CA050239 by the National Institute of Health (NIH); Grant No. K08HL074049 by the National Heart Lung and Blood Institute (NHLBI); and the Ruth L. Kirschstein National Research Service Award (NRSA) No. F32CA103510 by the National Institute of Health (NIH). The government has certain rights in the invention. --

Signed and Sealed this
Tenth Day of November, 2015

Michelle K. Lee
*Director of the United States Patent and Trademark Office*

SEQUENCE LISTING

<160> NUMBER OF SEQ ID NOS: 53

<210> SEQ ID NO 1
<211> LENGTH: 393
<212> TYPE: PRT
<213> ORGANISM: Homo sapiens

<400> SEQUENCE: 1

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
        210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
        290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

```
Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 2
<211> LENGTH: 16
<212> TYPE: PRT
<213> ORGANISM: Homo sapiens

<400> SEQUENCE: 2

Leu Ser Gln Glu Thr Phe Ser Asp Leu Trp Lys Leu Leu Pro Glu Asn
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 3

Xaa Ser Gln Xaa Thr Phe Xaa Xaa Leu Trp Xaa Leu Leu Xaa Xaa Asn
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 4

Gln Xaa Thr Phe Xaa Xaa Leu Trp Xaa Leu Leu
1               5                   10

<210> SEQ ID NO 5
```

-continued

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Ser Asn Leu Trp Arg Leu Leu Pro Gln Asn
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Gln Gln Thr Phe Ser Asn Leu Trp Arg Leu Leu Pro Gln Asn
1               5                   10                  15

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Glu Val Asp
1

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 16
<212> TYPE: PRT
<213> ORGANISM: Homo sapiens

<400> SEQUENCE: 9

Leu Ser Gln Glu Thr Phe Ser Asp Leu Trp Lys Leu Leu Pro Glu Asn
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Any uncross-linked or cross-linked amino acid
      in R-or S- orientation
<220> FEATURE:
```

```
<221> NAME/KEY: MOD_RES
<222> LOCATION: (16)..(16)
<223> OTHER INFORMATION: Any uncross-linked or cross-linked amino acid
      in R-or S- orientation

<400> SEQUENCE: 10

Leu Ser Gln Glu Thr Phe Ser Asp Xaa Trp Lys Leu Leu Pro Glu Xaa
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any uncross-linked or cross-linked amino acid
      in R-or S- orientation
<220> FEATURE:
<221> NAME/KEY: MOD_RES
<222> LOCATION: (12)..(12)
<223> OTHER INFORMATION: Any uncross-linked or cross-linked amino acid
      in R-or S- orientation

<400> SEQUENCE: 11

Leu Ser Gln Glu Xaa Phe Ser Asp Leu Trp Lys Xaa Leu Pro Glu Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any uncross-linked or cross-linked amino acid
      in R-or S- orientation
<220> FEATURE:
<221> NAME/KEY: MOD_RES
<222> LOCATION: (11)..(11)
<223> OTHER INFORMATION: Any uncross-linked or cross-linked amino acid
      in R-or S- orientation

<400> SEQUENCE: 12

Leu Ser Gln Xaa Thr Phe Ser Asp Leu Trp Xaa Leu Leu Pro Glu Asn
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 13
```

Leu Ser Gln Glu Thr Phe Xaa Asp Leu Trp Lys Leu Leu Xaa Glu Asn
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 14

Leu Ser Gln Glu Thr Phe Xaa Asn Leu Trp Lys Leu Leu Xaa Gln Asn
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 15

Leu Ser Gln Gln Thr Phe Xaa Asn Leu Trp Arg Leu Leu Xaa Gln Asn
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 16

Gln Ser Gln Gln Thr Phe Xaa Asn Leu Trp Lys Leu Leu Xaa Gln Asn
1               5                   10                  15

<210> SEQ ID NO 17
<211> LENGTH: 16
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 17

Gln Ser Gln Gln Thr Phe Xaa Asn Leu Trp Arg Leu Leu Xaa Gln Asn
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 18

Gln Ser Gln Gln Thr Ala Xaa Asn Leu Trp Arg Leu Leu Xaa Gln Asn
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 19

Gln Ser Gln Gln Thr Phe Xaa Asn Leu Trp Arg Lys Lys Xaa Gln Asn
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Beta-alanine or not present
<220> FEATURE:
<221> NAME/KEY: MOD_RES
<222> LOCATION: (3)..(3)
<223> OTHER INFORMATION: Any uncross-linked or cross-linked amino acid
      in R-or S- orientation
<220> FEATURE:
<221> NAME/KEY: MOD_RES
<222> LOCATION: (10)..(10)
<223> OTHER INFORMATION: Any uncross-linked or cross-linked amino acid
      in R-or S- orientation

<400> SEQUENCE: 20

Xaa Leu Xaa Gln Glu Thr Phe Ser Asp Xaa Trp Lys Leu Leu Pro Glu
1               5                   10                  15

Asn

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (5)..(5)
<223> OTHER INFORMATION: Any uncross-linked or cross-linked amino acid
      in R-or S- orientation
<220> FEATURE:
<221> NAME/KEY: MOD_RES
<222> LOCATION: (12)..(12)
<223> OTHER INFORMATION: Any uncross-linked or cross-linked amino acid
      in R-or S- orientation

<400> SEQUENCE: 21

Xaa Leu Ser Gln Xaa Thr Phe Ser Asp Leu Trp Xaa Leu Leu Pro Glu
1               5                   10                  15

Asn

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (6)..(6)
<223> OTHER INFORMATION: Any uncross-linked or cross-linked amino acid
      in R-or S- orientation
<220> FEATURE:
<221> NAME/KEY: MOD_RES
<222> LOCATION: (13)..(13)
<223> OTHER INFORMATION: Any uncross-linked or cross-linked amino acid
      in R-or S- orientation

<400> SEQUENCE: 22

Xaa Leu Ser Gln Glu Xaa Phe Ser Asp Leu Trp Lys Xaa Leu Pro Glu
1               5                   10                  15

Asn
```

```
<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 23

Xaa Leu Ser Gln Glu Thr Xaa Ser Asp Leu Trp Lys Leu Xaa Pro Glu
1               5                   10                  15

Asn

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 24

Xaa Leu Ser Gln Glu Thr Phe Xaa Asp Leu Trp Lys Leu Leu Xaa Glu
1               5                   10                  15

Asn

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (3)..(3)
<223> OTHER INFORMATION: Any uncross-linked or cross-linked amino acid
      in R-or S- orientation
<220> FEATURE:
<221> NAME/KEY: MOD_RES
```

```
<222> LOCATION: (9)..(9)
<223> OTHER INFORMATION: Any uncross-linked or cross-linked amino acid
      in R-or S- orientation
<220> FEATURE:
<221> NAME/KEY: MOD_RES
<222> LOCATION: (16)..(16)
<223> OTHER INFORMATION: Any uncross-linked or cross-linked amino acid
      in R-or S- orientation

<400> SEQUENCE: 25

Xaa Leu Xaa Gln Glu Thr Phe Ser Xaa Leu Trp Lys Leu Leu Pro Xaa
1               5                   10                  15

Asn

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (10)..(10)
<223> OTHER INFORMATION: Any uncross-linked or cross-linked amino acid
      in R-or S- orientation
<220> FEATURE:
<221> NAME/KEY: MOD_RES
<222> LOCATION: (17)..(17)
<223> OTHER INFORMATION: Any uncross-linked or cross-linked amino acid
      in R-or S- orientation

<400> SEQUENCE: 26

Xaa Leu Ser Gln Glu Thr Phe Ser Asp Xaa Trp Lys Leu Leu Pro Glu
1               5                   10                  15

Xaa

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 27

Xaa Leu Ser Gln Gln Thr Phe Xaa Asp Leu Trp Lys Leu Leu Xaa Glu
1               5                   10                  15

Asn

<210> SEQ ID NO 28
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 28

Xaa Leu Ser Gln Glu Thr Phe Xaa Asp Leu Trp Lys Leu Leu Xaa Gln
1               5                   10                  15

Asn

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 29

Xaa Leu Ser Gln Gln Thr Phe Xaa Asp Leu Trp Lys Leu Leu Xaa Gln
1               5                   10                  15

Asn

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation
```

<400> SEQUENCE: 30

Xaa Leu Ser Gln Glu Thr Phe Xaa Asn Leu Trp Lys Leu Leu Xaa Gln
1               5                   10                  15

Asn

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 31

Xaa Leu Ser Gln Gln Thr Phe Xaa Asn Leu Trp Lys Leu Leu Xaa Gln
1               5                   10                  15

Asn

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 32

Xaa Leu Ser Gln Gln Thr Phe Xaa Asn Leu Trp Arg Leu Leu Xaa Gln
1               5                   10                  15

Asn

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 33

Xaa Gln Ser Gln Gln Thr Phe Xaa Asn Leu Trp Lys Leu Leu Xaa Gln
1               5                   10                  15

Asn

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 34

Xaa Gln Ser Gln Gln Thr Phe Xaa Asn Leu Trp Arg Leu Leu Xaa Gln
1               5                   10                  15

Asn

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 35

Xaa Gln Ser Gln Gln Thr Ala Xaa Asn Leu Trp Arg Leu Leu Xaa Gln
1               5                   10                  15

Asn
```

```
<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (6)..(6)
<223> OTHER INFORMATION: Any uncross-linked or cross-linked amino acid
      in R-or S- orientation
<220> FEATURE:
<221> NAME/KEY: MOD_RES
<222> LOCATION: (13)..(13)
<223> OTHER INFORMATION: Any uncross-linked or cross-linked amino acid
      in R-or S- orientation

<400> SEQUENCE: 36

Xaa Gln Gln Thr Phe Xaa Asp Leu Trp Arg Leu Leu Xaa Glu Asn
1               5                   10                  15

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (6)..(6)
<223> OTHER INFORMATION: Any uncross-linked or cross-linked amino acid
      in R-or S- orientation
<220> FEATURE:
<221> NAME/KEY: MOD_RES
<222> LOCATION: (13)..(13)
<223> OTHER INFORMATION: Any uncross-linked or cross-linked amino acid
      in R-or S- orientation

<400> SEQUENCE: 37

Xaa Gln Gln Thr Phe Xaa Asp Leu Trp Arg Leu Leu Xaa
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (12)..(12)
<223> OTHER INFORMATION: Any uncross-linked or cross-linked amino acid
      in R-or S- orientation
```

```
<400> SEQUENCE: 38

Xaa Leu Ser Gln Gln Thr Phe Xaa Asp Leu Trp Xaa Leu Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (6)..(6)
<223> OTHER INFORMATION: Any uncross-linked or cross-linked amino acid
      in R-or S- orientation
<220> FEATURE:
<221> NAME/KEY: MOD_RES
<222> LOCATION: (10)..(10)
<223> OTHER INFORMATION: Any uncross-linked or cross-linked amino acid
      in R-or S- orientation

<400> SEQUENCE: 39

Xaa Gln Gln Thr Phe Xaa Asp Leu Trp Xaa Leu Leu
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (6)..(6)
<223> OTHER INFORMATION: Any uncross-linked or cross-linked amino acid
      in R-or S- orientation
<220> FEATURE:
<221> NAME/KEY: MOD_RES
<222> LOCATION: (13)..(13)
<223> OTHER INFORMATION: Any uncross-linked or cross-linked amino acid
      in R-or S- orientation

<400> SEQUENCE: 40

Xaa Gln Gln Thr Ala Xaa Asp Leu Trp Arg Leu Leu Xaa Glu Asn
1               5                   10                  15

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(myristoyl)
<220> FEATURE:
<221> NAME/KEY: MOD_RES
<222> LOCATION: (2)..(2)
<223> OTHER INFORMATION: Beta-alanine or not present
<220> FEATURE:
<221> NAME/KEY: MOD_RES
```

```
<222> LOCATION: (9)..(9)
<223> OTHER INFORMATION: Any uncross-linked or cross-linked amino acid
      in R-or S- orientation
<220> FEATURE:
<221> NAME/KEY: MOD_RES
<222> LOCATION: (16)..(16)
<223> OTHER INFORMATION: Any uncross-linked or cross-linked amino acid
      in R-or S- orientation

<400> SEQUENCE: 41

Lys Xaa Gln Ser Gln Gln Thr Phe Xaa Asn Leu Trp Arg Leu Leu Xaa
1               5                   10                  15

Gln Asn

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(biotin)
<220> FEATURE:
<221> NAME/KEY: MOD_RES
<222> LOCATION: (2)..(2)
<223> OTHER INFORMATION: Beta-alanine or not present
<220> FEATURE:
<221> NAME/KEY: MOD_RES
<222> LOCATION: (9)..(9)
<223> OTHER INFORMATION: Any uncross-linked or cross-linked amino acid
      in R-or S- orientation
<220> FEATURE:
<221> NAME/KEY: MOD_RES
<222> LOCATION: (16)..(16)
<223> OTHER INFORMATION: Any uncross-linked or cross-linked amino acid
      in R-or S- orientation

<400> SEQUENCE: 42

Lys Xaa Gln Ser Gln Gln Thr Phe Xaa Asn Leu Trp Arg Leu Leu Xaa
1               5                   10                  15

Gln Asn

<210> SEQ ID NO 43
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(polyethylene glycol 3)
<220> FEATURE:
<221> NAME/KEY: MOD_RES
<222> LOCATION: (2)..(2)
<223> OTHER INFORMATION: Beta-alanine or not present
<220> FEATURE:
<221> NAME/KEY: MOD_RES
<222> LOCATION: (9)..(9)
<223> OTHER INFORMATION: Any uncross-linked or cross-linked amino acid
      in R-or S- orientation
<220> FEATURE:
<221> NAME/KEY: MOD_RES
<222> LOCATION: (16)..(16)
<223> OTHER INFORMATION: Any uncross-linked or cross-linked amino acid
      in R-or S- orientation

<400> SEQUENCE: 43
```

```
Lys Xaa Gln Ser Gln Gln Thr Phe Xaa Asn Leu Trp Arg Leu Leu Xaa
1               5                   10                  15

Gln Asn

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 44

Xaa Gln Ser Gln Gln Thr Phe Xaa Asn Leu Trp Arg Leu Leu Xaa Gln
1               5                   10                  15

Asn

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine or not present
<220> FEATURE:
<221> NAME/KEY: MOD_RES
<222> LOCATION: (8)..(8)
<223> OTHER INFORMATION: Any uncross-linked or cross-linked amino acid
      in R-or S- orientation
<220> FEATURE:
<221> NAME/KEY: MOD_RES
<222> LOCATION: (15)..(15)
<223> OTHER INFORMATION: Any uncross-linked or cross-linked amino acid
      in R-or S- orientation

<400> SEQUENCE: 45

Xaa Gln Ser Gln Gln Thr Ala Xaa Asn Leu Trp Arg Leu Leu Xaa Gln
1               5                   10                  15

Asn

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
```

```
<221> NAME/KEY: MOD_RES
<222> LOCATION: (14)..(14)
<223> OTHER INFORMATION: Any uncross-linked or cross-linked amino acid
      in R-or S- orientation

<400> SEQUENCE: 46

Gln Ser Gln Gln Thr Phe Xaa Asp Leu Trp Arg Leu Leu Xaa Gln Asn
1               5                   10                  15

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any uncross-linked or cross-linked amino acid
      in R-or S- orientation
<220> FEATURE:
<221> NAME/KEY: MOD_RES
<222> LOCATION: (11)..(11)
<223> OTHER INFORMATION: Any uncross-linked or cross-linked amino acid
      in R-or S- orientation

<400> SEQUENCE: 47

Gln Thr Phe Xaa Asn Leu Trp Arg Leu Leu Xaa
1               5                   10

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any uncross-linked or cross-linked amino acid
      in R-or S- orientation
<220> FEATURE:
<221> NAME/KEY: MOD_RES
<222> LOCATION: (11)..(11)
<223> OTHER INFORMATION: Any uncross-linked or cross-linked amino acid
      in R-or S- orientation

<400> SEQUENCE: 48

Gln Ser Gln Gln Thr Phe Xaa Asn Leu Trp Xaa Leu Leu Pro Gln Asn
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any uncross-linked or cross-linked amino acid
      in R-or S- orientation
<220> FEATURE:
<221> NAME/KEY: MOD_RES
<222> LOCATION: (7)..(7)
<223> OTHER INFORMATION: Any uncross-linked or cross-linked amino acid
      in R-or S- orientation

<400> SEQUENCE: 49
```

Gln Ser Xaa Gln Thr Phe Xaa Asn Leu Trp Arg Leu Leu Pro Gln Asn
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any uncross-linked or cross-linked amino acid
      in R-or S- orientation
<220> FEATURE:
<221> NAME/KEY: MOD_RES
<222> LOCATION: (5)..(5)
<223> OTHER INFORMATION: Any uncross-linked or cross-linked amino acid
      in R-or S- orientation

<400> SEQUENCE: 50

Xaa Thr Phe Ser Xaa Leu Trp Lys Leu Leu
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any uncross-linked or cross-linked amino acid
      in R-or S- orientation
<220> FEATURE:
<221> NAME/KEY: MOD_RES
<222> LOCATION: (8)..(8)
<223> OTHER INFORMATION: Any uncross-linked or cross-linked amino acid
      in R-or S- orientation

<400> SEQUENCE: 51

Glu Thr Phe Xaa Asp Leu Trp Xaa Leu Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any uncross-linked or cross-linked amino acid
      in R-or S- orientation
<220> FEATURE:
<221> NAME/KEY: MOD_RES
<222> LOCATION: (8)..(8)
<223> OTHER INFORMATION: Any uncross-linked or cross-linked amino acid
      in R-or S- orientation

<400> SEQUENCE: 52

Gln Thr Phe Xaa Asn Leu Trp Xaa Leu Leu
1               5                   10

<210> SEQ ID NO 53
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any uncross-linked or cross-linked amino acid
      in R-or S- orientation
<220> FEATURE:
<221> NAME/KEY: MOD_RES
<222> LOCATION: (5)..(5)
<223> OTHER INFORMATION: Any uncross-linked or cross-linked amino acid
      in R-or S- orientation

<400> SEQUENCE: 53

Xaa Ser Gln Glu Xaa Phe Ser Asn Leu Trp Lys Leu Leu
1               5                   10
```